(12) United States Patent
Raucher et al.

(10) Patent No.: US 8,841,414 B1
(45) Date of Patent: *Sep. 23, 2014

(54) TARGETED DELIVERY OF THERAPEUTIC PEPTIDES BY THERMALLY RESPONSIVE BIOPOLYMERS

(75) Inventors: Drazen Raucher, Madison, MS (US); Gene Bidwell, III, Jackson, MS (US)

(73) Assignee: University of Mississippi Medical Center, Jackson, MS (US)

( * ) Notice: Subject to any disclaimer, the term of this patent is extended or adjusted under 35 U.S.C. 154(b) by 31 days.

This patent is subject to a terminal disclaimer.

(21) Appl. No.: 12/789,215

(22) Filed: May 27, 2010

Related U.S. Application Data

(63) Continuation-in-part of application No. 12/422,970, filed on Apr. 13, 2009, now abandoned, and a continuation-in-part of application No. 12/162,283, filed as application No. PCT/US2007/061240 on Jan. 29, 2007.

(60) Provisional application No. 61/044,424, filed on Apr. 11, 2008, provisional application No. 60/762,919, filed on Jan. 27, 2006.

(51) Int. Cl.
*C07K 14/00* (2006.01)
*A61K 38/16* (2006.01)

(52) U.S. Cl.
USPC ........... 530/350; 514/1.2; 514/19.3; 530/345; 530/409

(58) Field of Classification Search
None
See application file for complete search history.

(56) References Cited

U.S. PATENT DOCUMENTS

| 2003/0124742 | A1 | 7/2003 | Prakash | |
|---|---|---|---|---|
| 2004/0191843 | A1* | 9/2004 | Wright et al. | 435/7.23 |
| 2004/0234497 | A1 | 11/2004 | Luo et al. | |
| 2007/0265197 | A1* | 11/2007 | Furgeson et al. | 514/7 |
| 2010/0120679 | A1* | 5/2010 | Xu et al. | 514/12 |

FOREIGN PATENT DOCUMENTS

| WO | WO2006/001806 | 1/2006 |
|---|---|---|
| WO | WO 2007090094 A2 * | 8/2007 |

OTHER PUBLICATIONS

Bidwell III et al. Targeting a c-Myc inhibitory polypeptide to specific intracellular compartments . . . Journal of Controlled Release. 2009, vol. 135, pp. 2-10 (available online Nov. 28, 2008).*
Massodi et al. Evaluation of cell penetrating peptide fused to elastin-like polypeptide for drug delivery. Journal of Controlled Release. 2005, vol. 108, pp. 396-408.*
Massodi et al. Application of Thermally Responsive Elastin-like Polypeptide Fused . . . Molecule. Jun. 4, 2009, vol. 14, pp. 1999-2015.*
Massodi et al. Inhibition of ovarian cancer cell proliferation . . . International Journal of Cancer. 2010, vol. 126, pp. 533-544 (online Jul. 8, 2009).*
Meyer et al. Drug targeting using thermally responsive polymers and local hyperthermia. Journal of Controlled Release. 2001, vol. 74, pp. 213-224.*

(Continued)

*Primary Examiner* — Jeffrey E Russel
(74) *Attorney, Agent, or Firm* — Stite & Harbison PLLC; Mandy Wilson Decker; Nicolo Davidson

(57) ABSTRACT

A compound including a cell penetrating peptide (CPP), an elastin-like polypeptide (ELP), and a therapeutic peptide (TP) can be preferentially directed to a target site by applying hyperthermia. The compound can be useful for the treatment of tumors.

9 Claims, 29 Drawing Sheets

(56) References Cited

OTHER PUBLICATIONS

Dreher, M.R. et al., Evaluation of an elastin-like polypeptide-doxorubincin conjugate for cancer therapy; Journal of Controlled Release; 2003, vol. 91; pp. 31-43

Massodi, I, et al., Evaluation of cell penetrating peptides fused to elastin-like polypeptide for drug delivery; Journal of controlled Release; 2005; vol. 108; pp. 396-408.

Meyer, D.E., et al., Targeting a Genetically Engineered Elastin-like Polypeptide to Solid Tumors by Local Hyperthermia; Cancer Research; Feb. 15, 2001; vol. 61, pp. 1548-1554.

Massodi, I, et al., Inhibition of ovarian cancer cell metastasis by a fusion polypeptide Tat-ELP; Clin Exp Metastasis; 2009; 26; pp. 251-260.

Bidwell, G.L., et al Targeting a o-Myc inhibitory polypeptide to specific intracellular compartments using cell penetrating peptides, Jouranal of Constrolled Relase: 2009 (article in press).

Massodi, I., et al A thermally responsive Tat-elastin-like polypeptide fusion protein induces membrane leakage, apoptosis, and cell death in human breast cancer cells; Journal of Drug Targeting; Nov. 2007; 15(9); pp. 611-622.

Bidwell GL, III, et al Application of thermally responsive polypeptides directed against c-Myc transcriptional function for cancer therapy; Mol Cancer Ther 2005; 4(7); 1076-85.

Bidwell GL, III, et al Enhancing the antiproliferative effect of topoisomerase II inhibitors using a polypeptide inhibitor of c-Myc; Biochemical Pharmacology; 2006; 71; pp. 248-256.

Bidwell GL III, et al Development of elastin-like polypeptide for thermally targeted delivery of doxorubicin; Biochemical Pharmacology; 2007; 73; pp. 620-631.

Bidwell GL, III, et al A thermally targeted elastin-like polypeptide-doxorubicin conjugate overcomes drug resistance; Invest New Drugs; 2007; 25; pp. 313-326.

Raucher, et al Thermally targeted delivery of chemotherapeutics and anti-cancer peptides by elastin-like polypeptide: Expert Opinion, Drug Deliv. (2008) 5(3):1-6.

* cited by examiner

A.

B.

SEQUENCE LISTING

```
<160> NUMBER OF SEQ ID NOS: 45

<210> SEQ ID NO 1
<211> LENGTH: 11
<212> TYPE: PRT
<213> ORGANISM: Artificial Sequence
<220> FEATURE:
<223> OTHER INFORMATION: Tat CPP

<400> SEQUENCE: 1

Tyr Gly Arg Lys Lys Arg Arg Gln Arg Arg Arg
1               5                   10

<210> SEQ ID NO 2
<211> LENGTH: 16
<212> TYPE: PRT
<213> ORGANISM: Artificial
<220> FEATURE:
<223> OTHER INFORMATION: Antp CPP

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 24
<212> TYPE: PRT
<213> ORGANISM: Artificial Sequence
<220> FEATURE:
<223> OTHER INFORMATION: Bac-7 CPP

<400> SEQUENCE: 3

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 4
<211> LENGTH: 18
<212> TYPE: PRT
<213> ORGANISM: Artificial Sequence
<220> FEATURE:
<223> OTHER INFORMATION: SynB1 CPP

<400> SEQUENCE: 4

Arg Gly Gly Arg Leu Ser Tyr Ser Arg Arg Arg Phe Ser Thr Ser Thr
1               5                   10                  15

Gly Arg

<210> SEQ ID NO 5
<211> LENGTH: 28
<212> TYPE: PRT
<213> ORGANISM: Artificial Sequence
<220> FEATURE:
<223> OTHER INFORMATION: SynB1-NLS CPP
```

```
<400> SEQUENCE: 5

Arg Gly Gly Arg Leu Ser Tyr Ser Arg Arg Phe Ser Thr Ser Thr
1               5                   10                  15

Gly Arg Trp Ser Gln Pro Lys Lys Arg Lys Val
            20                  25

<210> SEQ ID NO 6
<211> LENGTH: 7
<212> TYPE: PRT
<213> ORGANISM: Artificial Sequence
<220> FEATURE:
<223> OTHER INFORMATION: R-7 CPP

<400> SEQUENCE: 6

Arg Arg Arg Arg Arg Arg Arg
1               5

<210> SEQ ID NO 7
<211> LENGTH: 8
<212> TYPE: PRT
<213> ORGANISM: Artificial Sequence
<220> FEATURE:
<223> OTHER INFORMATION: R-8 CPP

<400> SEQUENCE: 7

Arg Arg Arg Arg Arg Arg Arg Arg
1               5

<210> SEQ ID NO 8
<211> LENGTH: 9
<212> TYPE: PRT
<213> ORGANISM: Artificial Sequence
<220> FEATURE:
<223> OTHER INFORMATION: R-9 CPP

<400> SEQUENCE: 8

Arg Arg Arg Arg Arg Arg Arg Arg Arg
1               5

<210> SEQ ID NO 9
<211> LENGTH: 10
<212> TYPE: PRT
<213> ORGANISM: Artificial Sequence
<220> FEATURE:
<223> OTHER INFORMATION: R-10 CPP

<400> SEQUENCE: 9

Arg Arg Arg Arg Arg Arg Arg Arg Arg Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: R-11 CPP

<400> SEQUENCE: 10

Arg Arg Arg Arg Arg Arg Arg Arg Arg Arg Arg
1               5                   10

<210> SEQ ID NO 11
<211> LENGTH: 34
<212> TYPE: PRT
<213> ORGANISM: Artificial Sequence
```

```
<220> FEATURE:
<223> OTHER INFORMATION: VP22 CPP

<400> SEQUENCE: 11

Asp Ala Ala Thr Ala Thr Arg Gly Arg Ser Ala Ala Ser Arg Pro Thr
1               5                   10                  15

Gln Arg Pro Arg Ala Pro Ala Arg Ser Ala Ser Arg Pro Arg Arg Pro
            20                  25                  30

Val Gln

<210> SEQ ID NO 12
<211> LENGTH: 27
<212> TYPE: PRT
<213> ORGANISM: Artificial Sequence
<220> FEATURE:
<223> OTHER INFORMATION: Trans CPP

<400> SEQUENCE: 12

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 13
<211> LENGTH: 18
<212> TYPE: PRT
<213> ORGANISM: Artificial Sequence
<220> FEATURE:
<223> OTHER INFORMATION: MAP CPP

<400> SEQUENCE: 13

Lys Leu Ala Leu Lys Leu Ala Leu Lys Ala Leu Lys Ala Ala Leu Lys
1               5                   10                  15

Leu Ala

<210> SEQ ID NO 14
<211> LENGTH: 18
<212> TYPE: PRT
<213> ORGANISM: Artificial Sequence
<220> FEATURE:
<223> OTHER INFORMATION: pVEC CPP

<400> SEQUENCE: 14

Leu Leu Ile Ile Leu Arg Arg Arg Ile Arg Lys Gln Ala His Ala His
1               5                   10                  15

Ser Lys

<210> SEQ ID NO 15
<211> LENGTH: 16
<212> TYPE: PRT
<213> ORGANISM: Artificial Sequence
<220> FEATURE:
<223> OTHER INFORMATION: MTS CPP

<400> SEQUENCE: 15

Ala Ala Val Ala Leu Leu Pro Ala Val Leu Leu Ala Leu Leu Ala Pro
1               5                   10                  15

<210> SEQ ID NO 16
<211> LENGTH: 24
<212> TYPE: PRT
<213> ORGANISM: Artificial Sequence
<220> FEATURE:
<223> OTHER INFORMATION: nCT-derived CPP
```

```
<400> SEQUENCE: 16

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 17
<211> LENGTH: 27
<212> TYPE: PRT
<213> ORGANISM: Artificial Sequence
<220> FEATURE:
<223> OTHER INFORMATION: MPG CPP

<400> SEQUENCE: 17

Gly Ala Leu Phe Leu Gly Phe Leu Gly Ala Ala Gly Ser Thr Met Gly
1               5                   10                  15

Ala Trp Ser Gln Pro Lys Lys Arg Lys Val
            20                  25

<210> SEQ ID NO 18
<211> LENGTH: 21
<212> TYPE: PRT
<213> ORGANISM: Artificial Sequence
<220> FEATURE:
<223> OTHER INFORMATION: Buforin 2 CPP

<400> SEQUENCE: 18

Thr Arg Ser Ser Arg Ala Gly Leu Gln Phe Pro Val Gly Arg Val His
1               5                   10                  15

Arg Leu Leu Arg Lys
            20

<210> SEQ ID NO 19
<211> LENGTH: 21
<212> TYPE: PRT
<213> ORGANISM: Artificial Sequence
<220> FEATURE:
<223> OTHER INFORMATION: PEP-1 CPP

<400> SEQUENCE: 19

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 20
<211> LENGTH: 23
<212> TYPE: PRT
<213> ORGANISM: Artificial Sequence
<220> FEATURE:
<223> OTHER INFORMATION: Magainin 2 CPP

<400> SEQUENCE: 20

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 21
<211> LENGTH: 758
<212> TYPE: PRT
<213> ORGANISM: Artificial Sequence
<220> FEATURE:
<223> OTHER INFORMATION: ELP 1
```

<400> SEQUENCE: 21

Met Ser Lys Gly Pro Gly Val Gly Val Pro Gly Val Gly Val Pro Gly
1               5                   10                  15

Gly Gly Val Pro Gly Ala Gly Val Pro Gly Val Gly Val Pro Gly Val
            20                  25                  30

Gly Val Pro Gly Val Gly Val Pro Gly Gly Gly Val Pro Gly Ala Gly
        35                  40                  45

Val Pro Gly Gly Gly Val Pro Gly Val Gly Val Pro Gly Val Gly Val
50                  55                  60

Pro Gly Gly Gly Val Pro Gly Ala Gly Val Pro Gly Val Gly Val Pro
65                  70                  75                  80

Gly Val Gly Val Pro Gly Val Gly Val Pro Gly Gly Gly Val Pro Gly
                85                  90                  95

Ala Gly Val Pro Gly Gly Gly Val Pro Gly Val Gly Val Pro Gly Val
            100                 105                 110

Gly Val Pro Gly Gly Gly Val Pro Gly Ala Gly Val Pro Gly Val Gly
        115                 120                 125

Val Pro Gly Val Gly Val Pro Gly Val Gly Val Pro Gly Gly Gly Val
    130                 135                 140

Pro Gly Ala Gly Val Pro Gly Gly Gly Val Pro Gly Val Gly Val Pro
145                 150                 155                 160

Gly Val Gly Val Pro Gly Gly Gly Val Pro Gly Ala Gly Val Pro Gly
                165                 170                 175

Val Gly Val Pro Gly Val Gly Val Pro Gly Val Gly Val Pro Gly Gly
            180                 185                 190

Gly Val Pro Gly Ala Gly Val Pro Gly Gly Gly Val Pro Gly Val Gly
        195                 200                 205

Val Pro Gly Val Gly Val Pro Gly Gly Gly Val Pro Gly Ala Gly Val
    210                 215                 220

Pro Gly Val Gly Val Pro Gly Val Gly Val Pro Gly Val Gly Val Pro
225                 230                 235                 240

Gly Gly Gly Val Pro Gly Ala Gly Val Pro Gly Gly Gly Val Pro Gly
                245                 250                 255

Val Gly Val Pro Gly Val Gly Val Pro Gly Gly Gly Val Pro Gly Ala
            260                 265                 270

Gly Val Pro Gly Val Gly Val Pro Gly Val Gly Val Pro Gly Val Gly
        275                 280                 285

Val Pro Gly Gly Gly Val Pro Gly Ala Gly Val Pro Gly Gly Gly Val
    290                 295                 300

Pro Gly Val Gly Val Pro Gly Val Gly Val Pro Gly Gly Gly Val Pro
305                 310                 315                 320

Gly Ala Gly Val Pro Gly Val Gly Val Pro Gly Val Gly Val Pro Gly
                325                 330                 335

Val Gly Val Pro Gly Gly Gly Val Pro Gly Ala Gly Val Pro Gly Gly
            340                 345                 350

Gly Val Pro Gly Val Gly Val Pro Gly Val Gly Val Pro Gly Gly Gly
        355                 360                 365

Val Pro Gly Ala Gly Val Pro Gly Val Gly Val Pro Gly Val Gly Val
    370                 375                 380

Pro Gly Val Gly Val Pro Gly Gly Gly Val Pro Gly Ala Gly Val Pro
385                 390                 395                 400

Gly Gly Gly Val Pro Gly Val Gly Val Pro Gly Val Gly Val Pro Gly

```
            405                 410                 415
Gly Gly Val Pro Gly Ala Gly Val Pro Gly Val Gly Val Pro Gly Val
                420                 425                 430
Gly Val Pro Gly Val Gly Val Pro Gly Gly Val Pro Gly Ala Gly
            435                 440                 445
Val Pro Gly Gly Gly Val Pro Gly Val Gly Val Pro Gly Val Gly Val
450                 455                 460
Pro Gly Gly Gly Val Pro Gly Ala Gly Val Pro Gly Val Gly Val Pro
465                 470                 475                 480
Gly Val Gly Val Pro Gly Val Gly Val Pro Gly Gly Val Pro Gly
            485                 490                 495
Ala Gly Val Pro Gly Gly Val Pro Gly Val Gly Val Pro Gly Val
                500                 505                 510
Gly Val Pro Gly Gly Val Pro Gly Ala Gly Val Pro Gly Val Gly
            515                 520                 525
Val Pro Gly Val Gly Val Pro Gly Val Gly Val Pro Gly Gly Gly Val
                530                 535                 540
Pro Gly Ala Gly Val Pro Gly Gly Val Pro Gly Val Gly Val Pro
545                 550                 555                 560
Gly Val Gly Val Pro Gly Val Gly Val Pro Gly Ala Gly Val Pro Gly
                565                 570                 575
Val Gly Val Pro Gly Val Gly Val Pro Gly Val Gly Val Pro Gly Gly
            580                 585                 590
Gly Val Pro Gly Ala Gly Val Pro Gly Gly Gly Val Pro Gly Val
                595                 600                 605
Val Pro Gly Val Gly Val Pro Gly Gly Gly Val Pro Gly Ala Gly Val
            610                 615                 620
Pro Gly Val Gly Val Pro Gly Val Gly Val Pro Gly Val Gly Val Pro
625                 630                 635                 640
Gly Gly Gly Val Pro Gly Ala Gly Val Pro Gly Gly Gly Val Pro Gly
                645                 650                 655
Val Gly Val Pro Gly Val Gly Val Pro Gly Gly Gly Val Pro Gly Ala
            660                 665                 670
Gly Val Pro Gly Val Gly Val Pro Gly Val Gly Val Pro Gly Val Gly
                675                 680                 685
Val Pro Gly Gly Val Pro Gly Ala Gly Val Pro Gly Gly Gly Val
            690                 695                 700
Pro Gly Val Gly Val Pro Gly Val Gly Val Pro Gly Gly Gly Val Pro
705                 710                 715                 720
Gly Ala Gly Val Pro Gly Val Gly Val Pro Gly Val Gly Val Pro Gly
                725                 730                 735
Val Gly Val Pro Gly Gly Gly Val Pro Gly Ala Gly Val Pro Gly Gly
            740                 745                 750
Gly Val Pro Gly Trp Pro
            755

<210> SEQ ID NO 22
<211> LENGTH: 808
<212> TYPE: PRT
<213> ORGANISM: Artificial Sequence
<220> FEATURE:
<223> OTHER INFORMATION: ELP 2

<400> SEQUENCE: 22

Met Ser Lys Gly Pro Gly Val Gly Val Pro Gly Ala Gly Val Pro Gly
```

```
1               5                   10                  15
Gly Gly Val Pro Gly Ala Gly Val Pro Gly Gly Gly Val Pro Gly Ala
                20                  25                  30
Gly Val Pro Gly Gly Val Pro Gly Ala Gly Val Pro Gly Gly Gly
            35                  40                  45
Val Pro Gly Ala Gly Val Pro Gly Gly Gly Val Pro Gly Ala Gly Val
        50                  55                  60
Pro Gly Gly Gly Val Pro Gly Ala Gly Val Pro Gly Gly Gly Val Pro
65                  70                  75                  80
Gly Ala Gly Val Pro Gly Val Gly Val Pro Gly Ala Gly Val Pro Gly
                85                  90                  95
Gly Gly Val Pro Gly Ala Gly Val Pro Gly Gly Gly Val Pro Gly Ala
                100                 105                 110
Gly Val Pro Gly Gly Val Pro Gly Ala Gly Val Pro Gly Gly Gly
            115                 120                 125
Val Pro Gly Ala Gly Val Pro Gly Gly Gly Val Pro Gly Ala Gly Val
        130                 135                 140
Pro Gly Gly Gly Val Pro Gly Ala Gly Val Pro Gly Gly Gly Val Pro
145                 150                 155                 160
Gly Ala Gly Val Pro Gly Val Gly Val Pro Gly Ala Gly Val Pro Gly
                165                 170                 175
Gly Gly Val Pro Gly Ala Gly Val Pro Gly Gly Gly Val Pro Gly Ala
                180                 185                 190
Gly Val Pro Gly Gly Val Pro Gly Ala Gly Val Pro Gly Gly Gly
            195                 200                 205
Val Pro Gly Ala Gly Val Pro Gly Gly Gly Val Pro Gly Ala Gly Val
        210                 215                 220
Pro Gly Gly Gly Val Pro Gly Ala Gly Val Pro Gly Gly Gly Val Pro
225                 230                 235                 240
Gly Ala Gly Val Pro Gly Val Gly Val Pro Gly Ala Gly Val Pro Gly
                245                 250                 255
Gly Gly Val Pro Gly Ala Gly Val Pro Gly Gly Gly Val Pro Gly Ala
                260                 265                 270
Gly Val Pro Gly Gly Val Pro Gly Ala Gly Val Pro Gly Gly Gly
            275                 280                 285
Val Pro Gly Ala Gly Val Pro Gly Gly Gly Val Pro Gly Ala Gly Val
        290                 295                 300
Pro Gly Gly Gly Val Pro Gly Ala Gly Val Pro Gly Gly Gly Val Pro
305                 310                 315                 320
Gly Ala Gly Val Pro Gly Val Gly Val Pro Gly Ala Gly Val Pro Gly
                325                 330                 335
Gly Gly Val Pro Gly Ala Gly Val Pro Gly Gly Gly Val Pro Gly Ala
                340                 345                 350
Gly Val Pro Gly Gly Val Pro Gly Ala Gly Val Pro Gly Gly Gly
            355                 360                 365
Val Pro Gly Ala Gly Val Pro Gly Gly Gly Val Pro Gly Ala Gly Val
        370                 375                 380
Pro Gly Gly Gly Val Pro Gly Ala Gly Val Pro Gly Gly Gly Val Pro
385                 390                 395                 400
Gly Ala Gly Val Pro Gly Val Gly Val Pro Gly Ala Gly Val Pro Gly
                405                 410                 415
Gly Gly Val Pro Gly Ala Gly Val Pro Gly Gly Gly Val Pro Gly Ala
                420                 425                 430
```

Gly Val Pro Gly Gly Val Pro Ala Gly Val Pro Gly Gly
            435                 440                 445

Val Pro Gly Ala Gly Val Pro Gly Gly Val Pro Ala Gly Val
        450                 455                 460

Pro Gly Gly Gly Val Pro Gly Ala Gly Val Pro Gly Gly Gly Val Pro
465                 470                 475                 480

Gly Ala Gly Val Pro Gly Val Gly Val Pro Gly Ala Gly Val Pro Gly
                485                 490                 495

Gly Gly Val Pro Gly Ala Gly Val Pro Gly Gly Val Pro Gly Ala
            500                 505                 510

Gly Val Pro Gly Gly Val Pro Gly Ala Gly Val Pro Gly Gly
        515                 520                 525

Val Pro Gly Ala Gly Val Pro Gly Gly Val Pro Gly Ala Gly Val
        530                 535                 540

Pro Gly Gly Gly Val Pro Gly Ala Gly Val Pro Gly Gly Gly Val Pro
545                 550                 555                 560

Gly Ala Gly Val Pro Gly Val Gly Val Pro Gly Ala Gly Val Pro Gly
                565                 570                 575

Gly Gly Val Pro Gly Ala Gly Val Pro Gly Gly Val Pro Gly Ala
            580                 585                 590

Gly Val Pro Gly Gly Val Pro Gly Ala Gly Val Pro Gly Gly Gly
        595                 600                 605

Val Pro Gly Ala Gly Val Pro Gly Gly Val Pro Gly Ala Gly Val
        610                 615                 620

Pro Gly Gly Gly Val Pro Gly Ala Gly Val Pro Gly Gly Gly Val Pro
625                 630                 635                 640

Gly Ala Gly Val Pro Gly Val Gly Val Pro Gly Ala Gly Val Pro Gly
                645                 650                 655

Gly Gly Val Pro Gly Ala Gly Val Pro Gly Gly Val Pro Gly Ala
            660                 665                 670

Gly Val Pro Gly Gly Val Pro Gly Ala Gly Val Pro Gly Gly Gly
        675                 680                 685

Val Pro Gly Ala Gly Val Pro Gly Gly Val Pro Gly Ala Gly Val
        690                 695                 700

Pro Gly Gly Gly Val Pro Gly Ala Gly Val Pro Gly Gly Gly Val Pro
705                 710                 715                 720

Gly Ala Gly Val Pro Gly Val Gly Val Pro Gly Ala Gly Val Pro Gly
                725                 730                 735

Gly Gly Val Pro Gly Ala Gly Val Pro Gly Gly Val Pro Gly Ala
            740                 745                 750

Gly Val Pro Gly Gly Val Pro Gly Ala Gly Val Pro Gly Gly Gly
        755                 760                 765

Val Pro Gly Ala Gly Val Pro Gly Gly Val Pro Gly Ala Gly Val
        770                 775                 780

Pro Gly Gly Gly Val Pro Gly Ala Gly Val Pro Gly Gly Gly Val Pro
785                 790                 795                 800

Gly Ala Gly Val Pro Gly Trp Pro
            805

<210> SEQ ID NO 23
<211> LENGTH: 773
<212> TYPE: PRT
<213> ORGANISM: Artificial Sequence
<220> FEATURE:

<223> OTHER INFORMATION: Tat-ELP1

<400> SEQUENCE: 23

Met Tyr Gly Arg Lys Lys Arg Arg Gln Arg Arg Gly Gly Pro Gly
1               5                   10                  15
Val Gly Val Pro Gly Val Gly Val Pro Gly Gly Gly Val Pro Gly Ala
            20                  25                  30
Gly Val Pro Gly Val Gly Val Pro Gly Val Gly Val Pro Gly Val Gly
            35                  40                  45
Val Pro Gly Gly Gly Val Pro Gly Ala Gly Val Pro Gly Gly Gly Val
        50                  55                  60
Pro Gly Val Gly Val Pro Gly Val Gly Val Pro Gly Gly Gly Val Pro
65                  70                  75                  80
Gly Ala Gly Val Pro Gly Val Gly Val Pro Gly Val Gly Val Pro Gly
                85                  90                  95
Val Gly Val Pro Gly Gly Gly Val Pro Gly Ala Gly Val Pro Gly Gly
            100                 105                 110
Gly Val Pro Gly Val Gly Val Pro Gly Val Gly Val Pro Gly Gly Gly
            115                 120                 125
Val Pro Gly Ala Gly Val Pro Gly Val Gly Val Pro Gly Val Gly Val
        130                 135                 140
Pro Gly Val Gly Val Pro Gly Gly Gly Val Pro Gly Ala Gly Val Pro
145                 150                 155                 160
Gly Gly Gly Val Pro Gly Val Gly Val Pro Gly Val Gly Val Pro Gly
                165                 170                 175
Gly Gly Val Pro Gly Ala Gly Val Pro Gly Val Gly Val Pro Gly Val
            180                 185                 190
Gly Val Pro Gly Val Gly Val Pro Gly Gly Gly Val Pro Gly Ala Gly
            195                 200                 205
Val Pro Gly Gly Gly Val Pro Gly Val Gly Val Pro Gly Val Gly Val
        210                 215                 220
Pro Gly Gly Gly Val Pro Gly Ala Gly Val Pro Gly Val Gly Val Pro
225                 230                 235                 240
Gly Val Gly Val Pro Gly Val Gly Val Pro Gly Gly Gly Val Pro Gly
                245                 250                 255
Ala Gly Val Pro Gly Gly Gly Val Pro Gly Val Gly Val Pro Gly Val
            260                 265                 270
Gly Val Pro Gly Gly Gly Val Pro Gly Ala Gly Val Pro Gly Val Gly
            275                 280                 285
Val Pro Gly Val Gly Val Pro Gly Val Gly Val Pro Gly Gly Gly Val
        290                 295                 300
Pro Gly Ala Gly Val Pro Gly Gly Gly Val Pro Gly Val Gly Val Pro
305                 310                 315                 320
Gly Val Gly Val Pro Gly Gly Gly Val Pro Gly Ala Gly Val Pro Gly
                325                 330                 335
Val Gly Val Pro Gly Val Gly Val Pro Gly Val Gly Val Pro Gly Gly
            340                 345                 350
Gly Val Pro Gly Ala Gly Val Pro Gly Gly Gly Val Pro Gly Val Gly
            355                 360                 365
Val Pro Gly Val Gly Val Pro Gly Gly Gly Val Pro Gly Ala Gly Val
        370                 375                 380
Pro Gly Val Gly Val Pro Gly Val Gly Val Pro Gly Val Gly Val Pro
385                 390                 395                 400

Gly Gly Gly Val Pro Gly Ala Gly Val Pro Gly Gly Gly Val Pro Gly
            405                 410                 415
Val Gly Val Pro Gly Val Gly Val Pro Gly Gly Gly Val Pro Gly Ala
            420                 425                 430
Gly Val Pro Gly Val Gly Val Pro Gly Val Gly Val Pro Gly Val Gly
            435                 440                 445
Val Pro Gly Gly Gly Val Pro Gly Ala Gly Val Pro Gly Gly Gly Val
            450                 455                 460
Pro Gly Val Gly Val Pro Gly Val Gly Val Pro Gly Gly Gly Val Pro
465                 470                 475                 480
Gly Ala Gly Val Pro Gly Val Gly Val Pro Gly Val Gly Val Pro Gly
            485                 490                 495
Val Gly Val Pro Gly Gly Gly Val Pro Gly Ala Gly Val Pro Gly Gly
            500                 505                 510
Gly Val Pro Gly Val Gly Val Pro Gly Val Gly Val Pro Gly Gly Gly
            515                 520                 525
Val Pro Gly Ala Gly Val Pro Gly Val Gly Val Pro Gly Val Gly Val
            530                 535                 540
Pro Gly Val Gly Val Pro Gly Gly Gly Val Pro Gly Ala Gly Val Pro
545                 550                 555                 560
Gly Gly Gly Val Pro Gly Val Gly Val Pro Gly Val Gly Val Pro Gly
            565                 570                 575
Gly Gly Val Pro Gly Ala Gly Val Pro Gly Val Gly Val Pro Gly Val
            580                 585                 590
Gly Val Pro Gly Val Gly Val Pro Gly Gly Gly Val Pro Gly Ala Gly
            595                 600                 605
Val Pro Gly Gly Gly Val Pro Gly Val Gly Val Pro Gly Val Gly Val
            610                 615                 620
Pro Gly Gly Gly Val Pro Gly Ala Gly Val Pro Gly Val Gly Val Pro
625                 630                 635                 640
Gly Val Gly Val Pro Gly Val Gly Val Pro Gly Gly Gly Val Pro Gly
            645                 650                 655
Ala Gly Val Pro Gly Gly Gly Val Pro Gly Val Gly Val Pro Gly Val
            660                 665                 670
Gly Val Pro Gly Gly Gly Val Pro Gly Ala Gly Val Pro Gly Val Gly
            675                 680                 685
Val Pro Gly Val Gly Val Pro Gly Val Gly Val Pro Gly Gly Gly Val
            690                 695                 700
Pro Gly Ala Gly Val Pro Gly Gly Gly Val Pro Gly Val Gly Val Pro
705                 710                 715                 720
Gly Val Gly Val Pro Gly Gly Gly Val Pro Gly Ala Gly Val Pro Gly
            725                 730                 735
Val Gly Val Pro Gly Val Gly Val Pro Gly Val Gly Val Pro Gly Gly
            740                 745                 750
Gly Val Pro Gly Ala Gly Val Pro Gly Gly Gly Val Pro Gly Trp Pro
            755                 760                 765
Gly Ser Gly Gly Cys
    770

<210> SEQ ID NO 24
<211> LENGTH: 823
<212> TYPE: PRT
<213> ORGANISM: Artificial Sequence
<220> FEATURE:
<223> OTHER INFORMATION: ELP-Tat2

<400> SEQUENCE: 24

```
Met Tyr Gly Arg Lys Lys Arg Gln Arg Arg Gly Gly Pro Gly
1               5                   10                  15

Val Gly Val Pro Gly Ala Gly Val Pro Gly Gly Val Pro Gly Ala
            20                  25                  30

Gly Val Pro Gly Gly Val Pro Gly Ala Gly Val Pro Gly Gly
            35                  40                  45

Val Pro Gly Ala Gly Val Pro Gly Gly Gly Val Pro Gly Ala Gly Val
    50                  55                  60

Pro Gly Gly Gly Val Pro Gly Ala Gly Val Pro Gly Gly Gly Val Pro
65                  70                  75                  80

Gly Ala Gly Val Pro Gly Gly Gly Val Pro Gly Ala Gly Val Pro Gly
                85                  90                  95

Val Gly Val Pro Gly Ala Gly Val Pro Gly Gly Val Pro Gly Ala
            100                 105                 110

Gly Val Pro Gly Gly Val Pro Gly Ala Gly Val Pro Gly Gly
            115                 120                 125

Val Pro Gly Ala Gly Val Pro Gly Gly Gly Val Pro Gly Ala Gly Val
    130                 135                 140

Pro Gly Gly Gly Val Pro Gly Ala Gly Val Pro Gly Gly Gly Val Pro
145                 150                 155                 160

Gly Ala Gly Val Pro Gly Gly Gly Val Pro Gly Ala Gly Val Pro Gly
                165                 170                 175

Val Gly Val Pro Gly Ala Gly Val Pro Gly Gly Val Pro Gly Ala
            180                 185                 190

Gly Val Pro Gly Gly Val Pro Gly Ala Gly Val Pro Gly Gly
            195                 200                 205

Val Pro Gly Ala Gly Val Pro Gly Gly Gly Val Pro Gly Ala Gly Val
    210                 215                 220

Pro Gly Gly Gly Val Pro Gly Ala Gly Val Pro Gly Gly Gly Val Pro
225                 230                 235                 240

Gly Ala Gly Val Pro Gly Gly Gly Val Pro Gly Ala Gly Val Pro Gly
                245                 250                 255

Val Gly Val Pro Gly Ala Gly Val Pro Gly Gly Gly Val Pro Gly Ala
            260                 265                 270

Gly Val Pro Gly Gly Gly Val Pro Gly Ala Gly Val Pro Gly Gly Gly
            275                 280                 285

Val Pro Gly Ala Gly Val Pro Gly Gly Gly Val Pro Gly Ala Gly Val
    290                 295                 300

Pro Gly Gly Gly Val Pro Gly Ala Gly Val Pro Gly Gly Gly Val Pro
305                 310                 315                 320

Gly Ala Gly Val Pro Gly Gly Gly Val Pro Gly Ala Gly Val Pro Gly
                325                 330                 335

Val Gly Val Pro Gly Ala Gly Val Pro Gly Gly Gly Val Pro Gly Ala
            340                 345                 350

Gly Val Pro Gly Gly Gly Val Pro Gly Ala Gly Val Pro Gly Gly Gly
            355                 360                 365

Val Pro Gly Ala Gly Val Pro Gly Gly Gly Val Pro Gly Ala Gly Val
    370                 375                 380

Pro Gly Gly Gly Val Pro Gly Ala Gly Val Pro Gly Gly Gly Val Pro
385                 390                 395                 400

Gly Ala Gly Val Pro Gly Gly Gly Val Pro Gly Ala Gly Val Pro Gly
```

```
                    405                 410                 415
Val Gly Val Pro Gly Ala Gly Val Pro Gly Gly Val Pro Gly Ala
                420                 425                 430

Gly Val Pro Gly Gly Val Pro Gly Ala Gly Val Pro Gly Gly Gly
                435                 440                 445

Val Pro Gly Ala Gly Val Pro Gly Gly Gly Val Pro Gly Ala Gly Val
    450                 455                 460

Pro Gly Gly Gly Val Pro Gly Ala Gly Val Pro Gly Gly Gly Val Pro
465                 470                 475                 480

Gly Ala Gly Val Pro Gly Gly Gly Val Pro Gly Ala Gly Val Pro Gly
                485                 490                 495

Val Gly Val Pro Gly Ala Gly Val Pro Gly Gly Val Pro Gly Ala
                500                 505                 510

Gly Val Pro Gly Gly Val Pro Gly Ala Gly Val Pro Gly Gly Gly
                515                 520                 525

Val Pro Gly Ala Gly Val Pro Gly Gly Gly Val Pro Gly Ala Gly Val
    530                 535                 540

Pro Gly Gly Gly Val Pro Gly Ala Gly Val Pro Gly Gly Gly Val Pro
545                 550                 555                 560

Gly Ala Gly Val Pro Gly Gly Gly Val Pro Gly Ala Gly Val Pro Gly
                565                 570                 575

Val Gly Val Pro Gly Ala Gly Val Pro Gly Gly Val Pro Gly Ala
                580                 585                 590

Gly Val Pro Gly Gly Gly Val Pro Gly Ala Gly Val Pro Gly Gly Gly
                595                 600                 605

Val Pro Gly Ala Gly Val Pro Gly Gly Gly Val Pro Gly Ala Gly Val
    610                 615                 620

Pro Gly Gly Gly Val Pro Gly Ala Gly Val Pro Gly Gly Gly Val Pro
625                 630                 635                 640

Gly Ala Gly Val Pro Gly Gly Gly Val Pro Gly Ala Gly Val Pro Gly
                645                 650                 655

Val Gly Val Pro Gly Ala Gly Val Pro Gly Gly Gly Val Pro Gly Ala
                660                 665                 670

Gly Val Pro Gly Gly Gly Val Pro Gly Ala Gly Val Pro Gly Gly Gly
                675                 680                 685

Val Pro Gly Ala Gly Val Pro Gly Gly Gly Val Pro Gly Ala Gly Val
    690                 695                 700

Pro Gly Gly Gly Val Pro Gly Ala Gly Val Pro Gly Gly Gly Val Pro
705                 710                 715                 720

Gly Ala Gly Val Pro Gly Gly Gly Val Pro Gly Ala Gly Val Pro Gly
                725                 730                 735

Val Gly Val Pro Gly Ala Gly Val Pro Gly Gly Gly Val Pro Gly Ala
                740                 745                 750

Gly Val Pro Gly Gly Gly Val Pro Gly Ala Gly Val Pro Gly Gly Gly
                755                 760                 765

Val Pro Gly Ala Gly Val Pro Gly Gly Gly Val Pro Gly Ala Gly Val
    770                 775                 780

Pro Gly Gly Gly Val Pro Gly Ala Gly Val Pro Gly Gly Gly Val Pro
785                 790                 795                 800

Gly Ala Gly Val Pro Gly Gly Gly Val Pro Gly Ala Gly Val Pro Gly
                805                 810                 815

Trp Pro Gly Ser Gly Gly Cys
                820
```

<210> SEQ ID NO 25
<211> LENGTH: 774
<212> TYPE: PRT
<213> ORGANISM: Artificial Sequence
<220> FEATURE:
<223> OTHER INFORMATION: Antp-ELP1

<400> SEQUENCE: 25

```
Met Arg Gln Ile Lys Ile Trp Phe Gln Asn Arg Arg Met Lys Trp Lys
1               5                   10                  15

Lys Gly Cys Gly Pro Gly Val Gly Val Pro Gly Val Gly Val Pro Gly
            20                  25                  30

Gly Gly Val Pro Gly Ala Gly Val Pro Gly Val Gly Val Pro Gly Val
        35                  40                  45

Gly Val Pro Gly Val Gly Val Pro Gly Gly Val Pro Gly Ala Gly
    50                  55                  60

Val Pro Gly Gly Val Pro Gly Val Gly Val Pro Gly Val Gly Val
65                  70                  75                  80

Pro Gly Gly Gly Val Pro Gly Ala Gly Val Pro Gly Val Gly Val Pro
                85                  90                  95

Gly Val Gly Val Pro Gly Val Gly Val Pro Gly Gly Gly Val Pro Gly
            100                 105                 110

Ala Gly Val Pro Gly Gly Val Pro Gly Val Gly Val Pro Gly Val
        115                 120                 125

Gly Val Pro Gly Gly Val Pro Gly Ala Gly Val Pro Gly Val Gly
    130                 135                 140

Val Pro Gly Val Gly Val Pro Gly Val Gly Val Pro Gly Gly Gly Val
145                 150                 155                 160

Pro Gly Ala Gly Val Pro Gly Gly Val Pro Gly Val Gly Val Pro
                165                 170                 175

Gly Val Gly Val Pro Gly Gly Gly Val Pro Gly Ala Gly Val Pro Gly
            180                 185                 190

Val Gly Val Pro Gly Gly Val Pro Gly Val Gly Val Pro Gly Gly
        195                 200                 205

Gly Val Pro Gly Ala Gly Val Pro Gly Gly Gly Val Pro Gly Val Gly
    210                 215                 220

Val Pro Gly Val Gly Val Pro Gly Gly Val Pro Gly Ala Gly Val
225                 230                 235                 240

Pro Gly Val Gly Val Pro Gly Gly Val Pro Gly Val Gly Val Pro
                245                 250                 255

Gly Gly Gly Val Pro Gly Ala Gly Val Pro Gly Gly Gly Val Pro Gly
            260                 265                 270

Val Gly Val Pro Gly Val Gly Val Pro Gly Gly Gly Val Pro Gly Ala
        275                 280                 285

Gly Val Pro Gly Val Gly Val Pro Gly Val Gly Val Pro Gly Val Gly
    290                 295                 300

Val Pro Gly Gly Gly Val Pro Gly Ala Gly Val Pro Gly Gly Gly Val
305                 310                 315                 320

Pro Gly Val Gly Val Pro Gly Val Gly Val Pro Gly Gly Gly Val Pro
                325                 330                 335

Gly Ala Gly Val Pro Gly Val Gly Val Pro Gly Val Gly Val Pro Gly
            340                 345                 350

Val Gly Val Pro Gly Gly Gly Val Pro Gly Ala Gly Val Pro Gly Gly
        355                 360                 365
```

```
Gly Val Pro Gly Val Gly Val Pro Gly Val Gly Val Pro Gly Gly Gly
        370                 375                 380
Val Pro Gly Ala Gly Val Pro Gly Val Gly Val Pro Gly Val Gly Val
385                 390                 395                 400
Pro Gly Val Gly Val Pro Gly Gly Gly Val Pro Gly Ala Gly Val Pro
                405                 410                 415
Gly Gly Gly Val Pro Gly Val Gly Val Pro Gly Val Gly Val Pro Gly
            420                 425                 430
Gly Gly Val Pro Gly Ala Gly Val Pro Gly Val Gly Val Pro Gly Val
        435                 440                 445
Gly Val Pro Gly Val Gly Val Pro Gly Gly Gly Val Pro Gly Ala Gly
    450                 455                 460
Val Pro Gly Gly Gly Val Pro Gly Val Gly Val Pro Gly Val Gly Val
465                 470                 475                 480
Pro Gly Gly Gly Val Pro Gly Ala Gly Val Pro Gly Val Gly Val Pro
                485                 490                 495
Gly Val Gly Val Pro Gly Val Gly Val Pro Gly Gly Gly Val Pro Gly
            500                 505                 510
Ala Gly Val Pro Gly Gly Val Pro Gly Val Gly Val Pro Gly Val
        515                 520                 525
Gly Val Pro Gly Gly Gly Val Pro Gly Ala Gly Val Pro Gly Val Gly
        530                 535                 540
Val Pro Gly Val Gly Val Pro Gly Val Gly Val Pro Gly Gly Gly Val
545                 550                 555                 560
Pro Gly Ala Gly Val Pro Gly Gly Gly Val Pro Gly Val Gly Val Pro
                565                 570                 575
Gly Val Gly Val Pro Gly Gly Gly Val Pro Gly Ala Gly Val Pro Gly
            580                 585                 590
Val Gly Val Pro Gly Val Gly Val Pro Gly Val Gly Val Pro Gly Gly
        595                 600                 605
Gly Val Pro Gly Ala Gly Val Pro Gly Gly Gly Val Pro Gly Val Gly
        610                 615                 620
Val Pro Gly Val Gly Val Pro Gly Gly Gly Val Pro Gly Ala Gly Val
625                 630                 635                 640
Pro Gly Val Gly Val Pro Gly Gly Gly Val Pro Gly Val Gly Val Pro
                645                 650                 655
Gly Gly Gly Val Pro Gly Ala Gly Val Pro Gly Gly Gly Val Pro Gly
            660                 665                 670
Val Gly Val Pro Gly Val Gly Val Pro Gly Gly Gly Val Pro Gly Ala
        675                 680                 685
Gly Val Pro Gly Val Gly Val Pro Gly Val Gly Val Pro Gly Val Gly
        690                 695                 700
Val Pro Gly Gly Gly Val Pro Gly Ala Gly Val Pro Gly Gly Gly Val
705                 710                 715                 720
Pro Gly Val Gly Val Pro Gly Val Gly Val Pro Gly Gly Gly Val Pro
                725                 730                 735
Gly Ala Gly Val Pro Gly Val Gly Val Pro Gly Val Gly Val Pro Gly
            740                 745                 750
Val Gly Val Pro Gly Gly Gly Val Pro Gly Ala Gly Val Pro Gly Gly
        755                 760                 765
Gly Val Pro Gly Trp Pro
    770
```

<210> SEQ ID NO 26
<211> LENGTH: 824
<212> TYPE: PRT
<213> ORGANISM: Artificial Sequence
<220> FEATURE:
<223> OTHER INFORMATION: Antp-ELP2

<400> SEQUENCE: 26

```
Met Arg Gln Ile Lys Ile Trp Phe Gln Asn Arg Arg Met Lys Trp Lys
1               5                   10                  15

Lys Gly Cys Gly Pro Gly Val Gly Val Pro Gly Ala Gly Val Pro Gly
            20                  25                  30

Gly Gly Val Pro Gly Ala Gly Val Pro Gly Gly Gly Val Pro Gly Ala
        35                  40                  45

Gly Val Pro Gly Gly Gly Val Pro Gly Ala Gly Val Pro Gly Gly Gly
    50                  55                  60

Val Pro Gly Ala Gly Val Pro Gly Gly Gly Val Pro Gly Ala Gly Val
65                  70                  75                  80

Pro Gly Gly Gly Val Pro Gly Ala Gly Val Pro Gly Gly Gly Val Pro
                85                  90                  95

Gly Ala Gly Val Pro Gly Val Gly Val Pro Gly Ala Gly Val Pro Gly
            100                 105                 110

Gly Gly Val Pro Gly Ala Gly Val Pro Gly Gly Gly Val Pro Gly Ala
        115                 120                 125

Gly Val Pro Gly Gly Gly Val Pro Gly Ala Gly Val Pro Gly Gly Gly
    130                 135                 140

Val Pro Gly Ala Gly Val Pro Gly Gly Gly Val Pro Gly Ala Gly Val
145                 150                 155                 160

Pro Gly Gly Gly Val Pro Gly Ala Gly Val Pro Gly Gly Gly Val Pro
                165                 170                 175

Gly Ala Gly Val Pro Gly Val Gly Val Pro Gly Ala Gly Val Pro Gly
            180                 185                 190

Gly Gly Val Pro Gly Ala Gly Val Pro Gly Gly Gly Val Pro Gly Ala
        195                 200                 205

Gly Val Pro Gly Gly Gly Val Pro Gly Ala Gly Val Pro Gly Gly Gly
    210                 215                 220

Val Pro Gly Ala Gly Val Pro Gly Gly Gly Val Pro Gly Ala Gly Val
225                 230                 235                 240

Pro Gly Gly Gly Val Pro Gly Ala Gly Val Pro Gly Gly Gly Val Pro
                245                 250                 255

Gly Ala Gly Val Pro Gly Val Gly Val Pro Gly Ala Gly Val Pro Gly
            260                 265                 270

Gly Gly Val Pro Gly Ala Gly Val Pro Gly Gly Gly Val Pro Gly Ala
        275                 280                 285

Gly Val Pro Gly Gly Gly Val Pro Gly Ala Gly Val Pro Gly Gly Gly
    290                 295                 300

Val Pro Gly Ala Gly Val Pro Gly Gly Gly Val Pro Gly Ala Gly Val
305                 310                 315                 320

Pro Gly Gly Gly Val Pro Gly Ala Gly Val Pro Gly Gly Gly Val Pro
                325                 330                 335

Gly Ala Gly Val Pro Gly Val Gly Val Pro Gly Ala Gly Val Pro Gly
            340                 345                 350

Gly Gly Val Pro Gly Ala Gly Val Pro Gly Gly Gly Val Pro Gly Ala
        355                 360                 365
```

-continued

```
Gly Val Pro Gly Gly Gly Val Pro Gly Ala Gly Val Pro Gly Gly
    370                 375                 380
Val Pro Gly Ala Gly Val Pro Gly Gly Gly Val Pro Gly Ala Gly Val
385                 390                 395                 400
Pro Gly Gly Gly Val Pro Gly Ala Gly Val Pro Gly Gly Gly Val Pro
                405                 410                 415
Gly Ala Gly Val Pro Gly Val Gly Val Pro Gly Ala Gly Val Pro Gly
            420                 425                 430
Gly Gly Val Pro Gly Ala Gly Val Pro Gly Gly Gly Val Pro Gly Ala
        435                 440                 445
Gly Val Pro Gly Gly Gly Val Pro Gly Ala Gly Val Pro Gly Gly Gly
    450                 455                 460
Val Pro Gly Ala Gly Val Pro Gly Gly Gly Val Pro Gly Ala Gly Val
465                 470                 475                 480
Pro Gly Gly Gly Val Pro Gly Ala Gly Val Pro Gly Gly Gly Val Pro
                485                 490                 495
Gly Ala Gly Val Pro Gly Val Gly Val Pro Gly Ala Gly Val Pro Gly
            500                 505                 510
Gly Gly Val Pro Gly Ala Gly Val Pro Gly Gly Gly Val Pro Gly Ala
        515                 520                 525
Gly Val Pro Gly Gly Gly Val Pro Gly Ala Gly Val Pro Gly Gly Gly
    530                 535                 540
Val Pro Gly Ala Gly Val Pro Gly Gly Gly Val Pro Gly Ala Gly Val
545                 550                 555                 560
Pro Gly Gly Gly Val Pro Gly Ala Gly Val Pro Gly Gly Gly Val Pro
                565                 570                 575
Gly Ala Gly Val Pro Gly Val Gly Val Pro Gly Ala Gly Val Pro Gly
            580                 585                 590
Gly Gly Val Pro Gly Ala Gly Val Pro Gly Gly Gly Val Pro Gly Ala
        595                 600                 605
Gly Val Pro Gly Gly Gly Val Pro Gly Ala Gly Val Pro Gly Gly Gly
    610                 615                 620
Val Pro Gly Ala Gly Val Pro Gly Gly Gly Val Pro Gly Ala Gly Val
625                 630                 635                 640
Pro Gly Gly Gly Val Pro Gly Ala Gly Val Pro Gly Gly Gly Val Pro
                645                 650                 655
Gly Ala Gly Val Pro Gly Val Gly Val Pro Gly Ala Gly Val Pro Gly
            660                 665                 670
Gly Gly Val Pro Gly Ala Gly Val Pro Gly Gly Gly Val Pro Gly Ala
        675                 680                 685
Gly Val Pro Gly Gly Gly Val Pro Gly Ala Gly Val Pro Gly Gly Gly
    690                 695                 700
Val Pro Gly Ala Gly Val Pro Gly Gly Gly Val Pro Gly Ala Gly Val
705                 710                 715                 720
Pro Gly Gly Gly Val Pro Gly Ala Gly Val Pro Gly Gly Gly Val Pro
                725                 730                 735
Gly Ala Gly Val Pro Gly Val Gly Val Pro Gly Ala Gly Val Pro Gly
            740                 745                 750
Gly Gly Val Pro Gly Ala Gly Val Pro Gly Gly Gly Val Pro Gly Ala
        755                 760                 765
Gly Val Pro Gly Gly Gly Val Pro Gly Ala Gly Val Pro Gly Gly Gly
    770                 775                 780
Val Pro Gly Ala Gly Val Pro Gly Gly Gly Val Pro Gly Ala Gly Val
```

```
                   785                 790                795                800
              Pro Gly Gly Gly Val Pro Gly Ala Gly Val Pro Gly Gly Val Pro
                              805                 810                 815
              Gly Ala Gly Val Pro Gly Trp Pro
                              820

<210> SEQ ID NO 27
<211> LENGTH: 778
<212> TYPE: PRT
<213> ORGANISM: Artificial Sequence
<220> FEATURE:
<223> OTHER INFORMATION: MTS-ELP1

<400> SEQUENCE: 27

Met Ala Ala Val Ala Leu Leu Pro Ala Val Leu Leu Ala Leu Leu Ala
1               5                   10                  15

Pro Gly Gly Pro Gly Val Gly Val Pro Gly Val Gly Val Pro Gly Gly
                20                  25                  30

Gly Val Pro Gly Ala Gly Val Pro Gly Val Gly Val Pro Gly Val Gly
                35                  40                  45

Val Pro Gly Val Gly Val Pro Gly Gly Val Pro Gly Ala Gly Val
50                  55                  60

Pro Gly Gly Gly Val Pro Gly Val Gly Val Pro Gly Val Gly Val Pro
65                  70                  75                  80

Gly Gly Gly Val Pro Gly Ala Gly Val Pro Gly Val Gly Val Pro Gly
                85                  90                  95

Val Gly Val Pro Gly Val Gly Val Pro Gly Gly Val Pro Gly Ala
                100                 105                 110

Gly Val Pro Gly Gly Val Pro Gly Val Gly Val Pro Gly Val Gly
                115                 120                 125

Val Pro Gly Gly Gly Val Pro Gly Ala Gly Val Pro Gly Val Gly Val
                130                 135                 140

Pro Gly Val Gly Val Pro Gly Val Gly Val Pro Gly Gly Gly Val Pro
145                 150                 155                 160

Gly Ala Gly Val Pro Gly Gly Val Pro Gly Val Gly Val Pro Gly
                165                 170                 175

Val Gly Val Pro Gly Gly Gly Val Pro Gly Ala Gly Val Pro Gly Val
                180                 185                 190

Gly Val Pro Gly Val Gly Val Pro Gly Val Gly Val Pro Gly Gly Gly
                195                 200                 205

Val Pro Gly Ala Gly Val Pro Gly Gly Val Pro Gly Val Gly Val
                210                 215                 220

Pro Gly Val Gly Val Pro Gly Gly Gly Val Pro Gly Ala Gly Val Pro
225                 230                 235                 240

Gly Val Gly Val Pro Gly Val Gly Val Pro Gly Val Gly Val Pro Gly
                245                 250                 255

Gly Gly Val Pro Gly Ala Gly Val Pro Gly Gly Gly Val Pro Gly Val
                260                 265                 270

Gly Val Pro Gly Val Gly Val Pro Gly Gly Gly Val Pro Gly Ala Gly
                275                 280                 285

Val Pro Gly Val Gly Val Pro Gly Val Gly Val Pro Gly Val Gly Val
                290                 295                 300

Pro Gly Gly Gly Val Pro Gly Ala Gly Val Pro Gly Gly Gly Val Pro
305                 310                 315                 320

Gly Val Gly Val Pro Gly Val Gly Val Pro Gly Gly Gly Val Pro Gly
```

```
                      325                 330                 335
Ala Gly Val Pro Gly Val Gly Val Pro Gly Val Gly Val Pro Gly Val
                340                 345                 350
Gly Val Pro Gly Gly Gly Val Pro Gly Ala Gly Val Pro Gly Gly Gly
                355                 360                 365
Val Pro Gly Val Gly Val Pro Gly Val Gly Val Pro Gly Gly Gly Val
                370                 375                 380
Pro Gly Ala Gly Val Pro Gly Val Gly Val Pro Gly Val Gly Val Pro
385                 390                 395                 400
Gly Val Gly Val Pro Gly Gly Gly Val Pro Gly Ala Gly Val Pro Gly
                405                 410                 415
Gly Gly Val Pro Gly Val Gly Val Pro Gly Val Gly Val Pro Gly Gly
                420                 425                 430
Gly Val Pro Gly Ala Gly Val Pro Gly Val Gly Val Pro Gly Val Gly
                435                 440                 445
Val Pro Gly Val Gly Val Pro Gly Gly Gly Val Pro Gly Ala Gly Val
                450                 455                 460
Pro Gly Gly Gly Val Pro Gly Val Gly Val Pro Gly Val Gly Val Pro
465                 470                 475                 480
Gly Gly Gly Val Pro Gly Ala Gly Val Pro Gly Val Gly Val Pro Gly
                485                 490                 495
Val Gly Val Pro Gly Val Gly Val Pro Gly Gly Gly Val Pro Gly Ala
                500                 505                 510
Gly Val Pro Gly Gly Gly Val Pro Gly Val Gly Val Pro Gly Val Gly
                515                 520                 525
Val Pro Gly Gly Gly Val Pro Gly Ala Gly Val Pro Gly Val Gly Val
                530                 535                 540
Pro Gly Val Gly Val Pro Gly Val Gly Val Pro Gly Gly Gly Val Pro
545                 550                 555                 560
Gly Ala Gly Val Pro Gly Gly Gly Val Pro Gly Val Gly Val Pro Gly
                565                 570                 575
Val Gly Val Pro Gly Gly Gly Val Pro Gly Ala Gly Val Pro Gly Val
                580                 585                 590
Gly Val Pro Gly Val Gly Val Pro Gly Val Gly Val Pro Gly Gly Gly
                595                 600                 605
Val Pro Gly Ala Gly Val Pro Gly Gly Gly Val Pro Gly Val Gly Val
                610                 615                 620
Pro Gly Val Gly Val Pro Gly Gly Gly Val Pro Gly Ala Gly Val Pro
625                 630                 635                 640
Gly Val Gly Val Pro Gly Val Gly Val Pro Gly Val Gly Val Pro Gly
                645                 650                 655
Gly Gly Val Pro Gly Ala Gly Val Pro Gly Gly Gly Val Pro Gly Val
                660                 665                 670
Gly Val Pro Gly Val Gly Val Pro Gly Gly Gly Val Pro Gly Ala Gly
                675                 680                 685
Val Pro Gly Val Gly Val Pro Gly Val Gly Val Pro Gly Val Gly Val
                690                 695                 700
Pro Gly Gly Gly Val Pro Gly Ala Gly Val Pro Gly Gly Gly Val Pro
705                 710                 715                 720
Gly Val Gly Val Pro Gly Val Gly Val Pro Gly Gly Gly Val Pro Gly
                725                 730                 735
Ala Gly Val Pro Gly Val Gly Val Pro Gly Val Gly Val Pro Gly Val
                740                 745                 750
```

Gly Val Pro Gly Gly Val Pro Gly Ala Gly Val Pro Gly Gly
        755                 760                 765

Val Pro Gly Trp Pro Gly Ser Gly Gly Cys
    770                 775

<210> SEQ ID NO 28
<211> LENGTH: 828
<212> TYPE: PRT
<213> ORGANISM: Artificial Sequence
<220> FEATURE:
<223> OTHER INFORMATION: MTS-ELP2

<400> SEQUENCE: 28

Met Ala Ala Val Ala Leu Leu Pro Ala Val Leu Leu Ala Leu Leu Ala
1               5                   10                  15

Pro Gly Gly Pro Gly Val Gly Val Pro Gly Ala Gly Val Pro Gly Gly
            20                  25                  30

Gly Val Pro Gly Ala Gly Val Pro Gly Gly Gly Val Pro Gly Ala Gly
        35                  40                  45

Val Pro Gly Gly Gly Val Pro Gly Ala Gly Val Pro Gly Gly Gly Val
    50                  55                  60

Pro Gly Ala Gly Val Pro Gly Gly Gly Val Pro Gly Ala Gly Val Pro
65                  70                  75                  80

Gly Gly Gly Val Pro Gly Ala Gly Val Pro Gly Gly Gly Val Pro Gly
                85                  90                  95

Ala Gly Val Pro Gly Gly Gly Val Pro Gly Ala Gly Val Pro Gly Gly
            100                 105                 110

Gly Val Pro Gly Ala Gly Val Pro Gly Gly Gly Val Pro Gly Ala Gly
        115                 120                 125

Val Pro Gly Gly Gly Val Pro Gly Ala Gly Val Pro Gly Gly Gly Val
    130                 135                 140

Pro Gly Ala Gly Val Pro Gly Gly Gly Val Pro Gly Ala Gly Val Pro
145                 150                 155                 160

Gly Gly Gly Val Pro Gly Ala Gly Val Pro Gly Gly Gly Val Pro Gly
                165                 170                 175

Ala Gly Val Pro Gly Gly Gly Val Pro Gly Ala Gly Val Pro Gly Gly
            180                 185                 190

Gly Val Pro Gly Ala Gly Val Pro Gly Gly Gly Val Pro Gly Ala Gly
        195                 200                 205

Val Pro Gly Gly Gly Val Pro Gly Ala Gly Val Pro Gly Gly Gly Val
    210                 215                 220

Pro Gly Ala Gly Val Pro Gly Gly Gly Val Pro Gly Ala Gly Val Pro
225                 230                 235                 240

Gly Gly Gly Val Pro Gly Ala Gly Val Pro Gly Gly Gly Val Pro Gly
                245                 250                 255

Ala Gly Val Pro Gly Gly Gly Val Pro Gly Ala Gly Val Pro Gly Gly
            260                 265                 270

Gly Val Pro Gly Ala Gly Val Pro Gly Gly Gly Val Pro Gly Ala Gly
        275                 280                 285

Val Pro Gly Gly Gly Val Pro Gly Ala Gly Val Pro Gly Gly Gly Val
    290                 295                 300

Pro Gly Ala Gly Val Pro Gly Gly Gly Val Pro Gly Ala Gly Val Pro
305                 310                 315                 320

Gly Gly Gly Val Pro Gly Ala Gly Val Pro Gly Gly Gly Val Pro Gly
                325                 330                 335

```
Ala Gly Val Pro Gly Val Gly Val Pro Gly Ala Gly Val Pro Gly Gly
            340                 345                 350

Gly Val Pro Gly Ala Gly Val Pro Gly Gly Gly Val Pro Gly Ala Gly
            355                 360                 365

Val Pro Gly Gly Val Pro Gly Ala Gly Val Pro Gly Gly Gly Val
370                 375                 380

Pro Gly Ala Gly Val Pro Gly Gly Gly Val Pro Gly Ala Gly Val Pro
385                 390                 395                 400

Gly Gly Gly Val Pro Gly Ala Gly Val Pro Gly Gly Gly Val Pro Gly
            405                 410                 415

Ala Gly Val Pro Gly Val Gly Val Pro Gly Ala Gly Val Pro Gly Gly
            420                 425                 430

Gly Val Pro Gly Ala Gly Val Pro Gly Gly Gly Val Pro Gly Ala Gly
            435                 440                 445

Val Pro Gly Gly Gly Val Pro Gly Ala Gly Val Pro Gly Gly Gly Val
            450                 455                 460

Pro Gly Ala Gly Val Pro Gly Gly Gly Val Pro Gly Ala Gly Val Pro
465                 470                 475                 480

Gly Gly Gly Val Pro Gly Ala Gly Val Pro Gly Gly Gly Val Pro Gly
            485                 490                 495

Ala Gly Val Pro Gly Val Gly Val Pro Gly Ala Gly Val Pro Gly Gly
            500                 505                 510

Gly Val Pro Gly Ala Gly Val Pro Gly Gly Gly Val Pro Gly Ala Gly
            515                 520                 525

Val Pro Gly Gly Gly Val Pro Gly Ala Gly Val Pro Gly Gly Gly Val
            530                 535                 540

Pro Gly Ala Gly Val Pro Gly Gly Gly Val Pro Gly Ala Gly Val Pro
545                 550                 555                 560

Gly Gly Gly Val Pro Gly Ala Gly Val Pro Gly Gly Gly Val Pro Gly
            565                 570                 575

Ala Gly Val Pro Gly Val Gly Val Pro Gly Ala Gly Val Pro Gly Gly
            580                 585                 590

Gly Val Pro Gly Ala Gly Val Pro Gly Gly Gly Val Pro Gly Ala Gly
            595                 600                 605

Val Pro Gly Gly Val Pro Gly Ala Gly Val Pro Gly Gly Gly Val
            610                 615                 620

Pro Gly Ala Gly Val Pro Gly Gly Gly Val Pro Gly Ala Gly Val Pro
625                 630                 635                 640

Gly Gly Gly Val Pro Gly Ala Gly Val Pro Gly Gly Gly Val Pro Gly
            645                 650                 655

Ala Gly Val Pro Gly Val Gly Val Pro Gly Ala Gly Val Pro Gly Gly
            660                 665                 670

Gly Val Pro Gly Ala Gly Val Pro Gly Gly Gly Val Pro Gly Ala Gly
            675                 680                 685

Val Pro Gly Gly Gly Val Pro Gly Ala Gly Val Pro Gly Gly Gly Val
            690                 695                 700

Pro Gly Ala Gly Val Pro Gly Gly Gly Val Pro Gly Ala Gly Val Pro
705                 710                 715                 720

Gly Gly Gly Val Pro Gly Ala Gly Val Pro Gly Gly Gly Val Pro Gly
            725                 730                 735

Ala Gly Val Pro Gly Val Gly Val Pro Gly Ala Gly Val Pro Gly Gly
            740                 745                 750
```

```
Gly Val Pro Gly Ala Gly Val Pro Gly Gly Val Pro Gly Ala Gly
            755                 760                 765

Val Pro Gly Gly Val Pro Gly Ala Gly Val Pro Gly Gly Val
            770                 775                 780

Pro Gly Ala Gly Val Pro Gly Gly Val Pro Gly Ala Gly Val Pro
785                 790                 795                 800

Gly Gly Val Pro Gly Ala Gly Val Pro Gly Gly Val Pro Gly
            805                 810                 815

Ala Gly Val Pro Gly Trp Pro Gly Ser Gly Gly Cys
            820                 825

<210> SEQ ID NO 29
<211> LENGTH: 786
<212> TYPE: PRT
<213> ORGANISM: Artificial Sequence
<220> FEATURE:
<223> OTHER INFORMATION: Bac-7-ELP1

<400> SEQUENCE: 29

Met Arg Arg Ile Arg Pro Arg Pro Pro Arg Leu Pro Arg Pro Arg Pro
1               5                   10                  15

Arg Pro Leu Pro Phe Pro Arg Pro Gly Gly Pro Gly Val Gly Val
            20                  25                  30

Pro Gly Val Gly Val Pro Gly Gly Val Pro Gly Ala Gly Val Pro
            35                  40                  45

Gly Val Gly Val Pro Gly Val Gly Val Pro Gly Val Gly Val Pro Gly
    50                  55                  60

Gly Gly Val Pro Gly Ala Gly Val Pro Gly Gly Val Pro Gly Val
65                  70                  75                  80

Gly Val Pro Gly Val Gly Val Pro Gly Gly Val Pro Gly Ala Gly
            85                  90                  95

Val Pro Gly Val Gly Val Pro Gly Val Gly Val Pro Gly Val Gly Val
            100                 105                 110

Pro Gly Gly Gly Val Pro Gly Ala Gly Val Pro Gly Gly Val Pro
            115                 120                 125

Gly Val Gly Val Pro Gly Val Gly Val Pro Gly Gly Val Pro Gly
            130                 135                 140

Ala Gly Val Pro Gly Val Gly Val Pro Gly Val Gly Val Pro Gly Val
145                 150                 155                 160

Gly Val Pro Gly Gly Val Pro Gly Ala Gly Val Pro Gly Gly Gly
                165                 170                 175

Val Pro Gly Val Gly Val Pro Gly Val Gly Val Pro Gly Gly Val
            180                 185                 190

Pro Gly Ala Gly Val Pro Gly Val Gly Val Pro Gly Val Gly Val Pro
            195                 200                 205

Gly Val Gly Val Pro Gly Gly Gly Val Pro Gly Ala Gly Val Pro Gly
            210                 215                 220

Gly Gly Val Pro Gly Val Gly Val Pro Gly Val Gly Val Pro Gly Gly
225                 230                 235                 240

Gly Val Pro Gly Ala Gly Val Pro Gly Val Gly Val Pro Gly Val Gly
                245                 250                 255

Val Pro Gly Val Gly Val Pro Gly Gly Gly Val Pro Gly Ala Gly Val
            260                 265                 270

Pro Gly Gly Gly Val Pro Gly Val Gly Val Pro Gly Val Gly Val Pro
            275                 280                 285
```

```
Gly Gly Gly Val Pro Gly Ala Gly Val Pro Gly Val Gly Val Pro Gly
            290                 295                 300
Val Gly Val Pro Gly Val Gly Val Pro Gly Gly Val Pro Gly Val Gly Val Pro Gly Ala
305                 310                 315                 320
Gly Val Pro Gly Gly Val Pro Gly Val Gly Val Pro Gly Val Gly
                325                 330                 335
Val Pro Gly Gly Gly Val Pro Gly Ala Gly Val Pro Gly Val Gly Val
            340                 345                 350
Pro Gly Val Gly Val Pro Gly Val Gly Val Pro Gly Gly Gly Val Pro
            355                 360                 365
Gly Ala Gly Val Pro Gly Gly Val Pro Gly Val Gly Val Pro Gly
370                 375                 380
Val Gly Val Pro Gly Gly Gly Val Pro Gly Ala Gly Val Pro Gly Val
385                 390                 395                 400
Gly Val Pro Gly Val Gly Val Pro Gly Val Gly Val Pro Gly Gly Gly
                405                 410                 415
Val Pro Gly Ala Gly Val Pro Gly Gly Gly Val Pro Gly Val Gly Val
            420                 425                 430
Pro Gly Val Gly Val Pro Gly Gly Gly Val Pro Gly Ala Gly Val Pro
            435                 440                 445
Gly Val Gly Val Pro Gly Val Gly Val Pro Gly Val Gly Val Pro Gly
            450                 455                 460
Gly Gly Val Pro Gly Ala Gly Val Pro Gly Gly Gly Val Pro Gly Val
465                 470                 475                 480
Gly Val Pro Gly Val Gly Val Pro Gly Gly Gly Val Pro Gly Ala Gly
                485                 490                 495
Val Pro Gly Val Gly Val Pro Gly Val Gly Val Pro Gly Val Gly Val
            500                 505                 510
Pro Gly Gly Gly Val Pro Gly Ala Gly Val Pro Gly Gly Gly Val Pro
            515                 520                 525
Gly Val Gly Val Pro Gly Val Gly Val Pro Gly Gly Gly Val Pro Gly
            530                 535                 540
Ala Gly Val Pro Gly Val Gly Val Pro Gly Val Gly Val Pro Gly Val
545                 550                 555                 560
Gly Val Pro Gly Gly Gly Val Pro Gly Ala Gly Val Pro Gly Gly Gly
                565                 570                 575
Val Pro Gly Val Gly Val Pro Gly Val Gly Val Pro Gly Gly Gly Val
            580                 585                 590
Pro Gly Ala Gly Val Pro Gly Val Gly Val Pro Gly Val Gly Val Pro
            595                 600                 605
Gly Val Gly Val Pro Gly Gly Gly Val Pro Gly Ala Gly Val Pro Gly
            610                 615                 620
Gly Gly Val Pro Gly Val Gly Val Pro Gly Val Gly Val Pro Gly Gly
625                 630                 635                 640
Gly Val Pro Gly Ala Gly Val Pro Gly Val Gly Val Pro Gly Val Gly
                645                 650                 655
Val Pro Gly Val Gly Val Pro Gly Gly Gly Val Pro Gly Ala Gly Val
            660                 665                 670
Pro Gly Gly Gly Val Pro Gly Val Gly Val Pro Gly Val Gly Val Pro
            675                 680                 685
Gly Gly Gly Val Pro Gly Ala Gly Val Pro Gly Val Gly Val Pro Gly
            690                 695                 700
Val Gly Val Pro Gly Val Gly Val Pro Gly Gly Gly Val Pro Gly Ala
```

```
                705                 710                 715                 720
Gly Val Pro Gly Gly Val Pro Gly Val Pro Gly Val Gly
                    725                 730                 735
Val Pro Gly Gly Gly Val Pro Gly Ala Gly Val Pro Gly Val Gly Val
                    740                 745                 750
Pro Gly Val Gly Val Pro Gly Val Gly Val Pro Gly Gly Gly Val Pro
                    755                 760                 765
Gly Ala Gly Val Pro Gly Gly Val Pro Gly Trp Pro Gly Ser Gly
            770                 775                 780
Gly Cys
785

<210> SEQ ID NO 30
<211> LENGTH: 836
<212> TYPE: PRT
<213> ORGANISM: Artificial Sequence
<220> FEATURE:
<223> OTHER INFORMATION: Bac-7-ELP2

<400> SEQUENCE: 30

Met Arg Arg Ile Arg Pro Arg Pro Pro Arg Leu Pro Arg Pro Arg Pro
1               5                   10                  15
Arg Pro Leu Pro Phe Pro Arg Pro Gly Gly Pro Gly Val Gly Val
                20                  25                  30
Pro Gly Ala Gly Val Pro Gly Gly Val Pro Gly Ala Gly Val Pro
            35                  40                  45
Gly Gly Gly Val Pro Gly Ala Gly Val Pro Gly Gly Gly Val Pro Gly
50                  55                  60
Ala Gly Val Pro Gly Gly Gly Val Pro Gly Ala Gly Val Pro Gly Gly
65                  70                  75                  80
Gly Val Pro Gly Ala Gly Val Pro Gly Gly Gly Val Pro Gly Ala Gly
                85                  90                  95
Val Pro Gly Gly Gly Val Pro Gly Ala Gly Val Pro Gly Val Gly Val
                100                 105                 110
Pro Gly Ala Gly Val Pro Gly Gly Gly Val Pro Gly Ala Gly Val Pro
                115                 120                 125
Gly Gly Gly Val Pro Gly Ala Gly Val Pro Gly Gly Gly Val Pro Gly
            130                 135                 140
Ala Gly Val Pro Gly Gly Gly Val Pro Gly Ala Gly Val Pro Gly Gly
145                 150                 155                 160
Gly Val Pro Gly Ala Gly Val Pro Gly Gly Gly Val Pro Gly Ala Gly
                165                 170                 175
Val Pro Gly Gly Gly Val Pro Gly Ala Gly Val Pro Gly Val Gly Val
            180                 185                 190
Pro Gly Ala Gly Val Pro Gly Gly Gly Val Pro Gly Ala Gly Val Pro
            195                 200                 205
Gly Gly Gly Val Pro Gly Ala Gly Val Pro Gly Gly Gly Val Pro Gly
            210                 215                 220
Ala Gly Val Pro Gly Gly Gly Val Pro Gly Ala Gly Val Pro Gly Gly
225                 230                 235                 240
Gly Val Pro Gly Ala Gly Val Pro Gly Gly Gly Val Pro Gly Ala Gly
                245                 250                 255
Val Pro Gly Gly Gly Val Pro Gly Ala Gly Val Pro Gly Val Gly Val
            260                 265                 270
Pro Gly Ala Gly Val Pro Gly Gly Gly Val Pro Gly Ala Gly Val Pro
```

```
                275                 280                 285
Gly Gly Gly Val Pro Gly Ala Gly Val Pro Gly Gly Gly Val Pro Gly
    290                 295                 300
Ala Gly Val Pro Gly Gly Gly Val Pro Gly Ala Gly Val Pro Gly Gly
305                 310                 315                 320
Gly Val Pro Gly Ala Gly Val Pro Gly Gly Gly Val Pro Gly Ala Gly
                325                 330                 335
Val Pro Gly Gly Gly Val Pro Gly Ala Gly Val Pro Gly Val Gly Val
            340                 345                 350
Pro Gly Ala Gly Val Pro Gly Gly Gly Val Pro Gly Ala Gly Val Pro
        355                 360                 365
Gly Gly Gly Val Pro Gly Ala Gly Val Pro Gly Gly Gly Val Pro Gly
    370                 375                 380
Ala Gly Val Pro Gly Gly Gly Val Pro Gly Ala Gly Val Pro Gly Gly
385                 390                 395                 400
Gly Val Pro Gly Ala Gly Val Pro Gly Gly Gly Val Pro Gly Ala Gly
                405                 410                 415
Val Pro Gly Gly Gly Val Pro Gly Ala Gly Val Pro Gly Val Gly Val
            420                 425                 430
Pro Gly Ala Gly Val Pro Gly Gly Gly Val Pro Gly Ala Gly Val Pro
        435                 440                 445
Gly Gly Gly Val Pro Gly Ala Gly Val Pro Gly Gly Gly Val Pro Gly
    450                 455                 460
Ala Gly Val Pro Gly Gly Gly Val Pro Gly Ala Gly Val Pro Gly Gly
465                 470                 475                 480
Gly Val Pro Gly Ala Gly Val Pro Gly Gly Gly Val Pro Gly Ala Gly
                485                 490                 495
Val Pro Gly Gly Gly Val Pro Gly Ala Gly Val Pro Gly Val Gly Val
            500                 505                 510
Pro Gly Ala Gly Val Pro Gly Gly Gly Val Pro Gly Ala Gly Val Pro
        515                 520                 525
Gly Gly Gly Val Pro Gly Ala Gly Val Pro Gly Gly Gly Val Pro Gly
    530                 535                 540
Ala Gly Val Pro Gly Gly Gly Val Pro Gly Ala Gly Val Pro Gly Gly
545                 550                 555                 560
Gly Val Pro Gly Ala Gly Val Pro Gly Gly Gly Val Pro Gly Ala Gly
                565                 570                 575
Val Pro Gly Gly Gly Val Pro Gly Ala Gly Val Pro Gly Val Gly Val
            580                 585                 590
Pro Gly Ala Gly Val Pro Gly Gly Gly Val Pro Gly Ala Gly Val Pro
        595                 600                 605
Gly Gly Gly Val Pro Gly Ala Gly Val Pro Gly Gly Gly Val Pro Gly
    610                 615                 620
Ala Gly Val Pro Gly Gly Gly Val Pro Gly Ala Gly Val Pro Gly Gly
625                 630                 635                 640
Gly Val Pro Gly Ala Gly Val Pro Gly Gly Gly Val Pro Gly Ala Gly
                645                 650                 655
Val Pro Gly Gly Gly Val Pro Gly Ala Gly Val Pro Gly Val Gly Val
            660                 665                 670
Pro Gly Ala Gly Val Pro Gly Gly Gly Val Pro Gly Ala Gly Val Pro
        675                 680                 685
Gly Gly Gly Val Pro Gly Ala Gly Val Pro Gly Gly Gly Val Pro Gly
    690                 695                 700
```

```
Ala Gly Val Pro Gly Gly Val Pro Gly Ala Val Pro Gly Gly
705                 710                 715                 720

Gly Val Pro Gly Ala Gly Val Pro Gly Gly Val Pro Gly Ala Gly
                725                 730                 735

Val Pro Gly Gly Gly Val Pro Gly Ala Gly Val Pro Gly Val Gly Val
            740                 745                 750

Pro Gly Ala Gly Val Pro Gly Gly Val Pro Gly Ala Gly Val Pro
                755                 760                 765

Gly Gly Gly Val Pro Gly Ala Gly Val Pro Gly Gly Val Pro Gly
        770                 775                 780

Ala Gly Val Pro Gly Gly Val Pro Gly Ala Gly Val Pro Gly Gly
785                 790                 795                 800

Gly Val Pro Gly Ala Gly Val Pro Gly Gly Val Pro Gly Ala Gly
                805                 810                 815

Val Pro Gly Gly Gly Val Pro Gly Ala Gly Val Pro Gly Trp Pro Gly
            820                 825                 830

Ser Gly Gly Cys
        835

<210> SEQ ID NO 31
<211> LENGTH: 789
<212> TYPE: PRT
<213> ORGANISM: Artificial Sequence
<220> FEATURE:
<223> OTHER INFORMATION: Trans-ELP1

<400> SEQUENCE: 31

Met Gly Trp Thr Leu Asn Ser Ala Gly Tyr Leu Leu Gly Lys Ile Asn
1               5                   10                  15

Leu Lys Ala Leu Ala Ala Leu Ala Lys Lys Ile Leu Gly Gly Pro Gly
                20                  25                  30

Val Gly Val Pro Gly Val Gly Val Pro Gly Gly Gly Val Pro Gly Ala
                35                  40                  45

Gly Val Pro Gly Val Gly Val Pro Gly Val Gly Val Pro Gly Val Gly
            50                  55                  60

Val Pro Gly Gly Gly Val Pro Gly Ala Gly Val Pro Gly Gly Gly Val
65                  70                  75                  80

Pro Gly Val Gly Val Pro Gly Val Gly Val Pro Gly Gly Gly Val Pro
                85                  90                  95

Gly Ala Gly Val Pro Gly Val Gly Val Pro Gly Val Gly Val Pro Gly
            100                 105                 110

Val Gly Val Pro Gly Gly Gly Val Pro Gly Ala Gly Val Pro Gly Gly
        115                 120                 125

Gly Val Pro Gly Val Gly Val Pro Gly Val Gly Val Pro Gly Gly Gly
    130                 135                 140

Val Pro Gly Ala Gly Val Pro Gly Val Gly Val Pro Gly Val Gly Val
145                 150                 155                 160

Pro Gly Val Gly Val Pro Gly Gly Gly Val Pro Gly Ala Gly Val Pro
                165                 170                 175

Gly Gly Gly Val Pro Gly Val Gly Val Pro Gly Val Gly Val Pro Gly
            180                 185                 190

Gly Gly Val Pro Gly Ala Gly Val Pro Gly Gly Val Pro Gly Val
        195                 200                 205

Gly Val Pro Gly Val Gly Val Pro Gly Gly Gly Val Pro Gly Ala Gly
    210                 215                 220
```

-continued

Val Pro Gly Gly Gly Val Pro Gly Val Gly Val Pro Gly Val Gly Val
225                 230                 235                 240

Pro Gly Gly Gly Val Pro Gly Ala Gly Val Pro Gly Val Gly Val Pro
                245                 250                 255

Gly Val Gly Val Pro Gly Val Gly Val Pro Gly Gly Gly Val Pro Gly
            260                 265                 270

Ala Gly Val Pro Gly Val Gly Val Pro Gly Val Gly Val Pro Gly Val
        275                 280                 285

Gly Val Pro Gly Gly Gly Val Pro Gly Ala Gly Val Pro Gly Val Gly
    290                 295                 300

Val Pro Gly Val Gly Val Pro Gly Val Gly Val Pro Gly Gly Gly Val
305                 310                 315                 320

Pro Gly Ala Gly Val Pro Gly Gly Val Pro Gly Val Gly Val Pro
                325                 330                 335

Gly Val Gly Val Pro Gly Gly Gly Val Pro Gly Ala Gly Val Pro Gly
            340                 345                 350

Val Gly Val Pro Gly Val Gly Val Pro Gly Val Gly Val Pro Gly Gly
        355                 360                 365

Gly Val Pro Gly Ala Gly Val Pro Gly Gly Val Pro Gly Val Gly
    370                 375                 380

Val Pro Gly Val Gly Val Pro Gly Gly Gly Val Pro Gly Ala Gly Val
385                 390                 395                 400

Pro Gly Val Gly Val Pro Gly Val Gly Val Pro Gly Val Gly Val Pro
                405                 410                 415

Gly Gly Gly Val Pro Gly Ala Gly Val Pro Gly Gly Gly Val Pro Gly
            420                 425                 430

Val Gly Val Pro Gly Val Gly Val Pro Gly Gly Gly Val Pro Gly Ala
        435                 440                 445

Gly Val Pro Gly Val Gly Val Pro Gly Val Gly Val Pro Gly Val Gly
    450                 455                 460

Val Pro Gly Gly Gly Val Pro Gly Ala Gly Val Pro Gly Gly Gly Val
465                 470                 475                 480

Pro Gly Val Gly Val Pro Gly Val Gly Val Pro Gly Gly Gly Val Pro
                485                 490                 495

Gly Ala Gly Val Pro Gly Val Gly Val Pro Gly Val Gly Val Pro Gly
            500                 505                 510

Val Gly Val Pro Gly Gly Gly Val Pro Gly Ala Gly Val Pro Gly Gly
        515                 520                 525

Gly Val Pro Gly Val Gly Val Pro Gly Val Gly Val Pro Gly Gly Gly
    530                 535                 540

Val Pro Gly Ala Gly Val Pro Gly Val Gly Val Pro Gly Val Gly Val
545                 550                 555                 560

Pro Gly Val Gly Val Pro Gly Gly Gly Val Pro Gly Ala Gly Val Pro
                565                 570                 575

Gly Gly Gly Val Pro Gly Val Gly Val Pro Gly Val Gly Val Pro Gly
            580                 585                 590

Gly Gly Val Pro Gly Ala Gly Val Pro Gly Val Gly Val Pro Gly Val
            595                 600                 605

Gly Val Pro Gly Val Gly Val Pro Gly Gly Gly Val Pro Gly Ala Gly
    610                 615                 620

Val Pro Gly Gly Gly Val Pro Gly Val Gly Val Pro Gly Val Gly Val
625                 630                 635                 640

Pro Gly Gly Gly Val Pro Gly Ala Gly Val Pro Gly Val Gly Val Pro
                    645                 650                 655

Gly Val Gly Val Pro Gly Val Gly Val Pro Gly Gly Gly Val Pro Gly
            660                 665                 670

Ala Gly Val Pro Gly Gly Gly Val Pro Gly Val Gly Val Pro Gly Val
            675                 680                 685

Gly Val Pro Gly Gly Gly Val Pro Gly Ala Gly Val Pro Gly Val Gly
            690                 695                 700

Val Pro Gly Val Gly Val Pro Gly Val Gly Val Pro Gly Gly Gly Val
705                 710                 715                 720

Pro Gly Ala Gly Val Pro Gly Gly Gly Val Pro Gly Val Gly Val Pro
            725                 730                 735

Gly Val Gly Val Pro Gly Gly Gly Val Pro Gly Ala Gly Val Pro Gly
            740                 745                 750

Val Gly Val Pro Gly Gly Gly Val Pro Gly Val Gly Val Pro Gly Gly
            755                 760                 765

Gly Val Pro Gly Ala Gly Val Pro Gly Gly Gly Val Pro Gly Trp Pro
            770                 775                 780

Gly Ser Gly Gly Cys
785

<210> SEQ ID NO 32
<211> LENGTH: 839
<212> TYPE: PRT
<213> ORGANISM: Artificial Sequence
<220> FEATURE:
<223> OTHER INFORMATION: Trans-ELP2

<400> SEQUENCE: 32

Met Gly Trp Thr Leu Asn Ser Ala Gly Tyr Leu Leu Gly Lys Ile Asn
1               5                   10                  15

Leu Lys Ala Leu Ala Ala Leu Ala Lys Lys Ile Leu Gly Gly Pro Gly
            20                  25                  30

Val Gly Val Pro Gly Ala Gly Val Pro Gly Gly Gly Val Pro Gly Ala
            35                  40                  45

Gly Val Pro Gly Gly Gly Val Pro Gly Ala Gly Val Pro Gly Gly Gly
        50                  55                  60

Val Pro Gly Ala Gly Val Pro Gly Gly Gly Val Pro Gly Ala Gly Val
65                  70                  75                  80

Pro Gly Gly Gly Val Pro Gly Ala Gly Val Pro Gly Gly Gly Val Pro
                85                  90                  95

Gly Ala Gly Val Pro Gly Gly Gly Val Pro Gly Ala Gly Val Pro Gly
            100                 105                 110

Val Gly Val Pro Gly Ala Gly Val Pro Gly Gly Gly Val Pro Gly Ala
            115                 120                 125

Gly Val Pro Gly Gly Gly Val Pro Gly Ala Gly Val Pro Gly Gly Gly
            130                 135                 140

Val Pro Gly Ala Gly Val Pro Gly Gly Gly Val Pro Gly Ala Gly Val
145                 150                 155                 160

Pro Gly Gly Gly Val Pro Gly Ala Gly Val Pro Gly Gly Gly Val Pro
                165                 170                 175

Gly Ala Gly Val Pro Gly Gly Gly Val Pro Gly Ala Gly Val Pro Gly
            180                 185                 190

Val Gly Val Pro Gly Ala Gly Val Pro Gly Gly Gly Val Pro Gly Ala
            195                 200                 205

```
Gly Val Pro Gly Gly Gly Val Pro Gly Ala Gly Val Pro Gly Gly Gly
    210                 215                 220
Val Pro Gly Ala Gly Val Pro Gly Gly Gly Val Pro Gly Ala Gly Val
225                 230                 235                 240
Pro Gly Gly Gly Val Pro Gly Ala Gly Val Pro Gly Gly Gly Val Pro
                245                 250                 255
Gly Ala Gly Val Pro Gly Gly Gly Val Pro Gly Ala Gly Val Pro Gly
            260                 265                 270
Val Gly Val Pro Gly Ala Gly Val Pro Gly Gly Gly Val Pro Gly Ala
        275                 280                 285
Gly Val Pro Gly Gly Gly Val Pro Gly Ala Gly Val Pro Gly Gly Gly
    290                 295                 300
Val Pro Gly Ala Gly Val Pro Gly Gly Gly Val Pro Gly Ala Gly Val
305                 310                 315                 320
Pro Gly Gly Gly Val Pro Gly Ala Gly Val Pro Gly Gly Gly Val Pro
                325                 330                 335
Gly Ala Gly Val Pro Gly Gly Gly Val Pro Gly Ala Gly Val Pro Gly
            340                 345                 350
Val Gly Val Pro Gly Ala Gly Val Pro Gly Gly Gly Val Pro Gly Ala
        355                 360                 365
Gly Val Pro Gly Gly Gly Val Pro Gly Ala Gly Val Pro Gly Gly Gly
    370                 375                 380
Val Pro Gly Ala Gly Val Pro Gly Gly Gly Val Pro Gly Ala Gly Val
385                 390                 395                 400
Pro Gly Gly Gly Val Pro Gly Ala Gly Val Pro Gly Gly Gly Val Pro
                405                 410                 415
Gly Ala Gly Val Pro Gly Gly Gly Val Pro Gly Ala Gly Val Pro Gly
            420                 425                 430
Val Gly Val Pro Gly Ala Gly Val Pro Gly Gly Gly Val Pro Gly Ala
        435                 440                 445
Gly Val Pro Gly Gly Gly Val Pro Gly Ala Gly Val Pro Gly Gly Gly
    450                 455                 460
Val Pro Gly Ala Gly Val Pro Gly Gly Gly Val Pro Gly Ala Gly Val
465                 470                 475                 480
Pro Gly Gly Gly Val Pro Gly Ala Gly Val Pro Gly Gly Gly Val Pro
                485                 490                 495
Gly Ala Gly Val Pro Gly Gly Gly Val Pro Gly Ala Gly Val Pro Gly
            500                 505                 510
Val Gly Val Pro Gly Ala Gly Val Pro Gly Gly Gly Val Pro Gly Ala
        515                 520                 525
Gly Val Pro Gly Gly Gly Val Pro Gly Ala Gly Val Pro Gly Gly Gly
    530                 535                 540
Val Pro Gly Ala Gly Val Pro Gly Gly Gly Val Pro Gly Ala Gly Val
545                 550                 555                 560
Pro Gly Gly Gly Val Pro Gly Ala Gly Val Pro Gly Gly Gly Val Pro
                565                 570                 575
Gly Ala Gly Val Pro Gly Gly Gly Val Pro Gly Ala Gly Val Pro Gly
            580                 585                 590
Val Gly Val Pro Gly Ala Gly Val Pro Gly Gly Gly Val Pro Gly Ala
        595                 600                 605
Gly Val Pro Gly Gly Gly Val Pro Gly Ala Gly Val Pro Gly Gly Gly
    610                 615                 620
Val Pro Gly Ala Gly Val Pro Gly Gly Gly Val Pro Gly Ala Gly Val
```

```
                625                 630                 635                 640
    Pro Gly Gly Gly Val Pro Gly Ala Gly Val Pro Gly Gly Val Pro
                        645                 650                 655
    Gly Ala Gly Val Pro Gly Gly Val Pro Gly Ala Gly Val Pro Gly
                        660                 665                 670
    Val Gly Val Pro Gly Ala Gly Val Pro Gly Gly Val Pro Gly Ala
                        675                 680                 685
    Gly Val Pro Gly Gly Val Pro Gly Ala Gly Val Pro Gly Gly Gly
                        690                 695                 700
    Val Pro Gly Ala Gly Val Pro Gly Gly Val Pro Gly Ala Gly Val
    705                 710                 715                 720
    Pro Gly Gly Gly Val Pro Gly Ala Gly Val Pro Gly Gly Val Pro
                        725                 730                 735
    Gly Ala Gly Val Pro Gly Gly Val Pro Gly Ala Gly Val Pro Gly
                        740                 745                 750
    Val Gly Val Pro Gly Ala Gly Val Pro Gly Gly Val Pro Gly Ala
                        755                 760                 765
    Gly Val Pro Gly Gly Val Pro Gly Ala Gly Val Pro Gly Gly Gly
                        770                 775                 780
    Val Pro Gly Ala Gly Val Pro Gly Gly Val Pro Gly Ala Gly Val
    785                 790                 795                 800
    Pro Gly Gly Gly Val Pro Gly Ala Gly Val Pro Gly Gly Val Pro
                        805                 810                 815
    Gly Ala Gly Val Pro Gly Gly Val Pro Gly Ala Gly Val Pro Gly
                        820                 825                 830

Trp Pro Gly Ser Gly Gly Cys
                        835

<210> SEQ ID NO 33
<211> LENGTH: 780
<212> TYPE: PRT
<213> ORGANISM: Artificial Sequence
<220> FEATURE:
<223> OTHER INFORMATION: pVEC-ELP1

<400> SEQUENCE: 33

Met Leu Leu Ile Ile Leu Arg Arg Arg Ile Arg Lys Gln Ala His Ala
1               5                   10                  15

His Ser Lys Gly Gly Pro Gly Val Gly Val Pro Gly Val Gly Val Pro
                20                  25                  30

Gly Gly Gly Val Pro Gly Ala Gly Val Pro Gly Val Gly Val Pro Gly
            35                  40                  45

Val Gly Val Pro Gly Val Gly Val Pro Gly Gly Gly Val Pro Gly Ala
        50                  55                  60

Gly Val Pro Gly Gly Gly Val Pro Gly Val Gly Val Pro Gly Val Gly
65                  70                  75                  80

Val Pro Gly Gly Gly Val Pro Gly Ala Gly Val Pro Gly Val Gly Val
                85                  90                  95

Pro Gly Val Gly Val Pro Gly Val Gly Val Pro Gly Gly Gly Val Pro
            100                 105                 110

Gly Ala Gly Val Pro Gly Gly Gly Val Pro Gly Val Gly Val Pro Gly
        115                 120                 125

Val Gly Val Pro Gly Gly Gly Val Pro Gly Ala Gly Val Pro Gly Val
    130                 135                 140

Gly Val Pro Gly Val Gly Val Pro Gly Val Gly Val Pro Gly Gly Gly
```

```
            145                 150                 155                 160
Val Pro Gly Ala Gly Val Pro Gly Gly Val Pro Gly Val Gly Val
                165                 170                 175
Pro Gly Val Gly Val Pro Gly Gly Val Pro Gly Ala Gly Val Pro
            180                 185                 190
Gly Val Gly Val Pro Gly Val Gly Val Pro Gly Val Gly Val Pro Gly
        195                 200                 205
Gly Gly Val Pro Gly Ala Gly Val Pro Gly Gly Val Pro Gly Val
    210                 215                 220
Gly Val Pro Gly Val Gly Val Pro Gly Gly Val Pro Gly Ala Gly
225                 230                 235                 240
Val Pro Gly Val Gly Val Pro Gly Val Gly Val Pro Gly Val Gly Val
                245                 250                 255
Pro Gly Gly Gly Val Pro Gly Ala Gly Val Pro Gly Gly Val Pro
            260                 265                 270
Gly Val Gly Val Pro Gly Val Gly Val Pro Gly Gly Val Pro Gly
        275                 280                 285
Ala Gly Val Pro Gly Val Gly Val Pro Gly Val Gly Val Pro Gly Val
    290                 295                 300
Gly Val Pro Gly Gly Val Pro Gly Ala Gly Val Pro Gly Gly Gly
305                 310                 315                 320
Val Pro Gly Val Gly Val Pro Gly Val Gly Val Pro Gly Gly Val
                325                 330                 335
Pro Gly Ala Gly Val Pro Gly Val Gly Val Pro Gly Val Gly Val Pro
            340                 345                 350
Gly Val Gly Val Pro Gly Gly Val Pro Gly Ala Gly Val Pro Gly
        355                 360                 365
Gly Gly Val Pro Gly Val Gly Val Pro Gly Val Gly Val Pro Gly Gly
    370                 375                 380
Gly Val Pro Gly Ala Gly Val Pro Gly Val Gly Val Pro Gly Val Gly
385                 390                 395                 400
Val Pro Gly Val Gly Val Pro Gly Gly Val Pro Gly Ala Gly Val
                405                 410                 415
Pro Gly Gly Gly Val Pro Gly Val Gly Val Pro Gly Val Gly Val Pro
            420                 425                 430
Gly Gly Gly Val Pro Gly Ala Gly Val Pro Gly Val Gly Val Pro Gly
        435                 440                 445
Val Gly Val Pro Gly Val Gly Val Pro Gly Gly Val Pro Gly Ala
    450                 455                 460
Gly Val Pro Gly Gly Gly Val Pro Gly Val Gly Val Pro Gly Val Gly
465                 470                 475                 480
Val Pro Gly Gly Gly Val Pro Gly Ala Gly Val Pro Gly Val Gly Val
                485                 490                 495
Pro Gly Val Gly Val Pro Gly Val Gly Val Pro Gly Gly Gly Val Pro
            500                 505                 510
Gly Ala Gly Val Pro Gly Gly Gly Val Pro Gly Val Gly Val Pro Gly
        515                 520                 525
Val Gly Val Pro Gly Gly Gly Val Pro Gly Ala Gly Val Pro Gly Val
    530                 535                 540
Gly Val Pro Gly Val Gly Val Pro Gly Val Gly Val Pro Gly Gly Gly
545                 550                 555                 560
Val Pro Gly Ala Gly Val Pro Gly Gly Gly Val Pro Gly Val Gly Val
                565                 570                 575
```

-continued

```
Pro Gly Val Gly Val Pro Gly Gly Val Pro Gly Ala Gly Val Pro
            580                 585                 590

Gly Val Gly Val Pro Gly Val Gly Val Pro Gly Val Gly Val Pro Gly
        595                 600                 605

Gly Gly Val Pro Gly Ala Gly Val Pro Gly Gly Val Pro Gly Val
610                 615                 620

Gly Val Pro Gly Val Gly Val Pro Gly Gly Val Pro Gly Ala Gly
625                 630                 635                 640

Val Pro Gly Val Gly Val Pro Gly Val Gly Val Pro Gly Val Gly Val
            645                 650                 655

Pro Gly Gly Val Pro Gly Ala Gly Val Pro Gly Gly Val Pro
        660                 665                 670

Gly Val Gly Val Pro Gly Val Gly Val Pro Gly Gly Val Pro Gly
        675                 680                 685

Ala Gly Val Pro Gly Val Gly Val Pro Gly Val Gly Val Pro Gly Val
690                 695                 700

Gly Val Pro Gly Gly Val Pro Gly Ala Gly Val Pro Gly Gly Gly
705                 710                 715                 720

Val Pro Gly Val Gly Val Pro Gly Val Gly Val Pro Gly Gly Val
            725                 730                 735

Pro Gly Ala Gly Val Pro Gly Val Gly Val Pro Gly Val Gly Val Pro
        740                 745                 750

Gly Val Gly Val Pro Gly Gly Val Pro Gly Ala Gly Val Pro Gly
        755                 760                 765

Gly Gly Val Pro Gly Trp Pro Gly Ser Gly Gly Cys
770                 775                 780

<210> SEQ ID NO 34
<211> LENGTH: 830
<212> TYPE: PRT
<213> ORGANISM: Artificial Sequence
<220> FEATURE:
<223> OTHER INFORMATION: pVEC-ELP2

<400> SEQUENCE: 34

Met Leu Leu Ile Ile Leu Arg Arg Arg Ile Arg Lys Gln Ala His Ala
1               5                   10                  15

His Ser Lys Gly Gly Pro Gly Val Gly Val Pro Gly Ala Gly Val Pro
            20                  25                  30

Gly Gly Gly Val Pro Gly Ala Gly Val Pro Gly Gly Gly Val Pro Gly
        35                  40                  45

Ala Gly Val Pro Gly Gly Val Pro Gly Ala Gly Val Pro Gly Gly
    50                  55                  60

Gly Val Pro Gly Ala Gly Val Pro Gly Gly Val Pro Gly Ala Gly
65                  70                  75                  80

Val Pro Gly Gly Val Pro Gly Ala Gly Val Pro Gly Gly Gly Val
            85                  90                  95

Pro Gly Ala Gly Val Pro Gly Val Gly Val Pro Gly Ala Gly Val Pro
        100                 105                 110

Gly Gly Gly Val Pro Gly Ala Gly Val Pro Gly Gly Val Pro Gly
        115                 120                 125

Ala Gly Val Pro Gly Gly Val Pro Gly Ala Gly Val Pro Gly Gly
    130                 135                 140

Gly Val Pro Gly Ala Gly Val Pro Gly Gly Gly Val Pro Gly Ala Gly
145                 150                 155                 160
```

Val Pro Gly Gly Gly Val Pro Gly Ala Gly Val Pro Gly Gly Gly Val
            165                 170                 175

Pro Gly Ala Gly Val Pro Gly Val Gly Val Pro Gly Ala Gly Val Pro
            180                 185                 190

Gly Gly Gly Val Pro Gly Ala Gly Val Pro Gly Gly Gly Val Pro Gly
            195                 200                 205

Ala Gly Val Pro Gly Gly Val Pro Gly Ala Gly Val Pro Gly Gly
            210                 215                 220

Gly Val Pro Gly Ala Gly Val Pro Gly Gly Gly Val Pro Gly Ala Gly
225                 230                 235                 240

Val Pro Gly Gly Gly Val Pro Gly Ala Gly Val Pro Gly Gly Gly Val
            245                 250                 255

Pro Gly Ala Gly Val Pro Gly Val Gly Val Pro Gly Ala Gly Val Pro
            260                 265                 270

Gly Gly Gly Val Pro Gly Ala Gly Val Pro Gly Gly Gly Val Pro Gly
            275                 280                 285

Ala Gly Val Pro Gly Gly Gly Val Pro Gly Ala Gly Val Pro Gly Gly
            290                 295                 300

Gly Val Pro Gly Ala Gly Val Pro Gly Gly Gly Val Pro Gly Ala Gly
305                 310                 315                 320

Val Pro Gly Gly Gly Val Pro Gly Ala Gly Val Pro Gly Gly Gly Val
            325                 330                 335

Pro Gly Ala Gly Val Pro Gly Val Gly Val Pro Gly Ala Gly Val Pro
            340                 345                 350

Gly Gly Gly Val Pro Gly Ala Gly Val Pro Gly Gly Gly Val Pro Gly
            355                 360                 365

Ala Gly Val Pro Gly Gly Gly Val Pro Gly Ala Gly Val Pro Gly Gly
            370                 375                 380

Gly Val Pro Gly Ala Gly Val Pro Gly Gly Gly Val Pro Gly Ala Gly
385                 390                 395                 400

Val Pro Gly Gly Gly Val Pro Gly Ala Gly Val Pro Gly Gly Gly Val
            405                 410                 415

Pro Gly Ala Gly Val Pro Gly Val Gly Val Pro Gly Ala Gly Val Pro
            420                 425                 430

Gly Gly Gly Val Pro Gly Ala Gly Val Pro Gly Gly Gly Val Pro Gly
            435                 440                 445

Ala Gly Val Pro Gly Gly Gly Val Pro Gly Ala Gly Val Pro Gly Gly
            450                 455                 460

Gly Val Pro Gly Ala Gly Val Pro Gly Gly Gly Val Pro Gly Ala Gly
465                 470                 475                 480

Val Pro Gly Gly Gly Val Pro Gly Ala Gly Val Pro Gly Gly Gly Val
            485                 490                 495

Pro Gly Ala Gly Val Pro Gly Val Gly Val Pro Gly Ala Gly Val Pro
            500                 505                 510

Gly Gly Gly Val Pro Gly Ala Gly Val Pro Gly Gly Gly Val Pro Gly
            515                 520                 525

Ala Gly Val Pro Gly Gly Gly Val Pro Gly Ala Gly Val Pro Gly Gly
            530                 535                 540

Gly Val Pro Gly Ala Gly Val Pro Gly Gly Gly Val Pro Gly Ala Gly
545                 550                 555                 560

Val Pro Gly Gly Gly Val Pro Gly Ala Gly Val Pro Gly Gly Gly Val
            565                 570                 575

Pro Gly Ala Gly Val Pro Gly Val Pro Gly Ala Gly Val Pro
                580                 585                 590

Gly Gly Gly Val Pro Gly Ala Gly Val Pro Gly Gly Gly Val Pro Gly
            595                 600                 605

Ala Gly Val Pro Gly Gly Val Pro Gly Ala Gly Val Pro Gly Gly
    610                 615                 620

Gly Val Pro Gly Ala Gly Val Pro Gly Gly Val Pro Gly Ala Gly
625                 630                 635                 640

Val Pro Gly Gly Gly Val Pro Gly Ala Gly Val Pro Gly Gly Val
                645                 650                 655

Pro Gly Ala Gly Val Pro Gly Gly Val Pro Gly Ala Gly Val Pro
            660                 665                 670

Gly Gly Gly Val Pro Gly Ala Gly Val Pro Gly Gly Gly Val Pro Gly
                675                 680                 685

Ala Gly Val Pro Gly Gly Val Pro Gly Ala Gly Val Pro Gly Gly
    690                 695                 700

Gly Val Pro Gly Ala Gly Val Pro Gly Gly Val Pro Gly Ala Gly
705                 710                 715                 720

Val Pro Gly Gly Gly Val Pro Gly Ala Gly Val Pro Gly Gly Val
                725                 730                 735

Pro Gly Ala Gly Val Pro Gly Val Pro Gly Ala Gly Val Pro
            740                 745                 750

Gly Gly Gly Val Pro Gly Ala Gly Val Pro Gly Gly Val Pro Gly
                755                 760                 765

Ala Gly Val Pro Gly Gly Val Pro Gly Ala Gly Val Pro Gly Gly
    770                 775                 780

Gly Val Pro Gly Ala Gly Val Pro Gly Gly Val Pro Gly Ala Gly
785                 790                 795                 800

Val Pro Gly Gly Gly Val Pro Gly Ala Gly Val Pro Gly Gly Val
                805                 810                 815

Pro Gly Ala Gly Val Pro Gly Trp Pro Gly Ser Gly Gly Cys
            820                 825                 830

<210> SEQ ID NO 35
<211> LENGTH: 780
<212> TYPE: PRT
<213> ORGANISM: Artificial Sequence
<220> FEATURE:
<223> OTHER INFORMATION: SynB1-ELP1

<400> SEQUENCE: 35

Met Arg Gly Gly Arg Leu Ser Tyr Ser Arg Arg Phe Ser Thr Ser
1               5                   10                  15

Thr Gly Arg Gly Gly Pro Gly Val Gly Val Pro Gly Val Gly Val Pro
            20                  25                  30

Gly Gly Gly Val Pro Gly Ala Gly Val Pro Gly Val Gly Val Pro Gly
            35                  40                  45

Val Gly Val Pro Gly Val Gly Val Pro Gly Gly Val Pro Gly Ala
    50                  55                  60

Gly Val Pro Gly Gly Val Pro Gly Val Gly Val Pro Gly Val Gly
65                  70                  75                  80

Val Pro Gly Gly Gly Val Pro Gly Ala Gly Val Pro Gly Val Gly Val
                85                  90                  95

Pro Gly Val Gly Val Pro Gly Val Gly Val Pro Gly Gly Gly Val Pro
            100                 105                 110

-continued

```
Gly Ala Gly Val Pro Gly Gly Val Pro Gly Val Gly Val Pro Gly
            115                 120                 125
Val Gly Val Pro Gly Gly Val Pro Gly Ala Gly Val Pro Gly Val
            130                 135                 140
Gly Val Pro Gly Val Gly Val Pro Gly Val Gly Val Pro Gly Gly
145                 150                 155                 160
Val Pro Gly Ala Gly Val Pro Gly Gly Val Pro Gly Val Gly Val
                165                 170                 175
Pro Gly Val Gly Val Pro Gly Gly Val Pro Gly Ala Gly Val Pro
            180                 185                 190
Gly Val Gly Val Pro Gly Val Gly Val Pro Gly Val Gly Val Pro Gly
            195                 200                 205
Gly Gly Val Pro Gly Ala Gly Val Pro Gly Gly Val Pro Gly Val
210                 215                 220
Gly Val Pro Gly Val Gly Val Pro Gly Gly Val Pro Gly Ala Gly
225                 230                 235                 240
Val Pro Gly Val Gly Val Pro Gly Val Gly Val Pro Gly Val Gly Val
                245                 250                 255
Pro Gly Gly Gly Val Pro Gly Ala Gly Val Pro Gly Gly Gly Val Pro
            260                 265                 270
Gly Val Gly Val Pro Gly Val Gly Val Pro Gly Gly Gly Val Pro Gly
            275                 280                 285
Ala Gly Val Pro Gly Val Gly Val Pro Gly Val Gly Val Pro Gly Val
            290                 295                 300
Gly Val Pro Gly Gly Gly Val Pro Gly Ala Gly Val Pro Gly Gly Gly
305                 310                 315                 320
Val Pro Gly Val Gly Val Pro Gly Val Gly Val Pro Gly Gly Gly Val
                325                 330                 335
Pro Gly Ala Gly Val Pro Gly Gly Val Pro Gly Val Gly Val Pro
            340                 345                 350
Gly Val Gly Val Pro Gly Gly Gly Val Pro Gly Ala Gly Val Pro Gly
            355                 360                 365
Gly Gly Val Pro Gly Val Gly Val Pro Gly Val Gly Val Pro Gly Gly
            370                 375                 380
Gly Val Pro Gly Ala Gly Val Pro Gly Gly Val Pro Gly Val Gly
385                 390                 395                 400
Val Pro Gly Val Gly Val Pro Gly Gly Gly Val Pro Gly Ala Gly Val
                405                 410                 415
Pro Gly Gly Gly Val Pro Gly Val Gly Val Pro Gly Val Gly Val Pro
            420                 425                 430
Gly Gly Gly Val Pro Gly Ala Gly Val Pro Gly Val Gly Val Pro Gly
            435                 440                 445
Val Gly Val Pro Gly Val Gly Val Pro Gly Gly Gly Val Pro Gly Ala
            450                 455                 460
Gly Val Pro Gly Gly Gly Val Pro Gly Val Gly Val Pro Gly Val Gly
465                 470                 475                 480
Val Pro Gly Gly Gly Val Pro Gly Ala Gly Val Pro Gly Val Gly Val
                485                 490                 495
Pro Gly Val Gly Val Pro Gly Val Gly Val Pro Gly Gly Gly Val Pro
            500                 505                 510
Gly Ala Gly Val Pro Gly Gly Gly Val Pro Gly Val Gly Val Pro Gly
            515                 520                 525
Val Gly Val Pro Gly Gly Gly Val Pro Gly Ala Gly Val Pro Gly Val
```

```
                530                 535                 540
Gly Val Pro Gly Val Gly Val Pro Gly Val Gly Val Pro Gly Gly
545                 550                 555                 560

Val Pro Gly Ala Gly Val Pro Gly Gly Val Pro Gly Val Gly Val
                565                 570                 575

Pro Gly Val Gly Val Pro Gly Gly Val Pro Gly Ala Gly Val Pro
                580                 585                 590

Gly Val Gly Val Pro Gly Val Gly Val Pro Gly Val Gly Val Pro Gly
                595                 600                 605

Gly Gly Val Pro Gly Ala Gly Val Pro Gly Gly Val Pro Gly Val
            610                 615                 620

Gly Val Pro Gly Val Gly Val Pro Gly Gly Val Pro Gly Ala Gly
625                 630                 635                 640

Val Pro Gly Val Gly Val Pro Gly Val Gly Val Pro Gly Val Gly Val
                645                 650                 655

Pro Gly Gly Gly Val Pro Gly Ala Gly Val Pro Gly Gly Gly Val Pro
                660                 665                 670

Gly Val Gly Val Pro Gly Val Gly Val Pro Gly Gly Gly Val Pro Gly
                675                 680                 685

Ala Gly Val Pro Gly Val Gly Val Pro Gly Val Gly Val Pro Gly Val
            690                 695                 700

Gly Val Pro Gly Gly Val Pro Gly Ala Gly Val Pro Gly Gly Gly
705                 710                 715                 720

Val Pro Gly Val Gly Val Pro Gly Val Gly Val Pro Gly Gly Gly Val
                725                 730                 735

Pro Gly Ala Gly Val Pro Gly Gly Val Pro Gly Val Gly Val Pro
            740                 745                 750

Gly Val Gly Val Pro Gly Gly Val Pro Gly Ala Gly Val Pro Gly
            755                 760                 765

Gly Gly Val Pro Gly Trp Pro Gly Ser Gly Gly Cys
    770                 775                 780

<210> SEQ ID NO 36
<211> LENGTH: 830
<212> TYPE: PRT
<213> ORGANISM: Artificial Sequence
<220> FEATURE:
<223> OTHER INFORMATION: SynB2-ELP2

<400> SEQUENCE: 36

Met Arg Gly Gly Arg Leu Ser Tyr Ser Arg Arg Phe Ser Thr Ser
1               5                   10                  15

Thr Gly Arg Gly Gly Pro Gly Val Gly Val Pro Gly Ala Gly Val Pro
                20                  25                  30

Gly Gly Gly Val Pro Gly Ala Gly Val Pro Gly Gly Val Pro Gly
            35                  40                  45

Ala Gly Val Pro Gly Gly Val Pro Gly Ala Gly Val Pro Gly Gly
        50                  55                  60

Gly Val Pro Gly Ala Gly Val Pro Gly Gly Val Pro Gly Ala Gly
65                  70                  75                  80

Val Pro Gly Gly Val Pro Gly Ala Gly Val Pro Gly Gly Gly Val
                85                  90                  95

Pro Gly Ala Gly Val Pro Gly Gly Val Pro Gly Ala Gly Val Pro
                100                 105                 110

Gly Gly Gly Val Pro Gly Ala Gly Val Pro Gly Gly Gly Val Pro Gly
```

```
              115                 120                 125
Ala Gly Val Pro Gly Gly Val Pro Gly Ala Gly Val Pro Gly Gly
            130                 135                 140
Gly Val Pro Gly Ala Gly Val Pro Gly Gly Gly Val Pro Gly Ala Gly
145                 150                 155                 160
Val Pro Gly Gly Gly Val Pro Gly Ala Gly Val Pro Gly Gly Gly Val
                165                 170                 175
Pro Gly Ala Gly Val Pro Gly Val Gly Val Pro Gly Ala Gly Val Pro
            180                 185                 190
Gly Gly Gly Val Pro Gly Ala Gly Val Pro Gly Gly Gly Val Pro Gly
            195                 200                 205
Ala Gly Val Pro Gly Gly Gly Val Pro Gly Ala Gly Val Pro Gly Gly
            210                 215                 220
Gly Val Pro Gly Ala Gly Val Pro Gly Gly Gly Val Pro Gly Ala Gly
225                 230                 235                 240
Val Pro Gly Gly Gly Val Pro Gly Ala Gly Val Pro Gly Gly Gly Val
                245                 250                 255
Pro Gly Ala Gly Val Pro Gly Val Gly Val Pro Gly Ala Gly Val Pro
            260                 265                 270
Gly Gly Gly Val Pro Gly Ala Gly Val Pro Gly Gly Gly Val Pro Gly
            275                 280                 285
Ala Gly Val Pro Gly Gly Gly Val Pro Gly Ala Gly Val Pro Gly Gly
            290                 295                 300
Gly Val Pro Gly Ala Gly Val Pro Gly Gly Gly Val Pro Gly Ala Gly
305                 310                 315                 320
Val Pro Gly Gly Gly Val Pro Gly Ala Gly Val Pro Gly Gly Gly Val
                325                 330                 335
Pro Gly Ala Gly Val Pro Gly Val Gly Val Pro Gly Ala Gly Val Pro
            340                 345                 350
Gly Gly Gly Val Pro Gly Ala Gly Val Pro Gly Gly Gly Val Pro Gly
            355                 360                 365
Ala Gly Val Pro Gly Gly Gly Val Pro Gly Ala Gly Val Pro Gly Gly
            370                 375                 380
Gly Val Pro Gly Ala Gly Val Pro Gly Gly Gly Val Pro Gly Ala Gly
385                 390                 395                 400
Val Pro Gly Gly Gly Val Pro Gly Ala Gly Val Pro Gly Gly Gly Val
                405                 410                 415
Pro Gly Ala Gly Val Pro Gly Gly Gly Val Pro Gly Ala Gly Val Pro
            420                 425                 430
Gly Gly Gly Val Pro Gly Ala Gly Val Pro Gly Gly Gly Val Pro Gly
            435                 440                 445
Ala Gly Val Pro Gly Gly Gly Val Pro Gly Ala Gly Val Pro Gly Gly
            450                 455                 460
Gly Val Pro Gly Ala Gly Val Pro Gly Gly Gly Val Pro Gly Ala Gly
465                 470                 475                 480
Val Pro Gly Gly Gly Val Pro Gly Ala Gly Val Pro Gly Gly Gly Val
                485                 490                 495
Pro Gly Ala Gly Val Pro Gly Val Gly Val Pro Gly Ala Gly Val Pro
            500                 505                 510
Gly Gly Gly Val Pro Gly Ala Gly Val Pro Gly Gly Gly Val Pro Gly
            515                 520                 525
Ala Gly Val Pro Gly Gly Gly Val Pro Gly Ala Gly Val Pro Gly Gly
            530                 535                 540
```

```
Gly Val Pro Gly Ala Gly Val Pro Gly Gly Val Pro Gly Ala Gly
545                 550                 555                 560
Val Pro Gly Gly Gly Val Pro Gly Ala Gly Val Pro Gly Gly Gly Val
                565                 570                 575
Pro Gly Ala Gly Val Pro Gly Val Gly Val Pro Gly Ala Gly Val Pro
            580                 585                 590
Gly Gly Gly Val Pro Gly Ala Gly Val Pro Gly Gly Gly Val Pro Gly
        595                 600                 605
Ala Gly Val Pro Gly Gly Val Pro Gly Ala Gly Val Pro Gly Gly
    610                 615                 620
Gly Val Pro Gly Ala Gly Val Pro Gly Gly Val Pro Gly Ala Gly
625                 630                 635                 640
Val Pro Gly Gly Gly Val Pro Gly Ala Gly Val Pro Gly Gly Gly Val
                645                 650                 655
Pro Gly Ala Gly Val Pro Gly Val Gly Val Pro Gly Ala Gly Val Pro
            660                 665                 670
Gly Gly Gly Val Pro Gly Ala Gly Val Pro Gly Gly Gly Val Pro Gly
        675                 680                 685
Ala Gly Val Pro Gly Gly Val Pro Gly Ala Gly Val Pro Gly Gly
    690                 695                 700
Gly Val Pro Gly Ala Gly Val Pro Gly Gly Val Pro Gly Ala Gly
705                 710                 715                 720
Val Pro Gly Gly Gly Val Pro Gly Ala Gly Val Pro Gly Gly Gly Val
                725                 730                 735
Pro Gly Ala Gly Val Pro Gly Val Gly Val Pro Gly Ala Gly Val Pro
            740                 745                 750
Gly Gly Gly Val Pro Gly Ala Gly Val Pro Gly Gly Gly Val Pro Gly
        755                 760                 765
Ala Gly Val Pro Gly Gly Val Pro Gly Ala Gly Val Pro Gly Gly
    770                 775                 780
Gly Val Pro Gly Ala Gly Val Pro Gly Gly Val Pro Gly Ala Gly
785                 790                 795                 800
Val Pro Gly Gly Gly Val Pro Gly Ala Gly Val Pro Gly Gly Gly Val
                805                 810                 815
Pro Gly Ala Gly Val Pro Gly Trp Pro Gly Ser Gly Gly Cys
            820                 825                 830

<210> SEQ ID NO 37
<211> LENGTH: 14
<212> TYPE: PRT
<213> ORGANISM: Artificial Sequence
<220> FEATURE:
<223> OTHER INFORMATION: H1 TP

<400> SEQUENCE: 37

Asn Glu Leu Lys Arg Ala Phe Ala Ala Leu Arg Asp Gln Ile
1               5                   10

<210> SEQ ID NO 38
<211> LENGTH: 26
<212> TYPE: PRT
<213> ORGANISM: Artificial Sequence
<220> FEATURE:
<223> OTHER INFORMATION: p21 TP

<400> SEQUENCE: 38

Gly Arg Lys Arg Arg Gln Thr Ser Met Thr Asp Phe Tyr His Ser Lys
```

```
                1               5                  10                  15
Arg Arg Leu Ile Phe Ser Lys Arg Lys Pro
                20                  25

<210> SEQ ID NO 39
<211> LENGTH: 14
<212> TYPE: PRT
<213> ORGANISM: Artificial Sequence
<220> FEATURE:
<223> OTHER INFORMATION: KLAK TP

<400> SEQUENCE: 39

Lys Leu Ala Lys Leu Ala Lys Lys Leu Ala Lys Leu Ala Lys
1               5                   10

<210> SEQ ID NO 40
<211> LENGTH: 10
<212> TYPE: PRT
<213> ORGANISM: Artificial Sequence
<220> FEATURE:
<223> OTHER INFORMATION: p50 TP

<400> SEQUENCE: 40

Val Gln Arg Lys Arg Gln Lys Leu Met Pro
1               5                   10

<210> SEQ ID NO 41
<211> LENGTH: 9
<212> TYPE: PRT
<213> ORGANISM: Artificial Sequence
<220> FEATURE:
<223> OTHER INFORMATION: GGC3

<400> SEQUENCE: 41

Gly Gly Cys Gly Gly Cys Gly Gly Cys
1               5

<210> SEQ ID NO 42
<211> LENGTH: 5
<212> TYPE: PRT
<213> ORGANISM: Artificial Sequence
<220> FEATURE:
<223> OTHER INFORMATION: Elastin-like polypeptide variant
<220> FEATURE:
<221> NAME/KEY: X
<222> LOCATION: (4)..(4)
<223> OTHER INFORMATION: X is equal to valine, glycine, or alanine

<400> SEQUENCE: 42

Val Pro Gly Xaa Gly
1               5

<210> SEQ ID NO 43
<211> LENGTH: 8
<212> TYPE: PRT
<213> ORGANISM: Artificial Sequence
<220> FEATURE:
<223> OTHER INFORMATION: Sequence Motif QTSMTDFY

<400> SEQUENCE: 43

Gln Thr Ser Met Thr Asp Phe Tyr
1               5

<210> SEQ ID NO 44
<211> LENGTH: 1750
<212> TYPE: PRT
<213> ORGANISM: Artificial Sequence
```

-continued

```
<220> FEATURE:
<223> OTHER INFORMATION: Elastin-like polypeptide variant
<220> FEATURE:
<221> NAME/KEY: X
<222> LOCATION: (1)..(1750)
<223> OTHER INFORMATION: X is equal to valine, glycine, or alanine.  The
      sequence includes 350 repeating units of the amino acid sequence
      VPGXG, i.e., n=350; however, this unit can be repeated such that n
      is an integer from about 5 to about 350.

<400> SEQUENCE: 44

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
    130                 135                 140

Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
                165                 170                 175

Pro Gly Xaa Gly Val Pro Gly Xaa Gly Val Pro Gly Xaa Gly Val Pro
            180                 185                 190

Gly Xaa Gly Val Pro Gly Xaa Gly Val Pro Gly Xaa Gly Val Pro Gly
        195                 200                 205

Xaa Gly Val Pro Gly Xaa Gly Val Pro Gly Xaa Gly Val Pro Gly Xaa
    210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
                245                 250                 255

Pro Gly Xaa Gly Val Pro Gly Xaa Gly Val Pro Gly Xaa Gly Val Pro
            260                 265                 270

Gly Xaa Gly Val Pro Gly Xaa Gly Val Pro Gly Xaa Gly Val Pro Gly
        275                 280                 285

Xaa Gly Val Pro Gly Xaa Gly Val Pro Gly Xaa Gly Val Pro Gly Xaa
    290                 295                 300

Gly Val Pro Gly Xaa Gly Val Pro Gly Xaa Gly Val Pro Gly Xaa Gly
305                 310                 315                 320

Val Pro Gly Xaa Gly Val Pro Gly Xaa Gly Val Pro Gly Xaa Gly Val
                325                 330                 335

Pro Gly Xaa Gly Val Pro Gly Xaa Gly Val Pro Gly Xaa Gly Val Pro
            340                 345                 350

Gly Xaa Gly Val Pro Gly Xaa Gly Val Pro Gly Xaa Gly Val Pro Gly
```

```
                355                 360                 365
Xaa Gly Val Pro Gly Xaa Gly Val Pro Gly Xaa Gly Val Pro Gly Xaa
    370                 375                 380
Gly Val Pro Gly Xaa Gly Val Pro Gly Xaa Gly Val Pro Gly Xaa Gly
385                 390                 395                 400
Val Pro Gly Xaa Gly Val Pro Gly Xaa Gly Val Pro Gly Xaa Gly Val
                405                 410                 415
Pro Gly Xaa Gly Val Pro Gly Xaa Gly Val Pro Gly Xaa Gly Val Pro
            420                 425                 430
Gly Xaa Gly Val Pro Gly Xaa Gly Val Pro Gly Xaa Gly Val Pro Gly
        435                 440                 445
Xaa Gly Val Pro Gly Xaa Gly Val Pro Gly Xaa Gly Val Pro Gly Xaa
    450                 455                 460
Gly Val Pro Gly Xaa Gly Val Pro Gly Xaa Gly Val Pro Gly Xaa Gly
465                 470                 475                 480
Val Pro Gly Xaa Gly Val Pro Gly Xaa Gly Val Pro Gly Xaa Gly Val
                485                 490                 495
Pro Gly Xaa Gly Val Pro Gly Xaa Gly Val Pro Gly Xaa Gly Val Pro
            500                 505                 510
Gly Xaa Gly Val Pro Gly Xaa Gly Val Pro Gly Xaa Gly Val Pro Gly
        515                 520                 525
Xaa Gly Val Pro Gly Xaa Gly Val Pro Gly Xaa Gly Val Pro Gly Xaa
    530                 535                 540
Gly Val Pro Gly Xaa Gly Val Pro Gly Xaa Gly Val Pro Gly Xaa Gly
545                 550                 555                 560
Val Pro Gly Xaa Gly Val Pro Gly Xaa Gly Val Pro Gly Xaa Gly Val
                565                 570                 575
Pro Gly Xaa Gly Val Pro Gly Xaa Gly Val Pro Gly Xaa Gly Val Pro
            580                 585                 590
Gly Xaa Gly Val Pro Gly Xaa Gly Val Pro Gly Xaa Gly Val Pro Gly
        595                 600                 605
Xaa Gly Val Pro Gly Xaa Gly Val Pro Gly Xaa Gly Val Pro Gly Xaa
    610                 615                 620
Gly Val Pro Gly Xaa Gly Val Pro Gly Xaa Gly Val Pro Gly Xaa Gly
625                 630                 635                 640
Val Pro Gly Xaa Gly Val Pro Gly Xaa Gly Val Pro Gly Xaa Gly Val
                645                 650                 655
Pro Gly Xaa Gly Val Pro Gly Xaa Gly Val Pro Gly Xaa Gly Val Pro
            660                 665                 670
Gly Xaa Gly Val Pro Gly Xaa Gly Val Pro Gly Xaa Gly Val Pro Gly
        675                 680                 685
Xaa Gly Val Pro Gly Xaa Gly Val Pro Gly Xaa Gly Val Pro Gly Xaa
    690                 695                 700
Gly Val Pro Gly Xaa Gly Val Pro Gly Xaa Gly Val Pro Gly Xaa Gly
705                 710                 715                 720
Val Pro Gly Xaa Gly Val Pro Gly Xaa Gly Val Pro Gly Xaa Gly Val
                725                 730                 735
Pro Gly Xaa Gly Val Pro Gly Xaa Gly Val Pro Gly Xaa Gly Val Pro
            740                 745                 750
Gly Xaa Gly Val Pro Gly Xaa Gly Val Pro Gly Xaa Gly Val Pro Gly
        755                 760                 765
Xaa Gly Val Pro Gly Xaa Gly Val Pro Gly Xaa Gly Val Pro Gly Xaa
    770                 775                 780
```

-continued

Gly Val Pro Gly Xaa Gly Val Pro Gly Xaa Gly Val Pro Gly Xaa Gly
785                 790                 795                 800

Val Pro Gly Xaa Gly Val Pro Gly Xaa Gly Val Pro Gly Xaa Gly Val
                805                 810                 815

Pro Gly Xaa Gly Val Pro Gly Xaa Gly Val Pro Gly Xaa Gly Val Pro
            820                 825                 830

Gly Xaa Gly Val Pro Gly Xaa Gly Val Pro Gly Xaa Gly Val Pro Gly
        835                 840                 845

Xaa Gly Val Pro Gly Xaa Gly Val Pro Gly Xaa Gly Val Pro Gly Xaa
850                 855                 860

Gly Val Pro Gly Xaa Gly Val Pro Gly Xaa Gly Val Pro Gly Xaa Gly
865                 870                 875                 880

Val Pro Gly Xaa Gly Val Pro Gly Xaa Gly Val Pro Gly Xaa Gly Val
                885                 890                 895

Pro Gly Xaa Gly Val Pro Gly Xaa Gly Val Pro Gly Xaa Gly Val Pro
            900                 905                 910

Gly Xaa Gly Val Pro Gly Xaa Gly Val Pro Gly Xaa Gly Val Pro Gly
        915                 920                 925

Xaa Gly Val Pro Gly Xaa Gly Val Pro Gly Xaa Gly Val Pro Gly Xaa
930                 935                 940

Gly Val Pro Gly Xaa Gly Val Pro Gly Xaa Gly Val Pro Gly Xaa Gly
945                 950                 955                 960

Val Pro Gly Xaa Gly Val Pro Gly Xaa Gly Val Pro Gly Xaa Gly Val
                965                 970                 975

Pro Gly Xaa Gly Val Pro Gly Xaa Gly Val Pro Gly Xaa Gly Val Pro
            980                 985                 990

Gly Xaa Gly Val Pro Gly Xaa Gly  Val Pro Gly Xaa Gly  Val Pro Gly
        995                 1000                 1005

Xaa Gly  Val Pro Gly Xaa Gly  Val Pro Gly Xaa Gly  Val Pro Gly
    1010                 1015                 1020

Xaa Gly  Val Pro Gly Xaa Gly  Val Pro Gly Xaa Gly  Val Pro Gly
    1025                 1030                 1035

Xaa Gly  Val Pro Gly Xaa Gly  Val Pro Gly Xaa Gly  Val Pro Gly
    1040                 1045                 1050

Xaa Gly  Val Pro Gly Xaa Gly  Val Pro Gly Xaa Gly  Val Pro Gly
    1055                 1060                 1065

Xaa Gly  Val Pro Gly Xaa Gly  Val Pro Gly Xaa Gly  Val Pro Gly
    1070                 1075                 1080

Xaa Gly  Val Pro Gly Xaa Gly  Val Pro Gly Xaa Gly  Val Pro Gly
    1085                 1090                 1095

Xaa Gly  Val Pro Gly Xaa Gly  Val Pro Gly Xaa Gly  Val Pro Gly
    1100                 1105                 1110

Xaa Gly  Val Pro Gly Xaa Gly  Val Pro Gly Xaa Gly  Val Pro Gly
    1115                 1120                 1125

Xaa Gly  Val Pro Gly Xaa Gly  Val Pro Gly Xaa Gly  Val Pro Gly
    1130                 1135                 1140

Xaa Gly  Val Pro Gly Xaa Gly  Val Pro Gly Xaa Gly  Val Pro Gly
    1145                 1150                 1155

Xaa Gly  Val Pro Gly Xaa Gly  Val Pro Gly Xaa Gly  Val Pro Gly
    1160                 1165                 1170

Xaa Gly  Val Pro Gly Xaa Gly  Val Pro Gly Xaa Gly  Val Pro Gly
    1175                 1180                 1185

-continued

Xaa Gly Val Pro Gly Xaa Gly Val Pro Gly Xaa Gly Val Pro Gly
    1190                1195                1200

Xaa Gly Val Pro Gly Xaa Gly Val Pro Gly Xaa Gly Val Pro Gly
    1205                1210                1215

Xaa Gly Val Pro Gly Xaa Gly Val Pro Gly Xaa Gly Val Pro Gly
    1220                1225                1230

Xaa Gly Val Pro Gly Xaa Gly Val Pro Gly Xaa Gly Val Pro Gly
    1235                1240                1245

Xaa Gly Val Pro Gly Xaa Gly Val Pro Gly Xaa Gly Val Pro Gly
    1250                1255                1260

Xaa Gly Val Pro Gly Xaa Gly Val Pro Gly Xaa Gly Val Pro Gly
    1265                1270                1275

Xaa Gly Val Pro Gly Xaa Gly Val Pro Gly Xaa Gly Val Pro Gly
    1280                1285                1290

Xaa Gly Val Pro Gly Xaa Gly Val Pro Gly Xaa Gly Val Pro Gly
    1295                1300                1305

Xaa Gly Val Pro Gly Xaa Gly Val Pro Gly Xaa Gly Val Pro Gly
    1310                1315                1320

Xaa Gly Val Pro Gly Xaa Gly Val Pro Gly Xaa Gly Val Pro Gly
    1325                1330                1335

Xaa Gly Val Pro Gly Xaa Gly Val Pro Gly Xaa Gly Val Pro Gly
    1340                1345                1350

Xaa Gly Val Pro Gly Xaa Gly Val Pro Gly Xaa Gly Val Pro Gly
    1355                1360                1365

Xaa Gly Val Pro Gly Xaa Gly Val Pro Gly Xaa Gly Val Pro Gly
    1370                1375                1380

Xaa Gly Val Pro Gly Xaa Gly Val Pro Gly Xaa Gly Val Pro Gly
    1385                1390                1395

Xaa Gly Val Pro Gly Xaa Gly Val Pro Gly Xaa Gly Val Pro Gly
    1400                1405                1410

Xaa Gly Val Pro Gly Xaa Gly Val Pro Gly Xaa Gly Val Pro Gly
    1415                1420                1425

Xaa Gly Val Pro Gly Xaa Gly Val Pro Gly Xaa Gly Val Pro Gly
    1430                1435                1440

Xaa Gly Val Pro Gly Xaa Gly Val Pro Gly Xaa Gly Val Pro Gly
    1445                1450                1455

Xaa Gly Val Pro Gly Xaa Gly Val Pro Gly Xaa Gly Val Pro Gly
    1460                1465                1470

Xaa Gly Val Pro Gly Xaa Gly Val Pro Gly Xaa Gly Val Pro Gly
    1475                1480                1485

Xaa Gly Val Pro Gly Xaa Gly Val Pro Gly Xaa Gly Val Pro Gly
    1490                1495                1500

Xaa Gly Val Pro Gly Xaa Gly Val Pro Gly Xaa Gly Val Pro Gly
    1505                1510                1515

Xaa Gly Val Pro Gly Xaa Gly Val Pro Gly Xaa Gly Val Pro Gly
    1520                1525                1530

Xaa Gly Val Pro Gly Xaa Gly Val Pro Gly Xaa Gly Val Pro Gly
    1535                1540                1545

Xaa Gly Val Pro Gly Xaa Gly Val Pro Gly Xaa Gly Val Pro Gly
    1550                1555                1560

Xaa Gly Val Pro Gly Xaa Gly Val Pro Gly Xaa Gly Val Pro Gly
    1565                1570                1575

Xaa Gly Val Pro Gly Xaa Gly Val Pro Gly Xaa Gly Val Pro Gly

|      |      |      |
|------|------|------|
| 1580 | 1585 | 1590 |

Xaa Gly  Val Pro Gly Xaa Gly  Val Pro Gly Xaa  Gly  Val Pro Gly
    1595                 1600                 1605

Xaa Gly  Val Pro Gly Xaa Gly  Val Pro Gly Xaa  Gly  Val Pro Gly
    1610                 1615                 1620

Xaa Gly  Val Pro Gly Xaa Gly  Val Pro Gly Xaa  Gly  Val Pro Gly
    1625                 1630                 1635

Xaa Gly  Val Pro Gly Xaa Gly  Val Pro Gly Xaa  Gly  Val Pro Gly
    1640                 1645                 1650

Xaa Gly  Val Pro Gly Xaa Gly  Val Pro Gly Xaa  Gly  Val Pro Gly
    1655                 1660                 1665

Xaa Gly  Val Pro Gly Xaa Gly  Val Pro Gly Xaa  Gly  Val Pro Gly
    1670                 1675                 1680

Xaa Gly  Val Pro Gly Xaa Gly  Val Pro Gly Xaa  Gly  Val Pro Gly
    1685                 1690                 1695

Xaa Gly  Val Pro Gly Xaa Gly  Val Pro Gly Xaa  Gly  Val Pro Gly
    1700                 1705                 1710

Xaa Gly  Val Pro Gly Xaa Gly  Val Pro Gly Xaa  Gly  Val Pro Gly
    1715                 1720                 1725

Xaa Gly  Val Pro Gly Xaa Gly  Val Pro Gly Xaa  Gly  Val Pro Gly
    1730                 1735                 1740

Xaa Gly  Val Pro Gly Xaa Gly
    1745             1750

<210> SEQ ID NO 45
<211> LENGTH: 1752
<212> TYPE: PRT
<213> ORGANISM: Artificial Sequence
<220> FEATURE:
<223> OTHER INFORMATION: Elastin-like polypeptide variant
<220> FEATURE:
<221> NAME/KEY: X
<222> LOCATION: (1)..(1752)
<223> OTHER INFORMATION: X is equal to valine, glycine, or alanine.  The
      sequence includes 350 repeating units of the amino acid sequence
      VPGXG, i.e., n=350; however, this unit can be repeated such that n
      is an integer from about 5 to about 350.

<400> SEQUENCE: 45

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
    130                 135                 140

```
Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
            165                 170                 175

Pro Gly Xaa Gly Val Pro Gly Xaa Gly Val Pro Gly Xaa Gly Val Pro
        180                 185                 190

Gly Xaa Gly Val Pro Gly Xaa Gly Val Pro Gly Xaa Gly Val Pro Gly
    195                 200                 205

Xaa Gly Val Pro Gly Xaa Gly Val Pro Gly Xaa Gly Val Pro Gly Xaa
210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
            245                 250                 255

Pro Gly Xaa Gly Val Pro Gly Xaa Gly Val Pro Gly Xaa Gly Val Pro
        260                 265                 270

Gly Xaa Gly Val Pro Gly Xaa Gly Val Pro Gly Xaa Gly Val Pro Gly
    275                 280                 285

Xaa Gly Val Pro Gly Xaa Gly Val Pro Gly Xaa Gly Val Pro Gly Xaa
290                 295                 300

Gly Val Pro Gly Xaa Gly Val Pro Gly Xaa Gly Val Pro Gly Xaa Gly
305                 310                 315                 320

Val Pro Gly Xaa Gly Val Pro Gly Xaa Gly Val Pro Gly Xaa Gly Val
            325                 330                 335

Pro Gly Xaa Gly Val Pro Gly Xaa Gly Val Pro Gly Xaa Gly Val Pro
        340                 345                 350

Gly Xaa Gly Val Pro Gly Xaa Gly Val Pro Gly Xaa Gly Val Pro Gly
    355                 360                 365

Xaa Gly Val Pro Gly Xaa Gly Val Pro Gly Xaa Gly Val Pro Gly Xaa
370                 375                 380

Gly Val Pro Gly Xaa Gly Val Pro Gly Xaa Gly Val Pro Gly Xaa Gly
385                 390                 395                 400

Val Pro Gly Xaa Gly Val Pro Gly Xaa Gly Val Pro Gly Xaa Gly Val
            405                 410                 415

Pro Gly Xaa Gly Val Pro Gly Xaa Gly Val Pro Gly Xaa Gly Val Pro
        420                 425                 430

Gly Xaa Gly Val Pro Gly Xaa Gly Val Pro Gly Xaa Gly Val Pro Gly
    435                 440                 445

Xaa Gly Val Pro Gly Xaa Gly Val Pro Gly Xaa Gly Val Pro Gly Xaa
450                 455                 460

Gly Val Pro Gly Xaa Gly Val Pro Gly Xaa Gly Val Pro Gly Xaa Gly
465                 470                 475                 480

Val Pro Gly Xaa Gly Val Pro Gly Xaa Gly Val Pro Gly Xaa Gly Val
            485                 490                 495

Pro Gly Xaa Gly Val Pro Gly Xaa Gly Val Pro Gly Xaa Gly Val Pro
        500                 505                 510

Gly Xaa Gly Val Pro Gly Xaa Gly Val Pro Gly Xaa Gly Val Pro Gly
    515                 520                 525

Xaa Gly Val Pro Gly Xaa Gly Val Pro Gly Xaa Gly Val Pro Gly Xaa
530                 535                 540

Gly Val Pro Gly Xaa Gly Val Pro Gly Xaa Gly Val Pro Gly Xaa Gly
545                 550                 555                 560
```

Val Pro Gly Xaa Gly Val Pro Gly Xaa Gly Val Pro Gly Xaa Gly Val
            565                 570                 575

Pro Gly Xaa Gly Val Pro Gly Xaa Gly Val Pro Gly Xaa Gly Val Pro
            580                 585                 590

Gly Xaa Gly Val Pro Gly Xaa Gly Val Pro Gly Xaa Gly Val Pro Gly
            595                 600                 605

Xaa Gly Val Pro Gly Xaa Gly Val Pro Gly Xaa Gly Val Pro Gly Xaa
            610                 615                 620

Gly Val Pro Gly Xaa Gly Val Pro Gly Xaa Gly Val Pro Gly Xaa Gly
625                 630                 635                 640

Val Pro Gly Xaa Gly Val Pro Gly Xaa Gly Val Pro Gly Xaa Gly Val
            645                 650                 655

Pro Gly Xaa Gly Val Pro Gly Xaa Gly Val Pro Gly Xaa Gly Val Pro
            660                 665                 670

Gly Xaa Gly Val Pro Gly Xaa Gly Val Pro Gly Xaa Gly Val Pro Gly
            675                 680                 685

Xaa Gly Val Pro Gly Xaa Gly Val Pro Gly Xaa Gly Val Pro Gly Xaa
            690                 695                 700

Gly Val Pro Gly Xaa Gly Val Pro Gly Xaa Gly Val Pro Gly Xaa Gly
705                 710                 715                 720

Val Pro Gly Xaa Gly Val Pro Gly Xaa Gly Val Pro Gly Xaa Gly Val
            725                 730                 735

Pro Gly Xaa Gly Val Pro Gly Xaa Gly Val Pro Gly Xaa Gly Val Pro
            740                 745                 750

Gly Xaa Gly Val Pro Gly Xaa Gly Val Pro Gly Xaa Gly Val Pro Gly
            755                 760                 765

Xaa Gly Val Pro Gly Xaa Gly Val Pro Gly Xaa Gly Val Pro Gly Xaa
            770                 775                 780

Gly Val Pro Gly Xaa Gly Val Pro Gly Xaa Gly Val Pro Gly Xaa Gly
785                 790                 795                 800

Val Pro Gly Xaa Gly Val Pro Gly Xaa Gly Val Pro Gly Xaa Gly Val
            805                 810                 815

Pro Gly Xaa Gly Val Pro Gly Xaa Gly Val Pro Gly Xaa Gly Val Pro
            820                 825                 830

Gly Xaa Gly Val Pro Gly Xaa Gly Val Pro Gly Xaa Gly Val Pro Gly
            835                 840                 845

Xaa Gly Val Pro Gly Xaa Gly Val Pro Gly Xaa Gly Val Pro Gly Xaa
            850                 855                 860

Gly Val Pro Gly Xaa Gly Val Pro Gly Xaa Gly Val Pro Gly Xaa Gly
865                 870                 875                 880

Val Pro Gly Xaa Gly Val Pro Gly Xaa Gly Val Pro Gly Xaa Gly Val
            885                 890                 895

Pro Gly Xaa Gly Val Pro Gly Xaa Gly Val Pro Gly Xaa Gly Val Pro
            900                 905                 910

Gly Xaa Gly Val Pro Gly Xaa Gly Val Pro Gly Xaa Gly Val Pro Gly
            915                 920                 925

Xaa Gly Val Pro Gly Xaa Gly Val Pro Gly Xaa Gly Val Pro Gly Xaa
            930                 935                 940

Gly Val Pro Gly Xaa Gly Val Pro Gly Xaa Gly Val Pro Gly Xaa Gly
945                 950                 955                 960

Val Pro Gly Xaa Gly Val Pro Gly Xaa Gly Val Pro Gly Xaa Gly Val
            965                 970                 975

-continued

```
Pro Gly Xaa Gly Val Pro Gly Xaa Gly Val Pro Gly Xaa Gly Val Pro
            980                 985                 990
Gly Xaa Gly Val Pro Gly Xaa Gly  Val Pro Gly Xaa Gly  Val Pro Gly
        995                 1000                1005
Xaa Gly  Val Pro Gly Xaa Gly  Val Pro Gly Xaa Gly  Val Pro Gly
    1010                1015                1020
Xaa Gly  Val Pro Gly Xaa Gly  Val Pro Gly Xaa Gly  Val Pro Gly
    1025                1030                1035
Xaa Gly  Val Pro Gly Xaa Gly  Val Pro Gly Xaa Gly  Val Pro Gly
    1040                1045                1050
Xaa Gly  Val Pro Gly Xaa Gly  Val Pro Gly Xaa Gly  Val Pro Gly
    1055                1060                1065
Xaa Gly  Val Pro Gly Xaa Gly  Val Pro Gly Xaa Gly  Val Pro Gly
    1070                1075                1080
Xaa Gly  Val Pro Gly Xaa Gly  Val Pro Gly Xaa Gly  Val Pro Gly
    1085                1090                1095
Xaa Gly  Val Pro Gly Xaa Gly  Val Pro Gly Xaa Gly  Val Pro Gly
    1100                1105                1110
Xaa Gly  Val Pro Gly Xaa Gly  Val Pro Gly Xaa Gly  Val Pro Gly
    1115                1120                1125
Xaa Gly  Val Pro Gly Xaa Gly  Val Pro Gly Xaa Gly  Val Pro Gly
    1130                1135                1140
Xaa Gly  Val Pro Gly Xaa Gly  Val Pro Gly Xaa Gly  Val Pro Gly
    1145                1150                1155
Xaa Gly  Val Pro Gly Xaa Gly  Val Pro Gly Xaa Gly  Val Pro Gly
    1160                1165                1170
Xaa Gly  Val Pro Gly Xaa Gly  Val Pro Gly Xaa Gly  Val Pro Gly
    1175                1180                1185
Xaa Gly  Val Pro Gly Xaa Gly  Val Pro Gly Xaa Gly  Val Pro Gly
    1190                1195                1200
Xaa Gly  Val Pro Gly Xaa Gly  Val Pro Gly Xaa Gly  Val Pro Gly
    1205                1210                1215
Xaa Gly  Val Pro Gly Xaa Gly  Val Pro Gly Xaa Gly  Val Pro Gly
    1220                1225                1230
Xaa Gly  Val Pro Gly Xaa Gly  Val Pro Gly Xaa Gly  Val Pro Gly
    1235                1240                1245
Xaa Gly  Val Pro Gly Xaa Gly  Val Pro Gly Xaa Gly  Val Pro Gly
    1250                1255                1260
Xaa Gly  Val Pro Gly Xaa Gly  Val Pro Gly Xaa Gly  Val Pro Gly
    1265                1270                1275
Xaa Gly  Val Pro Gly Xaa Gly  Val Pro Gly Xaa Gly  Val Pro Gly
    1280                1285                1290
Xaa Gly  Val Pro Gly Xaa Gly  Val Pro Gly Xaa Gly  Val Pro Gly
    1295                1300                1305
Xaa Gly  Val Pro Gly Xaa Gly  Val Pro Gly Xaa Gly  Val Pro Gly
    1310                1315                1320
Xaa Gly  Val Pro Gly Xaa Gly  Val Pro Gly Xaa Gly  Val Pro Gly
    1325                1330                1335
Xaa Gly  Val Pro Gly Xaa Gly  Val Pro Gly Xaa Gly  Val Pro Gly
    1340                1345                1350
Xaa Gly  Val Pro Gly Xaa Gly  Val Pro Gly Xaa Gly  Val Pro Gly
    1355                1360                1365
```

-continued

```
Xaa Gly Val Pro Gly Xaa Gly Val Pro Gly Xaa Gly Val Pro Gly
    1370            1375            1380

Xaa Gly Val Pro Gly Xaa Gly Val Pro Gly Xaa Gly Val Pro Gly
    1385            1390            1395

Xaa Gly Val Pro Gly Xaa Gly Val Pro Gly Xaa Gly Val Pro Gly
    1400            1405            1410

Xaa Gly Val Pro Gly Xaa Gly Val Pro Gly Xaa Gly Val Pro Gly
    1415            1420            1425

Xaa Gly Val Pro Gly Xaa Gly Val Pro Gly Xaa Gly Val Pro Gly
    1430            1435            1440

Xaa Gly Val Pro Gly Xaa Gly Val Pro Gly Xaa Gly Val Pro Gly
    1445            1450            1455

Xaa Gly Val Pro Gly Xaa Gly Val Pro Gly Xaa Gly Val Pro Gly
    1460            1465            1470

Xaa Gly Val Pro Gly Xaa Gly Val Pro Gly Xaa Gly Val Pro Gly
    1475            1480            1485

Xaa Gly Val Pro Gly Xaa Gly Val Pro Gly Xaa Gly Val Pro Gly
    1490            1495            1500

Xaa Gly Val Pro Gly Xaa Gly Val Pro Gly Xaa Gly Val Pro Gly
    1505            1510            1515

Xaa Gly Val Pro Gly Xaa Gly Val Pro Gly Xaa Gly Val Pro Gly
    1520            1525            1530

Xaa Gly Val Pro Gly Xaa Gly Val Pro Gly Xaa Gly Val Pro Gly
    1535            1540            1545

Xaa Gly Val Pro Gly Xaa Gly Val Pro Gly Xaa Gly Val Pro Gly
    1550            1555            1560

Xaa Gly Val Pro Gly Xaa Gly Val Pro Gly Xaa Gly Val Pro Gly
    1565            1570            1575

Xaa Gly Val Pro Gly Xaa Gly Val Pro Gly Xaa Gly Val Pro Gly
    1580            1585            1590

Xaa Gly Val Pro Gly Xaa Gly Val Pro Gly Xaa Gly Val Pro Gly
    1595            1600            1605

Xaa Gly Val Pro Gly Xaa Gly Val Pro Gly Xaa Gly Val Pro Gly
    1610            1615            1620

Xaa Gly Val Pro Gly Xaa Gly Val Pro Gly Xaa Gly Val Pro Gly
    1625            1630            1635

Xaa Gly Val Pro Gly Xaa Gly Val Pro Gly Xaa Gly Val Pro Gly
    1640            1645            1650

Xaa Gly Val Pro Gly Xaa Gly Val Pro Gly Xaa Gly Val Pro Gly
    1655            1660            1665

Xaa Gly Val Pro Gly Xaa Gly Val Pro Gly Xaa Gly Val Pro Gly
    1670            1675            1680

Xaa Gly Val Pro Gly Xaa Gly Val Pro Gly Xaa Gly Val Pro Gly
    1685            1690            1695

Xaa Gly Val Pro Gly Xaa Gly Val Pro Gly Xaa Gly Val Pro Gly
    1700            1705            1710

Xaa Gly Val Pro Gly Xaa Gly Val Pro Gly Xaa Gly Val Pro Gly
    1715            1720            1725

Xaa Gly Val Pro Gly Xaa Gly Val Pro Gly Xaa Gly Val Pro Gly
    1730            1735            1740

Xaa Gly Val Pro Gly Xaa Gly Trp Pro
    1745            1750
```

US 8,841,414 B1

TARGETED DELIVERY OF THERAPEUTIC PEPTIDES BY THERMALLY RESPONSIVE BIOPOLYMERS

PRIOR APPLICATIONS

This application is a continuation-in-part of U.S. patent application Ser. No. 12/422,970 filed on Apr. 13, 2009, which claims benefit to U.S. Patent Application No. 61/044,424 filed on Apr. 11, 2008; and this application is a continuation in part of U.S. patent application Ser. No. 12/162,283, which is a national phase application of International Patent Application No. PCT/US07/61240, filed on Jan. 29, 2007, which claims benefit to U.S. Patent Application No. 60/762,919 filed on Jan. 27, 2006. The content of patent application Ser. Nos. 12/422,970; 61/044,424; 12/162,283; PCT/US07/61240; and 60/762,919 are incorporated herein by reference.

INTRODUCTION

Embodiments of the present invention include a compound including a cell-penetrating peptide (CPP), an elastin-like polypeptide (ELP), and a therapeutic polypeptide (TP) that inhibits cell proliferation; and a method of using the compound for treatment of cancer. Embodiments of the compounds of the present invention are thermally-responsive, such that the compound can be specifically targeted to a tumor site by applying local local hyperthermia.

Macromolecular delivery systems are promising strategies to deliver therapeutic compounds. To date, liposomes and micro- and nano-particle based drug delivery systems have been developed to improve the efficacy of various therapeutic compounds. However, improvements are needed. In many cases, only a small fraction of an administered dose of drug reaches the target site, while the rest of the drug is distributed throughout the body, which can result in resulting damage to non-target tissue. Targeted therapeutic approaches, which would increase the specificity and efficacy of a therapeutic, would be desirable.

Although many different systems such as low molecular weight prodrugs, liposomes, and micro- and nano-particles have been developed for targeted treatment, e.g., to treat solid tumors, there are specific advantages in combining macromolecular carriers with focused hyperthermia of a target site. First, soluble polymeric carriers are attractive for systemic drug delivery because polymer-drug conjugates preferentially accumulate in tumors due to their enhanced microvascular permeability and retention, and exhibit significantly lower systemic toxicity compared to free drug. Studies have shown that water soluble polymer carriers can overcome multidrug resistance. Second, hyperthermia preferentially increases the permeability of tumor vasculature compared to normal vasculature, which can further enhance the delivery of drugs to tumors. Hyperthermia has been introduced in the treatment of glioblastoma, head and neck cancer, breast cancer, cancer of the gastrointestinal or urogenital tract, and sarcoma. Superficial tumors are heated by means of antennas or applicators emitting radiowaves or microwaves placed on tumor surfaces with a contacting medium. Multiantenna applicators are used to heat deep-seated tumors, such as tumors located in the pelvis or abdomen.

With recent improvement in the control of power-density, temperature distribution and treatment monitoring by magnetic resonance tomography, which can characterize temperature as well as perfusion, it is possible to heat only a limited and specific tumor area and minimize the effects of non-specific toxicity. Consequently, the methods and techniques necessary to employ thermal targeting of thermally sensitive polypeptides are available in the clinical setting.

Therefore, as proposed herein, are compositions and methods for thermally targeted delivery of therapeutic polypeptides to a target site.

Brief Description of the Sequence Listing

SEQ ID NO: 1 is a Tat cell penetrating polypeptide.
SEQ ID NO: 2 is a Penetratin cell penetrating polypeptide.
SEQ ID NO: 3 is a Bac cell penetrating polypeptide.
SEQ ID NO: 4 is a SynB1 cell penetrating polypeptide.
SEQ ID NO: 5 is a SynB1-NLS cell penetrating polypeptide.
SEQ ID NO: 6 is a poly-arginine cell penetrating polypeptide including seven (7) arginines.
SEQ ID NO: 7 is a poly-arginine cell penetrating polypeptide including eight (8) arginines.
SEQ ID NO: 8 is a poly-arginine cell penetrating polypeptide including nine (9) arginines.
SEQ ID NO: 9 is a poly-arginine cell penetrating polypeptide including ten (10) arginines.
SEQ ID NO: 10 is a poly-arginine cell penetrating polypeptide including eleven (11) arginines.
SEQ ID NO: 11 is a VP22 cell penetrating polypeptide.
SEQ ID NO: 12 is a Transportan cell penetrating polypeptide.
SEQ ID NO: 13 is a MAP cell penetrating polypeptide.
SEQ ID NO: 14 is a pVEC cell penetrating polypeptide.
SEQ ID NO: 15 is a MTS cell penetrating polypeptide.
SEQ ID NO: 16 is a hCT-derived cell penetrating polypeptide.
SEQ ID NO: 17 is a MPG cell penetrating polypeptide.
SEQ ID NO: 18 is a Buforin 2 cell penetrating polypeptide.
SEQ ID NO: 19 is a PEP-1 cell penetrating polypeptide.
SEQ ID NO: 20 is a Magainin 2 cell penetrating polypeptide.
SEQ ID NO: 21 is an embodiment of an elastin-like polypeptide that includes repeating units of the amino acid sequence VPGXG, where eachs X is independently selected from valine, glycine, and alanine such that the Xs are provided in a 5:3:2 ratio.
SEQ ID NO: 22 is an embodiment of an elastin-like polypeptide that includes repeating units of the amino acid sequence VPGXG, where eachs X is independently selected from valine, glycine, and alanine such that the Xs are provided in a 1:7:8 ratio.
SEQ ID NO: 23 is an embodiment of an amino acid comprising a Tat cell penetrating polypeptide and an elastin-like polypeptide.
SEQ ID NO: 24 is another embodiment of an amino acid including a Tat cell penetrating polypeptide and an elastin-like polypeptide.
SEQ ID NO: 25 is an embodiment of an amino acid including a Penetratin cell penetrating polypeptide and an elastin-like polypeptide.
SEQ ID NO: 26 is another embodiment of an amino acid including a Penetratin cell penetrating polypeptide and an elastin-like polypeptide.
SEQ ID NO: 27 is an embodiment of an amino acid including an MTS cell penetrating polypeptide and an elastin-like polypeptide.
SEQ ID NO: 28 is another embodiment of an amino acid including an MTS cell penetrating polypeptide and an elastin-like polypeptide.
SEQ ID NO: 29 is an embodiment of an amino acid including a Bac-7 cell penetrating polypeptide and an elastin-like polypeptide.

SEQ ID NO: 30 is another embodiment of an amino acid including a Bac-7 cell penetrating polypeptide and an elastin-like polypeptide.

SEQ ID NO: 31 is an embodiment of an amino acid including a Transportan cell penetrating polypeptide and an elastin-like polypeptide.

SEQ ID NO: 32 is another embodiment of an amino acid including a Transportan cell penetrating polypeptide and an elastin-like polypeptide.

SEQ ID NO: 33 is an embodiment of an amino acid including a pVEC cell penetrating polypeptide and an elastin-like polypeptide.

SEQ ID NO: 34 is another embodiment of an amino acid including a pVEC cell penetrating polypeptide and an elastin-like polypeptide.

SEQ ID NO: 35 is an embodiment of an amino acid including a SynB1 cell penetrating polypeptide and an elastin-like polypeptide.

SEQ ID NO: 36 is another embodiment of an amino acid including a SynB1 cell penetrating polypeptide and an elastin-like polypeptide.

SEQ ID NO: 37 is an embodiment of an amino acid sequence of a therapeutic peptide referred to herein as H1.

SEQ ID NO: 38 is an embodiment of an amino acid sequence of a therapeutic peptide referred to herein as p21.

SEQ ID NO: 39 is an embodiment of an amino acid sequence of a therapeutic peptide referred to herein as KLAK.

SEQ ID NO: 40 is an embodiment of an amino acid sequence of a therapeutic peptide referred to herein as p50.

SEQ ID NO: 41 is an amino acid sequence, GGCGGCGGC, which can be included in embodimentns of the compound of the present invention.

SEQ ID NO: 42 is an amino acid sequence, VPGXG, where each X is independently selected from valine (Val; V), glycine (Gly; G), and alanine (Ala; A).

SEQ ID NO: 43 is an amino acid sequence of the eponymous sequence motif QTSMTDFY.

SEQ ID NO: 44 is an amino acid sequence that includes repeating units of the amino acid sequence VPGXG, where each X is independently selected from valine, glycine, and alanine.

SEQ ID NO: 45 is an amino acid sequence, $(VPGXG)_n WP$, where each X is independently selected from valine, glycine, and alanine

BRIEF DESCRIPTION OF THE DRAWINGS

FIG. 33-1 is a set of graphs that show proliferation with DFMO and Dox or Etoposide. Cells were pretreated with 20 µM Pen-ELP-H1 or 50 µM DFMO on day 1, and treated with 750 nM Dox (A) or 200 µM etoposide (B) on day 4. Cell viability was determined on day 7 using the MTS cell viability assay. Results represent the mean±SEM of 3 independent experiments.

FIG. 33-2 is a set of graphs showing effects of compounds as disclosed herein on cell proliferation. SKOV-3 cells were treated with the indicated polypeptides for 1 h at 37 or 42° C. Cell viability was determined by MTS assay 3 and 6 days later. Bac7-ELP1-p21 treatment at 42° C. caused nearly 50% inhibition 3 days after a single 1 h treatment at 20 and 30 µM polypeptide concentration (A). 6 days after treatment, the 30 µM dose inhibited cell proliferation by about 80% (B). Cell proliferation was monitored with time after a single 1 h exposure to Bac7-ELP1-p21 (C). Untreated cells and cells treated with the control polypeptide Bac7-ELP-ggc grew exponentially, doubling about 3.5 times in 6 days. When applied at 37° C., Bac7-ELP1-p21 had no effect on the proliferation rate; when treated at 42° C., Bac7-ELP1-p21 almost completely abolished SKOV-3 cell proliferation.

DESCRIPTION OF EMBODIMENTS OF THE INVENTION

Figure 1:
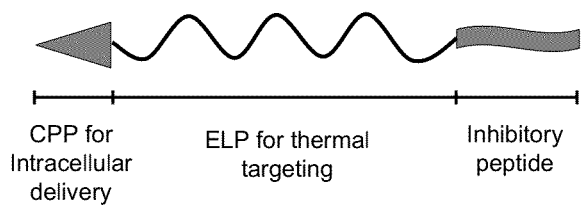
FIG. 1 shows an example of a model of the ELP-based peptide delivery vector. The ELP polypeptide is modified at the N-terminus with a cell penetrating peptide (CPP) to enhance intracellular delivery, and an inhibitory peptide is attached at the ELP C-terminus.

The present invention includes a compound compositions and methods for thermally targeted delivery of therapeutic polypeptides to a target site, including an elastin-like polypeptide (ELP), and a therapeutic polypeptide (TP). In some embodiments, the compound further comprises a cell penetrating polypeptide (CPP). In some embodiments, the compound can be administered to treat a condition of interest in a subject in need thereof. In some embodiments the therapeutic polypeptide is a polypeptide that inhibits cell proliferation. In some embodiments, the compound can be administered to a subject to inhibit the proliferation of a cancer in the subject. In some embodiments, the composition can be administered to a subject for delivery to a target site, to which local hyperthermia has been applied.

Therapeutic Polypeptides (TPs) are promising because they can be designed to inhibit specific molecular interactions; however, their efficacy in vivo is limited by poor pharmacokinetic parameters. To improve their pharmacokinetics and bio-distribution, as described herein, the present inventors have selected TPs and fused them an ELP. The resulting compound can be targeted to a target site of a subject by applying local hyperthermia.

As used herein, the term "cell penetrating polypeptide" (CPP) refers to a polypeptide that facilitates transport of the compound through a cell membrane.

As used herein, the term "polypeptide" means any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted.

Cell penetrating peptides can be short polypeptides capable of mediating delivery of molecules across a cell membrane. In some embodiments, CPPs can be comprised of mostly basic amino acids, hydrophobic amino acids, or an amphipathic sequence. Examples of CPPs that can be used in accordance with the present invention include, but are not limited, to those set forth in Table 1.

TABLE 1

| CPP | Amino Acid Sequence | SEQ ID NO: |
|---|---|---|
| Tat[1] | YGRKKRRQRRR | 1 |
| Penetratin (Antp)[2] | RQIKIWFQNRRMKWKK | 2 |
| Bac[3] | RRIRPRPPRLPRPRPRPLPFPRPG | 3 |

TABLE 1-continued

| CPP | Amino Acid Sequence | SEQ ID NO: |
|---|---|---|
| SynB1 | RGGRLSYSRRRFSTSTGR | 4 |
| SynB1-NLS[4] | RGGRLSYSRRRFSTSTGRWSQPKKKRKV | 5 |
| Poly-arginine | (R)$_{7-11}$ | 6, 7, 8, 9, 10 |
| VP22 | DAATATRGRSAASRPTQRPRAPARSASRPRRPVQ | 11 |
| Transportan[5] | GWTLNSAGYLLGKINLKALAALAKKIL | 12 |
| MAP | KLALKLALKALKAALKLA | 13 |
| pVEC[6] | LLIILRRRIRKQAHAHSK | 14 |
| MTS[7] | AAVALLPAVLLALLAP | 15 |
| hCT derived | LGTYTQDFNKFHTFPQTAIGVGAP | 16 |
| MPG | GALFLGFLGAAGSTMGAWSQPKKKRKV | 17 |
| Buforin 2 | TRSSRAGLQFPVGRVHRLLRK | 18 |
| PEP-1 | KETWWETWWTEWSQPKKKRKV | 19 |
| Magainin 2 | GIGKFLHSAKKFGKAFVGEIMNS | 20 |

[1]Tat is a cell penetrating peptide derived from the HIV-1 Tat protein (18).
[2]Penetratin (commonly abbreviated Pen or AntP) is the penetratin peptide derived from the *Drosophila* transcription factor Antennapaedia (17).
[3]Bac-7 is an antimicrobial peptide from the Bactenecin-7 family (20).
[4]SynB1-NLS is a version of the SynB1 CPP modified in the present inventors' lab by the addition of a nuclear localization sequence (NLS, underlined amino acids) to allow delivery of the compound not only across the cell membrane, but also into the cell's nucleus.
[5]Transportan is a chimeric peptide in which the first 13 amino acids are derived from galanin and the other 14 amino acids from the wasp venom peptide toxin, mastoparan (21).
[6]pVEC is derived from murine Vascular Endothelial Cadherin (22).
[7]MTS is the membrane translocating sequence derived from Kaposi fibroblast growth factor (19).

Embodiments of compounds of the present invention further include an elastin-like polypeptide (ELP).

In some embodiments, the ELP is an approximately 60 kilodalton protein comprising repeated units of the amino acid sequence VPGXG (SEQ ID NO: 42), where each X is independently selected from valine (Val; V), glycine (Gly; G), and alanine (Ala; A).

In some embodiments, the ELP can comprise the amino acid sequence (VPGXG)$_n$WP (SEQ ID NO: 45) or (VPGXG)$_n$ (SEQ ID NO: 44) where n is about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 135, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, or 245.

In some embodiments, the ELP can comprise the amino acid sequence (VPGXG)$_n$WP (SEQ ID NO: 45) or (VPGXG)$_n$ (SEQ ID NO: 44) where n is an integer of at least about 20, and each X is independently selected from valine, glycine, and alanine In some embodiments, the ELP can comprise the amino acid sequence (VPGXG)$_n$WP (SEQ ID NO: 45) or (VPGXG)$_n$ (SEQ ID NO: 44) where each X is independently selected from valine, glycine, and alanine such that the Xs are Val:Gly:Ala in a 5:3:2 ratio. For exemplary purposes only, to illustrate the ratio of Val:Gly:Ala in some embodiments of the composition, where n is 20, ten (10) of the Xs would be selected to be valine, six (6) of the Xs would be selected to be glycine, and four (4) of the Xs would be selected to be alanine.

In some embodiments, the ELP can comprise the amino acid sequence (VPGXG)$_n$WP (SEQ ID NO: 45) or (VPGXG)$_n$ (SEQ ID NO: 44) where n is about 20, 40, 80, 150, or 300, and where each X is independently selected from valine, glycine, and alanine such that the Xs are Val:Gly:Ala in a 5:3:2 ratio. In some embodiments, the ELP having Xs that are Val:Gly:Ala in a 5:3:2 ratio can comprise the amino acid sequence of SEQ ID NO: 22.

In some embodiments, the ELP can comprise the amino acid sequence (VPGXG)$_n$ WP (SEQ ID NO: 45) or (VPGXG)$_n$ (SEQ ID NO: 44) where each X is independently selected from valine, glycine, and alanine such that the Xs are Val:Gly:Ala in a 3:1:1 ratio. For exemplary purposes only, to illustrate the ratio of Val:Gly:Ala in some embodiments of the composition, where n is 5, three (3) of the Xs would be selected to be valine, one (1) X would be selected to be glycine, and one (1) X would be selected to be alanine In some embodiments, the ELP can comprise the amino acid sequence (VPGXG)$_n$WP (SEQ ID NO: 45) or (VPGXG)$_n$ (SEQ ID NO: 44) where n is about 20, 40, 80, 150, or 300, and where each X is independently selected from valine, glycine, and alanine such that the Xs are Val:Gly:Ala in a 3:1:1 ratio.

In some embodiments, the ELP can comprise the amino acid sequence (VPGXG)$_n$WP (SEQ ID NO: 45) or (VPGXG)$_n$ (SEQ ID NO: 44) where each X is independently selected from valine, glycine, and alanine such that the Xs are Val:Gly:Ala in a 1:7:8 ratio. For exemplary purposes only, to illustrate the ratio of Val:Gly:Ala in some embodiments of the composition, where n is 16, one (1) X would be selected to be valine, seven (7) of the Xs would be selected to be glycine, and eight (8) of the Xs would be selected to be alanine.

In some embodiments, the ELP can comprise the amino acid sequence (VPGXG)$_n$WP (SEQ ID NO: 45) or (VPGXG)$_n$ (SEQ ID NO: 44) where n is about 20, 40, 80, 150, or 300, and where each X is independently selected from valine, glycine, and alanine such that the Xs are Val:Gly:Ala in a 1:7:8 ratio. In some embodiments, the ELP having Xs that are Val:Gly:Ala in a 1:7:8 ratio can comprise the amino acid sequence of SEQ ID NO: 23.

In some embodiments, the ELP can be an ELP having the amino acid sequence of SEQ ID NO: 22. In some embodiments, the ELP can be an ELP having the amino acid sequence of SEQ ID NO: 23.

In some embodiments, the ELP is an ELP as described in U.S. Patent Application Publication No. 2005/0255554 of A. Chilkoti, which is incorporated herein by this reference.

In some embodiments, the compound of the presently-disclosed subject matter can include the amino acid sequence of SEQ ID NO: 24. In some embodiments, the compound of the presently-disclosed subject matter can include the amino acid sequence of SEQ ID NO: 25. In some embodiments, the compound of the presently-disclosed subject matter can include the amino acid sequence of SEQ ID NO: 26. In some embodiments, the compound of the presently-disclosed subject matter can include the amino acid sequence of SEQ ID NO: 27. In some embodiments, the compound of the presently-disclosed subject matter can include the amino acid sequence of SEQ ID NO: 28. In some embodiments, the compound of the presently-disclosed subject matter can include the amino acid sequence of SEQ ID NO: 29. In some embodiments, the compound of the presently-disclosed subject matter can include the amino acid sequence of SEQ ID NO: 30. In some embodiments, the compound of the presently-disclosed subject matter can include the amino acid sequence of SEQ ID NO: 31. In some embodiments, the compound of the presently-disclosed subject matter can include the amino acid sequence of SEQ ID NO: 32. In some embodiments, the compound of the presently-disclosed subject matter can include the amino acid sequence of SEQ ID NO: 33. In some embodiments, the compound of the presently-disclosed subject matter can include the amino acid sequence of SEQ ID NO: 34. In some embodiments, the compound of the presently-disclosed subject matter can include the amino acid sequence of SEQ ID NO: 35. In some embodiments, the compound of the presently-disclosed subject matter can include the amino acid sequence of SEQ ID NO: 36. In some embodiments, the compound of the presently-disclosed subject matter can include the amino acid sequence of SEQ ID NO: 37.

Embodiments of compounds of the present invention further a therapeutic polypeptide (TP) that is fused to the ELP and CPP (e.g., fusion protein including a TP, an ELP and a CPP). In some embodiments, the CPP, the ELP, and the TP are provided as a fusion protein, wherein the CPP, the ELP, and the TP are all fused directly to one another. In some embodiments the CPP, the ELP, and the TP are provided as a fusion protein, wherein one or more linkers comprising one or more amino acids is disposed between the CPP, the ELP, and the TP components of the fusion protein. For example, in some embodiments, the amino acid sequence GGCGGCGGC (SEQ ID NO: 41) can be disposed between the ELP and the TP.

In some embodiments, the compound includes an ELP and a TP, which are provided as a fustion protein. In some embodiments, the TP and the ELP are provided as a fusion protein, wherein the TP is fused directly to the ELP. In some embodiments the TP and the ELP are provided as a fusion protein, wherein a linker comprising one or more amino acids is disposed between the TP and the ELP. For example, in some embodiments, the amino acid sequence GGCGGCGGC (SEQ ID NO: 41) can be disposed between the ELP and the TP.

In some embodiments the TP can be a c-Myc inhibitory polypeptide. In some embodiments the TP can be a cyclin-dependent kinase inhibitory polypeptide. In some embodiments, the TP can be selected from the group of polypeptides having the amino acids sequences set forth in SEQ ID NOS: 37-40.

c-Myc, a transcriptional regulator which controls cell growth, proliferation, apoptosis, and tumorigenesis, presents a novel target for cancer therapy. It has been shown that deregulated expression of c-Myc is associated with numerous types of human cancers, confirming its strong oncogenic potential. For its oncogenic activity, c-Myc must dimerize with its partner protein, Max. Consequently, inhibition of c-Myc-Max dimerization appears to be a potent method of inhibiting proliferation of cancer cells and represents an attractive target for tumor therapy. Therefore, a peptide derived from helix 1 (H1) of the helix-loop-helix region of c-Myc (H1-S6A, F8A) which inhibits the c-Myc interaction with Max (1), blocks its transcriptional function, and inhibits proliferation of cancer cells was included in the ELP-based peptide delivery vector.

In some embodiments, the TP is an H1 polypeptide as set forth in SEQ ID NO: 37. The following are nonlimiting examples of embodiments of the compound that include an H1 polypeptide.

In some embodiments, the compound of the present invention can include Tat (SEQ ID NO: 1) an ELP (e.g., SEQ ID NOS: 21 or 22, or another ELP as described herein), and H1 (SEQ ID NO: 37). The Tat peptide has been used to efficiently deliver proteins and therapeutic compounds across the cell membrane and the blood brain barrier (BBB)(2).

In some embodiments, the compound of the present invention can include penetratin (SEQ ID NO: 2) an ELP (e.g., SEQ ID NOS: 21 or 22, or another ELP as described herein), and H1 (SEQ ID NO: 37).

In some embodiments, the compound of the present invention can include Bac7 (SEQ ID NO: 3) an ELP (e.g., SEQ ID NOS: 21 or 22, or another ELP as described herein), and H1 (SEQ ID NO: 37).

In some embodiments, the compound of the present invention can include SynB1 (SEQ ID NO: 4) an ELP (e.g., SEQ ID NOS: 21 or 22, or another ELP as described herein), and H1 (SEQ ID NO: 37).

In some embodiments, the compound of the present invention can include SynB1-NLS (SEQ ID NO: 5) an ELP (e.g., SEQ ID NOS: 21 or 22, or another ELP as described herein), and H1 (SEQ ID NO: 37).

In some embodiments, the compound includes a fusion protein wherein the CPP is directly fused to an ELP, which is directly fused to H1 (SEQ ID NO: 37). For example, in some embodiments, the compound can include fusion protein including the following amino acid sequences directly fused to one another: SynB1-NLS (SEQ ID NO:5)-(VPGXG)$_{40}$ (SEQ ID NO: 44), where X is V:G:A in a ratio of 3:1:1-H1 (SEQ ID NO: 37). For example, in some embodiments, the compound can include fusion protein including the following amino acid sequences directly fused to one another: Bac (SEQ ID NO: 3)-(VPGXG)$_{150}$ (SEQ ID NO: 44), where X is V:G:A in a ratio of 5:3:2-GGCGGCGGC (SEQ ID NO: 41)-H1 (SEQ ID NO: 37).

The polypeptides are able to disrupt the nuclear localization of c-Myc and inhibit transcriptional activation by c-Myc. For example, cell proliferation studies showed that Pen-ELP-H1 inhibits growth of MCF-7 breast carcinoma, OV-CAR-3 ovarian carcinoma, and HeLa cervical carcinoma cells. Furthermore, the use of hyperthermia increased the antiproliferative effect of a thermally responsive Pen-ELP-H1 approximately two fold compared to a non-thermally responsive control polypeptide. Thus, these results for embodiments of the present invention results demonstrate that compounds of the present invention are a new way to thermally target specific oncogene inhibitors to solid tumors.

Sequential activation of cyclin/Cdk complexes regulates progression through the cell cycle (4, 5). These proteins regulate proliferation during normal development and differentiation, and after genotoxic stress. The p21 protein is the founding member of the Cip/Kip family of cyclin dependent kinase inhibitor proteins, and it plays an essential role in growth arrest after DNA damage (6, 7). p21 inhibits cyclin/Cdk complexes, and its overexpression leads to $G_1$ and $G_2$ (8) or S-phase (9) arrest. Applicants have designed cyclin dependent kinase inhibitory polypeptides which retard cell growth and inhibit cancer cell proliferation. These polypeptides consist of a cell penetrating peptide, ELP, and the p21(Waf1/Cip1) carboxyl-terminal WP10 peptide (p21), which exhibits cyclin-dependent kinase-inhibitory activity and cytotoxicity when introduced into human cells (10). Three examples of compounds of the present invention are below.

In some embodiments, the TP is an p21 polypeptide as set forth in SEQ ID NO: 38. The following are nonlimiting examples of embodiments of the compound that include a p21 polypeptide.

In some embodiments, the compound of the present invention can include Tat (SEQ ID NO: 1) an ELP (e.g., SEQ ID NOS: 21 or 22, or another ELP as described herein), and p21 (SEQ ID NO: 38).

In some embodiments, the compound of the present invention can include penetratin (SEQ ID NO: 2) an ELP (e.g., SEQ ID NOS: 21 or 22, or another ELP as described herein), and p21 (SEQ ID NO: 38).

In some embodiments, the compound of the present invention can include Bac7 (SEQ ID NO: 3) an ELP (e.g., SEQ ID NOS: 21 or 22, or another ELP as described herein), and p21 (SEQ ID NO: 38).

In some embodiments, the compound of the present invention can include SynB1 (SEQ ID NO: 4) an ELP (e.g., SEQ ID NOS: 21 or 22, or another ELP as described herein), and p21 (SEQ ID NO: 38).

In some embodiments, the compound of the present invention can include SynB1-NLS (SEQ ID NO: 5) an ELP (e.g., SEQ ID NOS: 21 or 22, or another ELP as described herein), and p21 (SEQ ID NO: 38).

In some embodiments, the compound includes a fusion protein wherein the CPP is directly fused to an ELP, which is directly fused to p21 (SEQ ID NO: 38). For example, in some embodiments, the compound can include fusion protein including the following amino acid sequences directly fused to one another: SynB1-NLS (SEQ ID NO:5)-(VPGXG)$_{40}$ (SEQ ID NO: 44), where X is V:G:A in a ratio of 3:1:1-p21 (SEQ ID NO: 38).

For another example, in some embodiments, the compound can include fusion protein including the following amino acid sequences directly fused to one another: SynB1-NLS (SEQ ID NO:5)-(VPGXG)$_{150}$ (SEQ ID NO: 44), where X is V:G:A in a ratio of 5:3:2-p21 (SEQ ID NO: 38).

For another example, in some embodiments, the compound can include fusion protein including the following amino acid sequences directly fused to one another: SynB1-NLS (SEQ ID NO:5)-(VPGXG)$_{300}$ (SEQ ID NO: 44), where X is V:G:A in a ratio of 5:3:2-p21 (SEQ ID NO: 38).

For another example, in some embodiments, the compound can include fusion protein including the following amino acid sequences directly fused to one another: MPG (SEQ ID NO: 17)-(VPGXG)$_{150}$ (SEQ ID NO: 44), where X is V:G:A in a ratio of 5:3:2-p21 (SEQ ID NO: 38).

In some embodiments, the TP is a KLAK polypeptide as set forth in SEQ ID NO: 39. The following are nonlimiting examples of embodiments of the compound that include a KLAK polypeptide.

In some embodiments, the compound of the present invention can include Tat (SEQ ID NO: 1) an ELP (e.g., SEQ ID NOS: 21 or 22, or another ELP as described herein), and KLAK (SEQ ID NO: 39).

In some embodiments, the compound of the present invention can include penetratin (SEQ ID NO: 2) an ELP (e.g., SEQ ID NOS: 21 or 22, or another ELP as described herein), and KLAK (SEQ ID NO: 39).

In some embodiments, the compound of the present invention can include Bac7 (SEQ ID NO: 3) an ELP (e.g., SEQ ID NOS: 21 or 22, or another ELP as described herein), and KLAK (SEQ ID NO: 39).

In some embodiments, the compound of the present invention can include SynB1 (SEQ ID NO: 4) an ELP (e.g., SEQ ID NOS: 21 or 22, or another ELP as described herein), and KLAK (SEQ ID NO: 39).

In some embodiments, the compound of the present invention can include SynB1-NLS (SEQ ID NO: 5) an ELP (e.g., SEQ ID NOS: 21 or 22, or another ELP as described herein), and KLAK (SEQ ID NO: 39).

In some embodiments, the compound includes a fusion protein wherein the CPP is directly fused to an ELP, which is directly fused to KLAK (SEQ ID NO: 39). For example, in some embodiments, the compound can include fusion protein including the following amino acid sequences directly fused to one another: SynB1 (SEQ ID NO: 4)-(VPGXG)$_{150}$ (SEQ ID NO: 44), where X is V:G:A in a ratio of 5:3:2-KLAK (SEQ ID NO: 39).

In some embodiments, the TP is a KLAK polypeptide as set forth in SEQ ID NO: 40. The following are nonlimiting examples of embodiments of the compound that include a p50 polypeptide.

In some embodiments, the compound of the present invention can include Tat (SEQ ID NO: 1) an ELP (e.g., SEQ ID NOS: 21 or 22, or another ELP as described herein), and p50 (SEQ ID NO: 40).

In some embodiments, the compound of the present invention can include penetratin (SEQ ID NO: 2) an ELP (e.g., SEQ ID NOS: 21 or 22, or another ELP as described herein), and p50 (SEQ ID NO: 40).

In some embodiments, the compound of the present invention can include Bac7 (SEQ ID NO: 3) an ELP (e.g., SEQ ID NOS: 21 or 22, or another ELP as described herein), and p50 (SEQ ID NO: 40).

In some embodiments, the compound of the present invention can include SynB1 (SEQ ID NO: 4) an ELP (e.g., SEQ ID NOS: 21 or 22, or another ELP as described herein), and p50 (SEQ ID NO: 40).

In some embodiments, the compound of the present invention can include SynB1-NLS (SEQ ID NO: 5) an ELP (e.g., SEQ ID NOS: 21 or 22, or another ELP as described herein), and p50 (SEQ ID NO: 40).

In some embodiments, the compound includes a fusion protein wherein the CPP is directly fused to an ELP, which is directly fused to p50 (SEQ ID NO: 40). For example, in some embodiments, the compound can include fusion protein including the following amino acid sequences directly fused to one another: SynB1 (SEQ ID NO: 4)-(VPGXG)$_{150}$ (SEQ ID NO: 44), where X is V:G:A in a ratio of 5:3:2-p50 (SEQ ID NO: 40).

Additional examples of TPs that can be included in compounds of the present invention include, but are not limited to, those set forth in Table 1 (below).

These polypeptides were shown to inhibit proliferation of the human ovarian cancer cell line SKOV-3, the human cervical carcinoma cell line HeLa, and the human pancreatic cell line Panc-1 by slowing their growth rate and inducing apoptosis. The use of hyperthermia further increases the antiproliferative effect, indicating that the designed polypeptides may be used to thermally target and deliver cell cycle inhibitory and other therapeutic polypeptides to specific heated sites.

As will be recognized by those skilled in the art upon studying the present document, with reference to the specific examples of polypeptides that can be used in accordance with the presently-disclosed subject matter, one or more amino acids can be added to and/or one or more amino acids can be removed from and/or conservative substations of one or more amino acids can be made as compared to the exemplary sequences set forth herein to obtain additional embodiments of the presently-disclosed subject matter. With regard to removing and/or making a conservative substitution of one or more amino acids relative to the specific examples of CPPs and ELPs as set forth herein, consideration to cell binding efficacy, and aggregation efficacy should be considered.

A "conservative substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another.

As will be recognized by those skilled in the art upon studying the present document, compounds as described herein can be made using standard molecular biology techniques.

As used herein, the term "subject" includes both human and animal subjects. Thus, veterinary therapeutic uses are provided in accordance with the presently disclosed subject matter. As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

In some embodiments a compound of the present invention can be formulated by purifying the polypeptide from cultured bacterial cells grown in culture flasks or a bioreactor. Once purity of the polypeptide agent is insured, it will be formulated for injection by dissolving it in the appropriate amount of physiological saline to produce an injection of the proper dose and volume for administration, which can vary depending on the administration route used as outlined herein.

Conventional methods, known to those of ordinary skill in the art of medicine, can be used to administer effective amounts of the compound in a suitable formulation to a subject. Suitable methods for administering embodiments of the compound of the present invention in accordance with the methods of the present invention include but are not limited to systemic administration, parenteral administration (including intravascular, intramuscular, intraarterial, intraperitoneal administration), oral delivery, buccal delivery, subcutaneous administration, inhalation, intratracheal installation, surgical implantation, transdermal delivery, local injection, and hyper-velocity injection/bombardment.

The particular mode of drug administration used in accordance with the methods of the present invention depends on various factors, including but not limited to the severity of the condition to be treated.

The term "effective amount" is used herein to refer to an amount of the compound sufficient to produce a measurable biological response. Actual dosage levels of the compound in an appropriate formulation can be varied so as to administer an amount of the compound that is effective to achieve the desired response for a particular subject and/or application. The selected dosage level will depend upon a variety of factors including the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of an effective dose, as well as evaluation of when and how to make such adjustments, are known to those of ordinary skill in the art of medicine and can be determined in a particular case by one skilled in the art using only routine experimentation.

Figure 2:
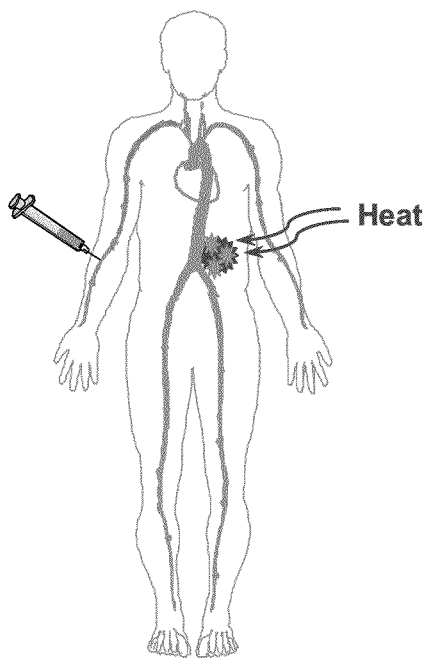
FIG. 2 depicts an aspect of the present invention. Intravenously delivered therapeutic ELP (green) are likely to have low blood concentration, and they will be rapidly cleared under physiological conditions ($T<T_t$). However, they will aggregate at heated sites (red colored area) where $T>T_t$, allowing preferential accumulation of the therapeutic peptide.

Aspects of the present invention include a therapeutic peptide delivery molecule which has the potential to be targeted to a specific (tumor) site by applying local hyperthermia. This compound is soluble under physiological conditions ($T<T_t$), and it is likely to be cleared from circulation under these conditions, i.e., when hyperthermia has not been applied to the target, the compound will have a lower blood concentration and will be rapidly cleared under physiological conditions, wherein $T<T_t$, where T is the temperature of the target, and $T_t$ is the transition temperature of the ELP. However, it will aggregate at sites where heat is applied ($T>T_t$), which will allow preferential accumulation of the therapeutic polypeptide only at the targeted, locally heated diseased sites (FIG. 2).

In some embodiments, the present invention includes a method of treating a condition of interest in a subject, including administering to the subject an effective amount of a compound of the present invention, as described herein, and applying local hyperthermia to a target site. A therapeutic polypeptide can be designed and/or selected for efficacy, e.g., a known efficacy. As will be recognized by those skilled in the art, in some embodiments, the selected therapeutic polypeptide (TP) can attached to the ELP, or the ELP and CPP. In some embodiments, multiple TPs can be selected for use in the presently-disclosed composition.

As used herein, the terms "treatment" or "treating" relate to any treatment of a condition of interest (i.e., condition that can be treated based on the therapeutic peptide (TP) that is selected), including but not limited to prophylactic treatment to prevent development or reduce severity of the condition. As such, the terms treatment or treating include, but are not limited to: preventing a condition of interest or the development of a condition of interest; inhibiting the progression of a condition of interest; arresting or preventing the development of a condition of interest; reducing the severity of a condition of interest; ameliorating or relieving symptoms associated with a condition of interest; and causing a regression of the condition of interest or one or more of the symptoms associated with the condition of interest.

The presently-disclosed subject matter further includes a pharmaceutical composition, including the composition as described herein, and also including at least one component selected from the group consisting of: a pharmaceutically acceptable carrier, a pharmaceutically acceptable adjuvant, and/or a diluent.

In some embodiments, the compounds of the present invention provide a new modality for targeted delivery of specific oncogene inhibitors. This new delivery system is based on the development of a genetically engineered, thermally responsive biopolymer that exhibits thermal targeting activity when triggered by externally induced, local hyperthermia. Such thermally responsive polypeptides are amenable to molecular design and engineering, are easily and inexpensively produced at high purity and quantity, and may be efficiently targeted and adapted to any cell type or tissue. Specific targeting of the proposed therapeutic polypeptides to solid tumors by local hyperthermia would increase specificity and efficacy of treatment and reduce the cytotoxicity in normal tissues.

Such thermally responsive biopolymers with antiproliferative activity have a great potential in cancer therapy for the targeted treatment of solid tumors. In summary, the polypeptide-mediated therapeutic delivery system of the present invention provides an alternative means to effectively substitute or augment present therapy for treatment of localized tumors.

Improvements are necessary in the current therapy for solid tumors. Surgical resection, followed by chemotherapy and/or radiotherapy, are the most common therapeutic modalities used to treat many localized tumors (11-14). However, current treatment of localized tumors is limited by normal tissue tolerance and/or inherent tumor resistance to radiation or chemotherapy, resulting in a low therapeutic index. In most cases, only a small fraction of the administered dose of drug reaches the tumor site, while the rest of the drug is distributed throughout the body, resulting in undesirable damage to normal tissue when used in doses required to eradicate cancer cells. To make chemotherapy more effective and less toxic, site-specific drug delivery vehicles would increase the amount of drug reaching the intended target and simultaneously reduce the nonselective cytotoxicity. Therefore, it is necessary to consider alternative targeted therapeutic approaches for localized tumors that increase the specificity and efficacy and reduce the cytotoxicity in normal tissues.

Although many different systems such as low molecular weight prodrugs, liposomes, and micro- and nano-particles have been developed (15-18) to treat solid tumors, there are specific advantages in combining macromolecular carriers with focused hyperthermia of tumors. First, soluble polymeric carriers are attractive for systemic drug delivery because polymer-drug conjugates preferentially accumulate in tumors due to their enhanced microvascular permeability and retention (19-22), and exhibit significantly lower systemic toxicity compared to free drug (23-25). Studies have shown that water soluble polymer carriers can overcome multidrug resistance (26-29). The most compelling evidence for the advantages of using polymer-drug conjugates over free chemotherapeutic agents for the treatment of cancer comes from extensive preclinical and clinical studies by Kopecek and colleagues on the use of N-(2-hydroxypropyl)methacrylamide copolymers as drug carriers ((30, 31) and references within). Second, hyperthermia preferentially increases the permeability of tumor vasculature compared to normal vasculature, which can further enhance the delivery of drugs to tumors (32-34). Hyperthermia has been introduced in the treatment of glioblastoma, head and neck cancer, breast cancer, cancer of the gastrointestinal or urogenital tract, and sarcoma (reviewed in (35-37)). Superficial tumors are heated by means of antennas or applicators emitting radiowaves or microwaves placed on tumor surfaces with a contacting medium. Multiantenna applicators are used to heat deep-seated tumors, such as tumors located in the pelvis or abdomen. With recent significant improvement in the control of power-density, temperature distribution and treatment monitoring by magnetic resonance tomography, which can characterize temperature as well as perfusion, it is possible to heat only a limited and specific tumor area and minimize the effects of non-specific toxicity. Consequently, the methods and techniques necessary to employ thermal targeting of thermally sensitive polypeptides are available in the clinical setting. Therefore, the effect of hyperthermia combined with the therapeutic effect of a polymeric drug carrier might offer further synergistic advantages in treatment of localized tumors.

The development of therapeutic peptides has advanced rapidly because these molecules have such diverse activity and show great promise as targeted drugs. An inherent limitation of bioactive peptides is their relative instability, and delivering a therapeutic dose proves challenging. As the field of peptide therapy grows, much attention is being focused on peptide delivery using macromolecular carriers. Micro- and nanospheres are being investigated for their ability to deliver bioactive peptides via the oral route, stabilizing and delivering them through absorption barriers in the gastrointestinal tract (38). However, nanoparticles do not offer the possibility of thermal targeting. Liposomes have emerged as a major class of macromolecular carriers for drug delivery (39). Liposome—peptide conjugates have been investigated, but the focus of this field is the conjugation of cell penetrating peptides to the surface of liposomes to enhance fusion with the cell membrane (40). The use of liposomes to deliver therapeutic peptides, though promising, has not been adequately researched. Thermosenstive liposomes are a technological innovation that employ lipid components with thermal sensitivity in the physiological temperature range (41). Upon application of hyperthermia, the lipid membrane undergoes a phase transition and becomes more permeable, thus releasing drug that has been loaded inside. This approach has been used successfully to deliver chemotherapeutic drugs such as methotrexate, cisplatin, doxorubicin, and bleomycin to solid tumors in animal models (reviewed in (41). However, because this approach requires diffusion of the drug out of the liposome under hyperthermic conditions, it is limited to delivery of small and relatively hydrophobic molecules. Therapeutic peptides are too large and hydrophilic to escape the liposomes, even under conditions of hyperthermia. Given the limitations of other macromolecular carriers for thermally targeted peptide delivery, the Elastin-like polypeptide is an optimized peptide delivery vehicle.

While previous studies investigated cross linked hydrogels (42, 43), micro or nanoparticles (44, 45) or liposomes (46) which are designed to release entrapped drugs in response to the lower critical solution temperature (LCST) transition, our research is focused on the feasibility of using soluble, thermally responsive polypeptide conjugates for targeted delivery to solid tumors in combination with focused hyperthermia of tumors. The significant advantage of these polypeptides over other thermally sensitive carriers, such as temperature sensitive liposomes (41), is that accumulation of the drug on the target tissue occurs through the LCST transition of the carrier rather than through heat triggered release of the drug. Unlike for other delivery systems, a concentration gradient is therefore not required to drive thermally responsive polypeptides into the heated tumor. Even when their blood concentration is less than the total concentration in the tumor, thermally responsive polypeptides continue to accumulate because of aggregation in the heated tumor and alteration of its parent form. Therefore, the therapeutic polypeptide may be injected at a low concentration systemically, while still achieving a higher concentration in the tumor. Given the limitations of other macromolecular carriers for thermally targeted peptide delivery, Elastin-like polypeptide has an advantage over existing carriers, and it has potential to be an efficient, targeted therapeutic peptide delivery vehicle.

While classical approaches rely on chemical conjugation of carriers to therapeutic molecules, we introduce a therapeutic peptide using simple molecular biology techniques. For example, the coding sequence for ELP is modified by addition of the cell penetrating peptide (CPP) penetratin, a peptide sequence known for its ability to mediate cellular uptake of large proteins (2, 47). H1, a peptide that inhibits c-Myc transcriptional function and consequently inhibits cell proliferation (48) is also added to this construct. As a result, the c-Myc inhibitory peptide will be more effective in inhibiting transcription and cell growth in cancerous cells that overexpress c-Myc. Our experiments have shown that inhibition of cell proliferation by the H1 peptide is dependent on the target cell's c-Myc expression level. Cells which express larger quantities of c-Myc are inhibited more potently. This result is encouraging, because normal tissue, which likely expresses less c-Myc than tumor tissue, may be spared toxicity while tumor cell proliferation is specifically inhibited. In summary, in addition to specificity due to thermal targeting, the designed ELP polymer is specific for its intracellular target, providing an additional advantage over classical chemotherapeutic drugs.

The present inventors also have also demonstrated that compounds of the present invention can be used to deliver therpaetuic peptides (TP) (e.g., H1, p21, and See Table 1) to the nucleus of a cell by adding the particular CPPs to the compound (e.g., addition of the bactenecin peptide at the N terminus of ELP). This is useful, since therapeutic peptides delivered by such modified ELPs display much greater potency in inhibiting cellular proliferation. These findings demonstrate that, by careful selection of the cell penetrating peptide (CPP), it is possible to deliver the ELP carrier to the desired site of molecular action.

The compounds of the present invention can have the following advantages over existing macromolecular carriers: ELPs are thermally responsive and may be targeted to the tumor site by applying local hyperthermia; ELPs can be expressed in *E. coli*, and large quantities of the molecule can be purified by simple thermal cycling (This strategy is not possible when using peptide inhibitors linked to polymers that must be chemically synthesized); because it is genetically encoded, by simply modifying the coding sequence, ELPs can be fused to any new therapeutic polypeptide (This approach circumvents the need for peptide synthesis and chemical conjugation of the peptide and the carrier); ELP can be efficiently targeted and adapted not only to any cell type or tissue, but also, by choice of CPP, they may be targeted to the desired intracellular site of molecular action; the phase transition of the ELP polypeptides can be exploited for use in drug delivery by applying hyperthermia to the tumor site (in some embodiments, the hyperthermia can be focused and/or mild hyperthermia).

An in vitro study by Raucher et al. (49), it was shown that ELP was internalized by several cancer cell lines, and the uptake was increased approximately 2-fold when aggregation of ELP was induced by application of hyperthermia. The authors concluded that the uptake was cell line dependent, and the enhanced uptake seen under hyperthermic conditions was likely due to pinocytosis of 100 nm—sized aggregates of ELP, not micrometer—sized aggregates (49). When applied in vivo, systemically injected ELP remains soluble and freely circulates at normal body temperature. However, at localized sites where hyperthermia is applied to raise the tissue above the ELP's $T_t$, the polypeptide aggregates and accumulates. In a study by Meyer et al. (50), mice bearing SKOV-3 ovarian tumors implanted under a window chamber in the back accumulated 54% more thermally responsive ELP after heating for 50 min as compared to a non-thermally responsive control, as assessed by fluorescence videomicroscopy. Additionally, mice bearing D-45MG glioma tumors implanted subcutaneously in the flank accumulated 34% more thermally responsive ELP after heating, as assessed by radioactive counting. The authors further concluded that 60% of the total increase in ELP uptake with hyperthermia was attributed to ELP aggregation, and 40% of the total increase was due to the physiological effects of hyperthermia (50). More recently, a study by Liu et al. (51) showed that ELP was cleared from mouse circulation in a biexponential manner after intravenous injection, with half lives of 7.32 min and 8.37 h for the two phases. Accumulation of a thermally responsive ELP in FaDu xenografts grown in the flank of these mice increased 1.8 fold compared to unheated tumors and 1.5 fold compared to a thermally non-responsive ELP (52). These results demonstrate that the use of ELP for thermal targeting is promising. However, no data describing the in vivo efficacy of an ELP-fused drug has been published to date. Attachment of drugs to ELP offers the capability to specifically deliver these drugs to the desired tissue by focused application of externally applied hyperthermia. The use of hyperthermia has an added advantage of increasing vessel permeability (53-55). The ELP-based drug delivery system embodiments of the present invention described here combine the advantages of macromolecular delivery, hyperthermia, and thermal targeting.

Dr. Chilkoti was an inventor on a patent that described an observation that ELP may be used for binding compounds for various purposes (U.S. Pat. No. 6,582,926). In this patent "Methods of using bioelastomers," bioelastomers are disclosed for use in methods of binding compounds including immunoassay methods, in biosensors and methods of regenerating biosensors, and in methods for targeting the delivery of a compound to a particular location within animal subjects. Although Dr. Chilkoti speculated in the Description section of his patent that ELP may be used for targeted drug delivery, there is no indication of enablement. Indeed, Chilkoti's group has been trying for several years to establish ELP as a drug delivery vehicle. Chilkoti et al. conjugated ELP with doxorubicin through an acid-labile hydrazone linker to enable release of the drug in the acidic environment of lysosomes (56). Although the ELP-dox conjugate exhibited toxicity in cell culture, a thermal effect was not observed. While this approach relies on chemical conjugation of ELP to therapeutic molecules, the current research introduces a therapeutic peptide using simple molecular biology techniques.

While these results on cell culture toxicity and tumor localization of ELPs are promising, to demonstrate therapeutic efficacy, any targeting modality must successfully overcome transport barriers to drug delivery that are posed by unique structural properties of tumors. The major impediments to drug delivery in solid tumors are: (1) heterogeneous distribution of blood vessels, combined with aberrant branching and tortuosity, which result in uneven and slowed blood flow; and (2) the high permeability of tumor vessels combined with the absence of a functional lymphatic system resulting in an elevated interstitial pressure, which retards convective transport of high MW (>2000 Da) drugs.

To increase the efficacy of drug delivery and overcome these barriers, CPPs were used to introduce the ELP biopolymer into cancer cells grown both in cell culture and in vivo. As discussed above, ELPs are genetically encoded, and synthesis of ELPs by recombinant DNA methods provides precise control over the ELP sequence. The original coding sequence for ELP was modified in order to generate fusion proteins with three CPPs: the penetratin peptide derived from the *Drosophila* transcription factor Antennapedia (57) (abbreviated Antp or Pen), the Tat peptide derived from the HIV-1 Tat protein (58), and the Bac7 peptide derived from bovine neutrophils (59). The penetratin peptide, derived from the homeobox transcription factor Antennapedia, was one of the first known cell penetrating peptides. Joliot et al. (60) reported that the 60 amino acid homeobox domain of Antennapedia was internalized by neuronal cells grown in culture. Shortly thereafter, they proposed the idea of using the homeodomain as a delivery vector for another protein, Rab3, and they demonstrated that the homeodomain-Rab3 fusion was internalized by myoblasts and neurons (61). Derossi et al. (57) examined the cellular internalization of the Antennapedia homeodomain by making various deletion mutants, and they determined that the 16 amino acid segment from the third alpha helix was the minimally required peptide for efficient internalization. It was further demonstrated that this 16 amino acid peptide can traverse lipid bilayers in vitro (62). The penetratin peptide has been widely used for delivery of all sizes and types of macromolecules, and has been shown to enhance the intracellular delivery of antisense oligonucleotides (63), liposomes (64), and even viruses (65). Another commonly used CPP is the Tat peptide, derived from the Tat protein of HIV-1. Frankel et al. (66) first observed that the HIV-1 Tat protein was taken up by cultured cells. The amino acids 49-57 were later found to be sufficient for membrane binding (58), and amino acids 48-60 were shown to be the minimum necessary unit for cellular uptake (67). The mechanism for cellular uptake of the Tat peptide has been the subject of debate, but the most recent evidence argues for an energy dependent process by which the peptide first binds the outer surface of the plasma membrane through ionic interactions, and then is internalized by a pinocytic endocytosis mechanism (68, 69). Early work with larger fragments of the Tat protein demonstrated the ability to deliver full length proteins into cultured cells, including β-galactosidase, horse radish peroxidase, RNase A, and domain III of *Pseudomonas* endotoxin A (70). Furthermore, these large Tat-based peptides delivered β-galactosidase to the heart, liver, and spleen of mice (70). More recently, the Tat 48-60 peptide has been widely used for the cellular delivery of a wide variety of macromolecules, including proteins such as the Cre recombinase (71), peptide nucleic acids (72), nanoparticles (73), antisense oligonucleotides (63), liposomes (74), and synthetic polymers (75-78). The Tat delivery technology has also been successful in various in vivo applications. A Tat-β-galactosidase fusion protein was shown to distribute to all tissues in mice, including the brain (79). A fusion of Tat and the enzyme purine nucleoside phosphorylase (PNP) distributed into several tissues and replaced PNP activity for a sustained time period in PNP knockout mice (80). When Tat was fused to the super-repressor IκBa and injected into Wistar rats, the fusion protein blocked activation of NF-κB in leukocytes and diminished the infiltration of leukocytes to the site of inflammation (81). An interesting fusion protein of Tat to the apoptosis inhibitor Bcl-XL protected retinal ganglion cells from apoptosis when injected intraocularly (71). The final CPP utilized in this study is Bac7. The Bac7 peptide was first purified from bovine neutrophils due to interest in its use as an antimicrobial agent (59). More recently, it was published that amino acids 1-17 and 46-59 bind acidic phospholipids (82), and amino acids 1-24 were shown to be cell permeable (83). Sadler et al. (83) further concluded that the Bac7 1-24 peptide traversed the cell membrane and resided inside the nucleus of murine monocytes, and they first demonstrated the peptide's use as a cell penetrating peptide. A biotinylated version of the Bac7 1-24 peptide was capable of enhancing the uptake of avidin over 10 fold in murine monocytes as compared to avidin alone. This work was extended recently by Tomasinsig et al. (3), who found that a peptide composed of amino acids 1-35 of Bac7 was taken up by 3T3 and U937 cells in a non-toxic, energy and temperature dependent manner. However, to date, there is little data other than the avidin experiment described above on the ability of Bac7 to deliver large cargo to the cell interior, and no in vivo evaluation of its efficacy. A previous study evaluated the efficiency and mechanism of several CPPs fused to ELP. Pen, Tat, and the membrane translocating sequence (MTS) from the Kaposi fibroblast growth factor signal peptide (84) were fused to ELP. All CPP-ELP fusions were internalized by HeLa and SKOV-3 cells, with Pen being the most efficient. The CPP-ELPs entered the cells via an endocytic mechanism and localized to the cell cytoplasm (85). The study described here utilized Pen, Tat, and Bac7 as cell penetrating peptides for ELP delivery, and all delivered ELP efficiently into cultured cells. Pen yielded the highest levels of polypeptide in the cells, but Bac7 accumulated in the nucleus of some cells, a property not before seen with any CPP-ELP.

Cell penetrating peptides are known for their ability to mediate cellular uptake of large proteins and macromolecules (reviewed in section F.2.a). The following patents are related to cell penetrating peptides, and are incorporated herein in their entirety: "Modular peptide mediated intracellular delivery system and uses", Zhang, et al Jan. 18, 2005 U.S. Pat. No. 6,844,324, which uses the penetratin peptide to enhance delivery of therapeutics; "Carrier based drug delivery system" Peter M. Fischer et al, Jan. 31, 2006, U.S. Pat. No. 6,992,169. This patent describes a system which comprises a drug moiety linked to a carrier moiety wherein the carrier moiety comprises a homeobox peptide or a fragment or its derivative; "Tat-derived transport polypeptides and fusion proteins". Alan Frankel et al.,: Sep. 8, 1998, U.S. Pat. No. 5,804,604. This invention relates to delivery of biologically active cargo molecules, such as polypeptides and nucleic acids, into the cytoplasm and nuclei of cells in vitro and in vivo. Intracellular delivery of cargo molecules, according to this invention. is accomplished by the use of novel transport polypeptides which comprise the HIV-1 Tat protein or one or more of its segments which are covalently attached to cargo molecules.

Figure 3:
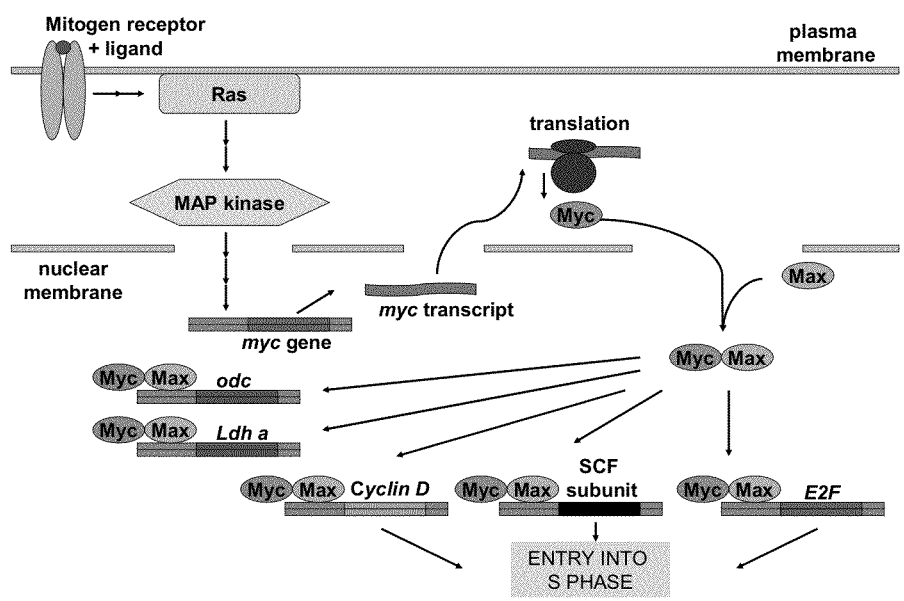
FIG. 3 shows the function of c-Myc. Extracellular signals, such as growth factors bind to the cell surface receptors and activate them. Ras couples the signals of activated growth factor receptors to Ras effectors. Ras effectors activate signaling cascades that induce transcription of mRNA from the c-Myc gene. After translation of the c-Myc protein in the cytoplasm, c-Myc is imported into the nucleus and dimerizes with Max. The c-Myc-Max complex functions as a transcription factor for cell cycle controlling proteins. These proteins stimulate cell entry into S-phase of the cell cycle, which leads to cell proliferation.

Cell proliferation, differentiation and survival are regulated by a number of cellular hormones, growth factors and cytokines in complex organisms. These molecules serve as ligands for cellular receptors and communicate with the nucleus of the cell through a network of intracellular pathways. In cancer cells, deregulated cell signaling and proliferation may occur through overexpression or mutation of proto-oncogenes. There are different proto-oncogene families, and their gene products have different functions and cellular localization. They may function in normal cells in the processes of proliferation, regulation of cellular metabolism through signal transfer, or cell differentiation. The participation of proto-oncogenes in signal transduction offers opportunities for errors, and abnormal growth may result from aberrant oncogene products generating a persistent or excessive growth signal. This growth signal enhances the normally limited proliferative capacity of mammalian cells in culture, forcing them to an immortalized phenotype, which in turn may act as a primary step in tumorigenesis (86).

c-Myc, a transcriptional regulator which controls cell growth, proliferation, apoptosis, and tumorigenesis (FIG. 3) presents a novel target for cancer therapy. Recent progress in X-ray crystallography, NMR, and molecular modeling has provided structural information about many oncogenes and their effectors. Consequently, based on these target structures, peptides have been developed that selectively inhibit specific oncogene signaling pathways by tightly binding and sequestering pathway intermediates.

A peptide derived from helix 1 (H1) of the helix-loop-helix region of c-Myc (H1-S6A, F8A) which inhibits the c-Myc signaling pathway has been characterized by Draeger and Mullen (1). It has been shown that deregulated expression of c-Myc is associated with numerous types of human cancers, confirming its strong oncogenic potential. For its oncogenic activity, c-Myc must dimerize with its partner protein, Max. Consequently, inhibition of c-Myc-Max dimerization appears to be a potent method of inhibiting proliferation of cancer cells and represents an attractive target for tumor therapy.

Giorello et al. (48) have shown that the H1-S6A,F8A peptide was able to block c-Myc activity as a transcription factor and inhibit cell proliferation in MCF-7 cells. In our preliminary study, we incorporated the sequence of this peptide into the gene encoding thermally responsive ELP (CPP-ELP-H1), which will serve as a macromolecular carrier for its delivery.

The p21 inhibitory peptide was first described by Ball et al. They carried out a systematic study to examine a library of synthetic peptides based on the sequence of p21$^{WAF1}$. They assessed the ability of these peptides to interact with and inhibit cyclinD1-CDK4 interaction. They reported that peptides corresponding to the carboxy terminus of p21 show inhibitory effect when introduced into human-keratinocyte-derived HaCaT cells (87). In another study, the N-terminal portion of p21 was fused to the Antennapedia peptide. The fusion peptide showed inhibition of proliferation, but no DNA fragmentation, in human ovarian cancer SKOV-3 and IGROV cells (88).

A separate study showed that the region of p21 comprising amino acids 139-164 was more potent for inhibiting the cyclin D1/CDK4 and cyclin E/CDK2 kinase activity. This study showed the decrease in cell growth of CA46 human lymphoma cells when treated with the p21 peptide fused to the cell penetrating peptide Antennapedia (10). The C-terminal portion of p21 has also been shown to bind to PCNA. Mattock et al. expressed a GFP-p21 miniprotein fusion complex which bound to PCNA and inhibited colony formation of different mammalian cell lines (89).

Khanna et al. treated lymphocytes with full length p21 and observed inhibition in the proliferation of lymphocytes and other transcriptional factors (90). In our previous study, we fused the C-terminal portion of p21 to the Antp-ELP and expressed it as a fusion polypeptide Antp-ELP-p21. It was shown that Antp-ELP-p21 treatment in HeLa and SKOV-3 cells caused inhibition of cell proliferation (85).

Another study showing the potential of Tat to deliver cargo inside the cell attached the PCNA binding doman of p21$^{wAF/CIP}$ to Tat. This Tat-p21 fusion complex was able to decelerate mouse myoblasts cell cycle progression. The authors theorized that inhibition was due to the p21-PCNA interaction, although this hypothesis was not proven (91). In a similar study, Baker et al. conjugated Tat with p21 and showed that it caused a decrease in cell proliferation of U251 (glioblastoma), U373 (astrocytoma), MCF-7 (breast carcinoma), and SW480 (colorectal adenocarcinoma) cells. The authors also showed the colocalization of Tat-p21 with PCNA in the nucleus of the U251 human glioblastoma cells. They further proposed that Tat-p21 disrupted PCNA function and thereby caused cell toxicity by apoptosis (92).

There are several patents describing peptides, derivative peptides, and non-peptidyl mimetics capable of inhibiting cyclin depended kinases which play one of the key roles in controlling cell proliferation, all of which are incorporated herein by reference. (i) Methods and means for inhibition of Cdk4 activity", Ball et al., Nov. 8, 2005 U.S. Pat. No. 6,962,792. The authors report that peptide fragments of p21 inhibit the interaction and/or affect Cdk4 activity. They also claim that the peptides, derivative peptides, and non-peptidyl mimetics of p21 are useful in affecting activity of Cdk4, such as RB phosphorylation and cellular proliferation, indicative of therapeutic usefulness in treatment of tumors and other hyperproliferative disorders. (ii) "Identification of the p21 WaF1-PCNA interaction site and therapeutic applications thereof", Lane et al., Jun. 5, 2001, U.S. Pat. No. 6,242,201. The authors describe peptides that have the property of binding to PCNA: (i) a fragment of the p21 protein including residues 141 to 160 of the p21$^{WAF1}$ amino acid sequence, or an active portion or its derivative; and (ii) functional mimetics of these protein fragments. In particular, the PCNA binding activity is shown to lie within the sequence motif QTSMT-DFY (SEQ ID NO: 43). They claim that these peptides may be useful in the treatments of disorders in which PCNA is implicated, e.g. hyperproliferative disorders such as cancer and psoriasis. (iii) p21$^{WAF1}$ derivatives and diagnostic methods, Kinzler, et al. Feb. 16, 1999, U.S. Pat. No. 5,871,968. The authors report compartmentalization of p21$^{WAF1}$ expression in normal tissues, which is completely abrogated in neoplastic tissues. They also provide methods for using p21$^{WAF1}$ expression as a tool to assess neoplasia and to discover new drugs. Additionally, they reported that a truncated p21$^{WAF1}$ protein is more active than full-length p21$^{WAF1}$ protein in inhibiting cell growth.

While all the findings above are significant, none of them alone can achieve therapeutic usefulness in treatment of tumors and other hyperproliferative disorders. Cell penetrating peptides are capable of penetrating the cell membrane, but they do not have therapeutic properties themselves. ELP is thermally responsive, but it cannot efficiently pass the cell membrane. Therefore, when ELP is coupled to a drug or therapeutic peptide, it cannot effectively kill cells. Inhibitory peptides are small and therefore easily cleared after iv. administration and/or they are rapidly degraded since they are substrates to proteolytic enzymes.

Based on recent findings regarding CPP, ELP and cancer inhibitory peptides, the present inventors have designed and synthesized a novel and unique class of thermally responsive polypeptides which: target a specific site by local application of hyperthermia; penetrate the cell membrane of cancer cells and deliver therapeutic peptides to their intracellular target, and inhibit proliferation and/or slow growth of cancer cells.

Recent progress in X-ray crystallography, NMR, and molecular modeling have provided structural information about many oncogenes and their effectors. Consequently, based on these target structures, peptides have been developed that selectively inhibit specific oncogene signaling pathways by tightly binding and sequestering pathway intermediates.

The present inventors have developed ELP-delivered peptides capable of inhibiting c-Myc oncogene activity and cyclin dependent kinase (cdk) activity (manuscripts enclosed (85, 93)). More specifically, they have shown that inhibition of c-Myc transcription and cdk activity appears to be a potent method of inhibiting proliferation of cancer cells and represents an attractive target for tumor therapy. However, this approach is not limited to c-Myc and cdk inhibition, but it may be applied to any oncogene or molecular target. Simply by modifying the coding sequence, ELP may be attached to any new inhibitory polypeptide. This approach circumvents the need for peptide synthesis and chemical conjugation of the peptide and the carrier. Such biopolymers with capability to modulate intracellular signaling activity would have a great potential for therapeutic interventions.

Recently, small synthetic peptides have been developed that are capable of targeting and inhibiting specific intracellular signaling pathways. Examples of possible peptides which may be delivered by ELP are included, but are not limited to peptides and targets described in Table 2. Such thermally responsive polypeptides, which are amenable to molecular design and engineering, are easily and inexpensively produced at high purity and quantity, and may be efficiently targeted and adapted to any cell type or tissue to further enhance specificity. Specific targeting of the proposed therapeutic polypeptides to solid tumors by local hyperthermia would increase specificity and efficacy of treatment and reduce the cytotoxicity in normal tissues. Thus, the developed polypeptide-mediated therapeutic delivery system would provide an alternative means to effectively substitute or augment present therapy for treatment of localized tumors.

TABLE 2

Examples of TPs that can be included in the compounds of the present invention.

| TP | CPP | Target tumors or cells | References |
| --- | --- | --- | --- |
| Myc peptide | Penetratin | MCF-7 | (1, 94) |
| Retro-inverso Myc peptide | Penetratin | MCF-7 | (95) |
| N-CoR fragments | TAT | APL cells, t(8; 21) AML cells | (96) |
| BCL6-inhibitor peptide | TAT | DLBCL | (97) |
| P53C0 retro-inverso | TAT | Ovarian cancer peritoneal carcinomatosis | (98) |
| Casein kinase II-blocking peptide | TAT | Solid tumors | (99) |
| Phospholipase C gl | TAT | EGFR-positive breast cancer | (100) |
| von Hippel-Landau | TAT | 786-O renal carcinoma cells | (101) |
| RasGAP cleavage fragment | TAT | HeLa, U2OS, MCF7, mesol | (102) |
| Smac5-DIABLO peptide | TAT | Glioblastoma | (103) |
| blocks IAPs | Polyarginine | Lung cancer cell line | (104) |
| STAT3 | Polyarginine | Myeloma | (105) |
| BH3 domain helix | Hydrocarbon-stapled BH3 | Leukemia cell lines | (106) |
| NEMO oligomerization-blocking peptide | Penetratin | Retinoblastoma cells | (107) |
| Survivin Hsp90 binding domain | Penetratin-TAT | Solid tumor cells | (108) |
| AKT single chain antibody | MTS from Kaposi FGF | Solid tumor cells | (109) |
| Aurein 1.2 and 3.1 | (none) | Cell lines from NCI panel | (110) |
| Proapoptotic peptide from Bad | Cpm-1285 | HL 60 cells and human myeloid leukemia | (111) |
| EphA2$_{58}$ and EphA2$_{550}$ for tumor immunotherapy | (none) | COS-7 cells and immunogenic in mice | (112) |
| AHNP anti HER2/neu peptide mimic | (none) | Human cell lines | (113) |
| IKKγ/NEMO Binding Domain (NBD) Inhibitory Peptide | Penetratin | HeLa cells and mouse models of inflammation | (114) |
| p65 (Ser529/536) Inhibitory Peptide | Penetratin | KBM-5 cells | (115) |
| p50 (NLS) Inhibitory Peptide | Penetratin | cultured endothelial and monocytic cells | (116) |
| MyD88 Homodimerization Inhibitory Peptide | Penetratin | HEK293 cells | (117) |
| Akt (Isoforms 1, 2, 3) Inhibitory peptide | TAT | T4 human T cells in vitro and QRsP-11 fibrosarcoma cells in vivo | (118) |
| ERK Inhibitory Peptide | Penetratin and TAT | PC12 and 3T3 cells | (119) |
| Pep27 analogues | (none) | AML-2, HL-60, Jurkat, MCF-7 and SNU-601 cell lines | (120) |
| insect cecropins (CB-1 and CB-2) | (none) | Leukemia cell lines | (121) |
| magainins | (none) | A549 cells in vitro and P388 leukemia, S180 ascites, and a spontaneous ovarian tumor in vivo | (122) |
| Proapoptotic peptide | PTD-5 | MCA205 murine fibrosarcomas and human head and neck tumors | (123) |
| human neutrophil defensins and rabbit defensins | (none) | human (Raji, MOLT-4, K562, IM-9, U-937, and WIL-2) and murine (P815, YAC-1) lines in vitro and murine teratocarcinoma cells in vivo | (124) |

Figure 16:
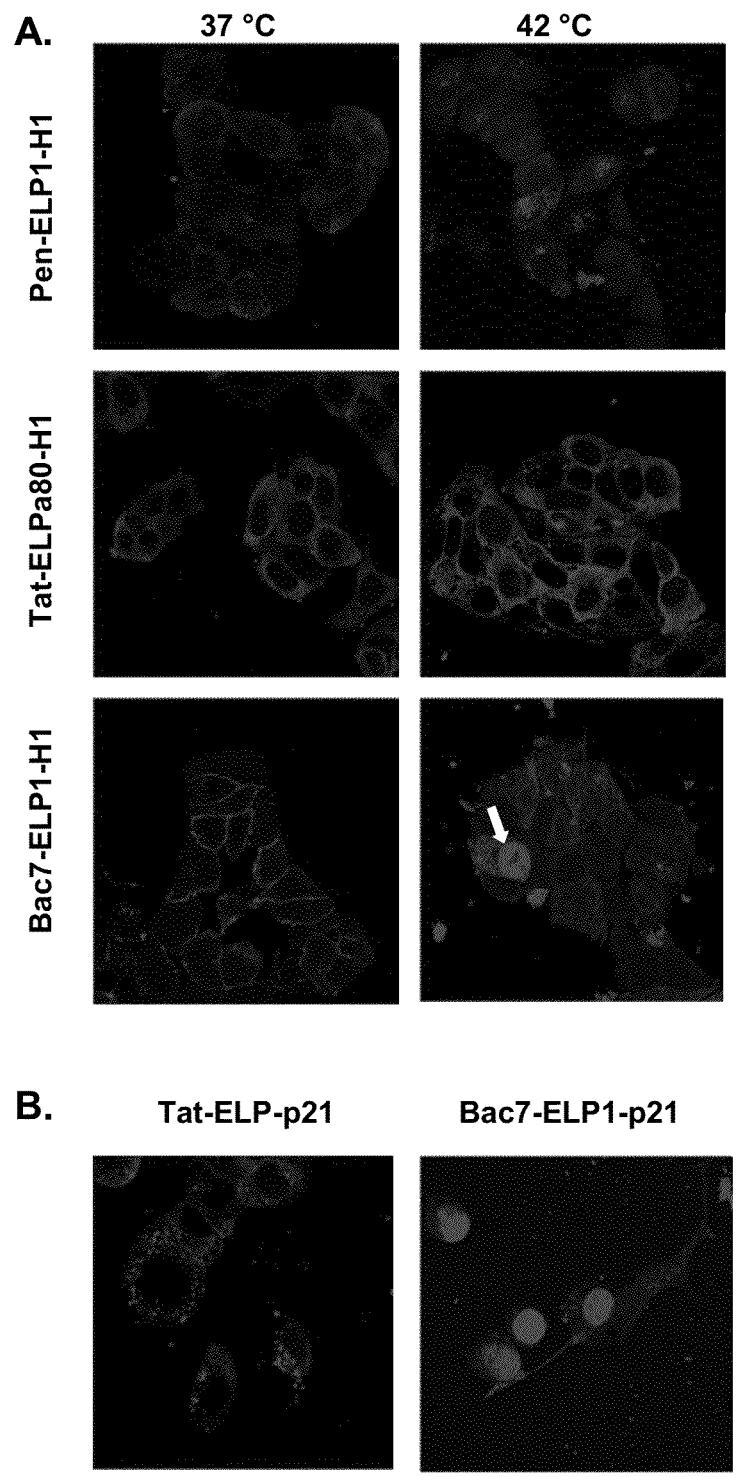
FIG. 16 shows subcellular Localization of ELP-H1 fused to various CPPs. MCF-7 cells (A.) and SKOV-3 cells (B.) were treated for 1 h at 37 or 42° C. with rhodamine labeled polypeptides. Cells were images 24 h after treatment with a laser scanning confocal microscope.

The present inventors have also demonstrated that the compounds of the present invention can be used to deliver the c-Myc inhibitory H1 peptide and the p21 mimetic peptide to the nucleus by adding the bactenecin peptide at the N terminus of ELP (Please see section 1.1.a, FIG. 16). Therapeutic peptides delivered by such modified ELPs display much greater potency in inhibiting cellular proliferation. These findings demonstrate that by careful selection of cell penetrating peptide, it is possible to deliver the ELP carrier to the desired site of molecular action and increase its therapeutic effect.

As stated herein, embodiments of the present invention include thermally responsive polypeptides that inhibit c-Myc transcriptional activity and cyclin dependent kinase activity, and both polypeptides retard cell growth and inhibit cancer cell proliferation. Our goal is to move this technology towards the translational stage of human therapeutics and to apply our invention in the clinical setting. Therefore, it is necessary evaluate these therapeutic polypeptides in an animal model.

EXAMPLES

The following Examples are presented to demonstrate embodiments of the present invention. They should be construed as being exemplary of the present invention, and are not to be construed as being limiting thereof.

The following Examples relate to c-Myc Inhibitory Polypeptides.

Example 1

Delivery of the c-Myc Inhibitory Peptide by Elastin-Like Polypeptide

Design and Thermal Properties of c-Myc Inhibitory Polypeptides

Figure 4:
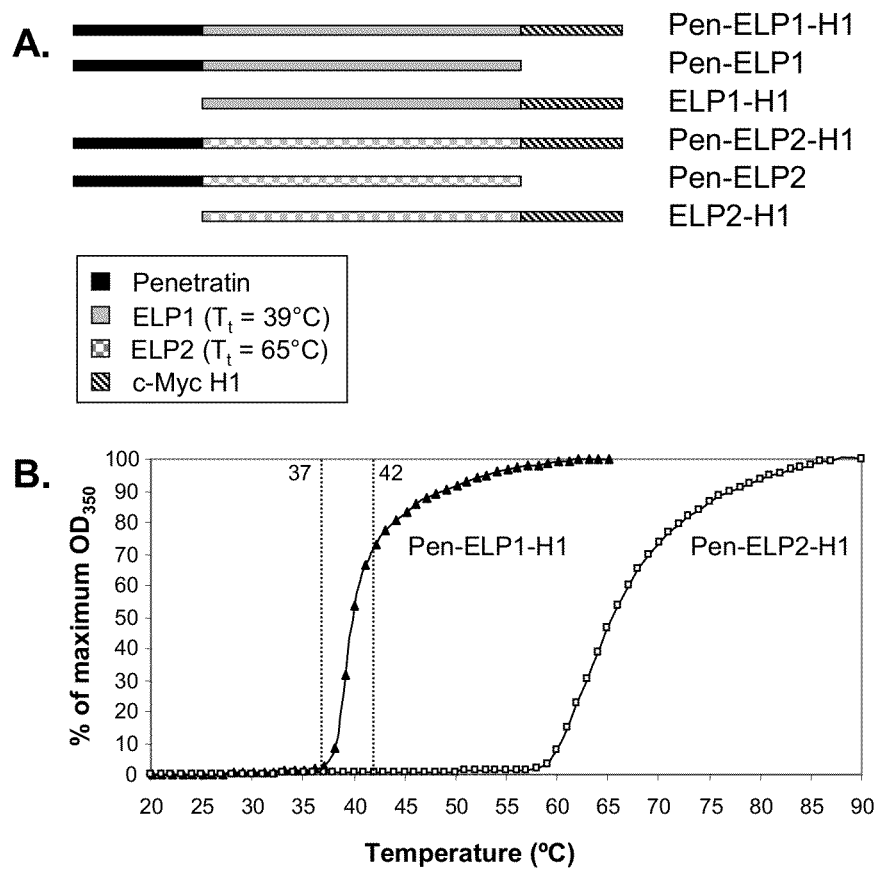
FIG. 4 is a set of graphs showing the design and Thermal Properties of Polypeptides. A. Polypeptides were designed to include the penetrating membrane translocating sequence and the c-Myc inhibitory peptide H1-S6A, F8A. Polypeptides incorporated either the thermally sensitive ELP1 or the non-thermally sensitive ELP2, and control polypeptides lacking either the penetratin sequence or the c-Myc inhibitory sequence were also constructed. B. The turbidity profile (OD350) of Pen-ELP1-H1 (μ) and Pen-ELP2-H1 (μ) were obtained at a heating rate of 1° C./min. The Tt was defined from the heating profile as the temperature at 50% of the maximum turbidity.

The thermally responsive c-Myc inhibitory polypeptides were designed as schematically represented in FIG. 4A. The Pen-ELP1-H1 polypeptide, designed to inhibit c-Myc transcriptional activity, has three components. The first component is a 16 amino acid sequence from the third helix of Antennapedia (penetratin), which is known for its ability to mediate cellular uptake of large proteins (2, 131). The second component is ELP1, which is a thermally responsive polypeptide that undergoes a phase transition, hydrophobically collapses and aggregates at temperatures greater than $T_t$ (50, 132, 133). The $T_t$ of ELP1 was designed to be 39° C., because it is greater than physiological body temperature (37° C.), but lower than temperatures that are clinically applied in focused hyperthermia treatments (35-37). Finally, at the C-terminus a 14 amino acid peptide modified from helix 1 of the helix-loop-helix domain of c-Myc (H1-S6A, F8A) was included, which is capable of preventing c-Myc-Max heterodimerization in vitro (94). Additional polypeptides lacking either Pen or H1 were also made (FIG. 4A).

Thermally unresponsive control polypeptides (Pen-ELP2-H1, Pen-ELP2 and ELP2-H1) were designed to have a $T_t$ greater than the hyperthermia temperature by incorporating the ELP2 polypeptide sequence instead of ELP1. ELP2 has a molecular weight similar to ELP1, but it has a different fraction of Gly and Ala residues at the "guest" position (134).

In response to increasing solution temperature, ELP based polypeptides undergo a hydrophilic to hydrophobic phase transition which results in the formation of polypeptide aggregates (134, 135). Polypeptide aggregates scatter light, causing an increase in turbidity of the polypeptide solution. To characterize the phase transition behavior of these polypeptides, the turbidity of polypeptide solutions was monitored as a function of temperature. As shown in FIG. 4B, a solution of Pen-ELP1-H1 is clear below $T_t$, but becomes turbid upon heating above its $T_t$ because of polypeptide aggregation. The sharp increase in the turbidity upon reaching $T_t$ shows that polypeptide aggregation is initially very rapid with respect to temperature, with 75% of the polypeptide aggregated at the hyperthermia temperature ($T_h$=42° C.). In contrast to Pen-ELP1-H1, the turbidity profile of Pen-ELP2-H1 shows that the polypeptide solution is clear even above the hyperthermia temperature. It becomes turbid only at a temperature significantly higher than $T_h$ ($T_t$=65° C.), indicating that Pen-ELP2-H1 does not undergo its phase transition when heated to 42° C. Pen-ELP2-H1 is a useful control for the effect of hyperthermia since it remains soluble at temperatures significantly higher than the hyperthermia temperature. All constructs containing ELP1 displayed similar transition curves, as did all ELP2 containing polypeptides. The inverse transition of each polypeptide was reversible (data not shown), which is consistent with previously reported ELP thermal properties (134).

Cellular Uptake and Internalization of Polypeptides

Figure 5:
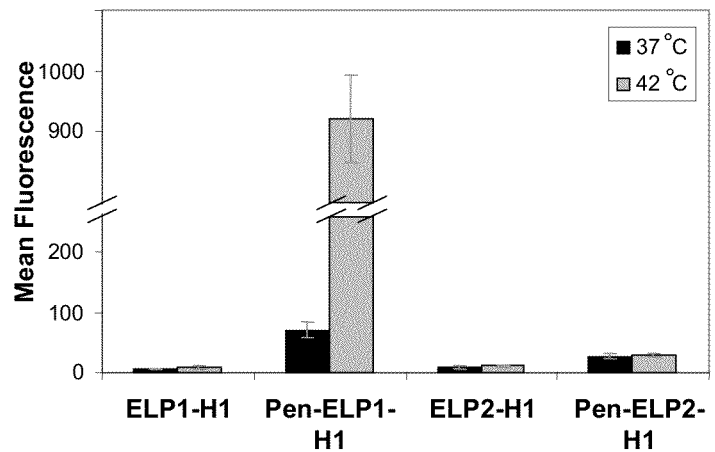
FIG. 5 is a graph that shows cellular Uptake and Internalization of Polypeptides. The effect of penetratin and hyperthermia on polypeptide uptake was determined by flow cytometry. Cells were treated for 1 h at 37° C. or 42° C. with fluorescein labeled polypeptides (18 μM) and analyzed immediately after treatment. Results are expressed as fluorescence relative to standard beads and corrected for labeling efficiency.

In order to reach their intracellular molecular site of action, the polypeptides have to be efficiently internalized by target cells. It has been shown that efficient internalization of relatively large molecules across the cell membrane can be mediated by the penetratin peptide (47, 136). To test whether penetratin can work as an internalization vector for the 60 kDa Pen-ELP-H1 polypeptide, the cellular uptake of fluorescein labeled Pen-ELP-H1 polypeptides was compared with control polypeptides ELP-H1, lacking the penetratin sequence. Cells were incubated with fluorescein labeled polypeptides for one hour, then rinsed and collected. Their fluorescence intensity was measured by flow cytometry. FIG. 5 shows that the fluorescence intensity of cells immediately after a 37° C. incubation with Pen-ELP1-H1-fluorescein or Pen-ELP2-H1-fluorescein is at least three fold greater than in cells incubated with ELP1-H1-fluorescein or ELP2-H1-fluorescein.

Previous studies have shown that cellular uptake of thermally responsive ELP was significantly enhanced by the thermally triggered phase transition of the polypeptide (49). The magnitude of the increase in cellular uptake of ELP polypeptides in response to hyperthermia was also shown to be cell line dependent. To investigate whether hyperthermia enhances the uptake of Pen-ELP-H1 in MCF-7 cells, the fluorescence intensity of Pen-ELP-H1-fluorescein treated cells was measured as a function of solution temperature. As shown in FIG. 5, the uptake of Pen-ELP1-H1 increased thirteen fold when the cells were heated to T>$T_t$, as compared with cells at 37° C. Hyperthermia itself may affect cellular processes including cellular uptake (137). Therefore, it is necessary to discriminate the effect of heat in stimulating the cellular uptake from that of the thermally triggered phase transition of Pen-ELP1-H1. In a control experiment, the uptake of a fluorescein labeled thermally nonresponsive control polypeptide, Pen-ELP2-H1, was assessed with and without hyperthermia As shown in FIG. 5, the uptake of Pen-ELP2-H1 in cells heated to 42° C. was similar to uptake in nonheated cells, indicating that hyperthermia itself does not affect uptake of these polypeptides in cultured cells. In summary, these results demonstrate that the enhanced cellular uptake of thermally responsive Pen-ELP1-H1 in heated cells is not the result of nonspecific effects of hyperthermia, but rather it is attributable to its hyperthermia triggered phase transition.

Intracellular Localization of Polypeptides.

Figure 6:
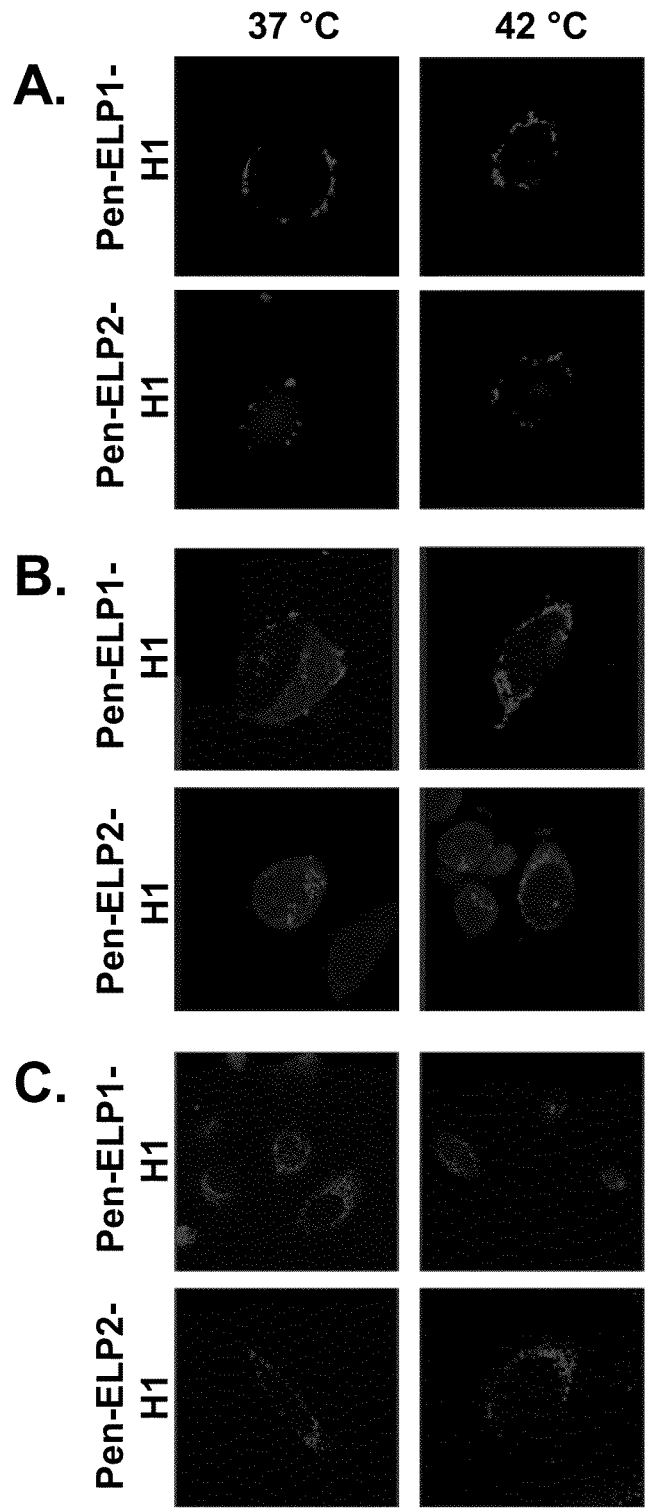
FIG. 6 shows intracellular Localization of Pen-ELP-H1. Subcellular localization of rhodamine labeled Pen-ELP1-H1 and Pen-ELP2-H1 was determined by confocal fluorescence microscopy. MCF-7 cells were incubated with labeled polypeptides (18 μM) for 1 h at 37° C. (left column) or 42° C. (right column). Slides were imaged 1 h (A.), 24 h (B.), and 11 days (C.) after treatment.

In an effort to elucidate the basis of the enhanced uptake of thermally responsive polypeptides and to confirm the internalization results obtained by flow cytometry, the cellular localization of Pen-ELP1-H1 and Pen-ELP2-H1 was examined in heated and nonheated cells. FIG. 6A shows confocal fluorescence images of cells immediately after a one hour incubation with Pen-ELP1-H1-rhodamine (top panel) or Pen-ELP2-H1-rhodamine (bottom panel) at 37° C. (left panel) and 42° C. (right panel). For both polypeptides, regardless of incubation temperature, intense plasma membrane fluorescence was observed, with little or no fluorescent polypeptides in the cytoplasm. The distribution of rhodamine-tagged polypeptides was followed 24 hours later (FIG. 6B). In cells incubated at 37° C., a punctate cytoplasmic distribution of both polypeptides was observed (left panel). When cells were heated to a temperature above $T_t$, a similar distribution was observed for the Pen-ELP2-H1 polypeptide (FIG. 6B, bottom right). The fluorescence image of cells incubated with thermally responsive Pen-ELP1-H1 shows the presence of bright fluorescent areas (FIG. 6B, top right). The observed particles can be attributed to Pen-ELP1-H1 aggregates that are directly internalized by the cells. However, no large aggregates were observed 11 days later (FIG. 6C). These results confirm that immediately after treatment, the polypeptides are only attached to the plasma membrane. However, after 24 hours, almost all of the polypeptides are internalized by the cells.

Figure 7:
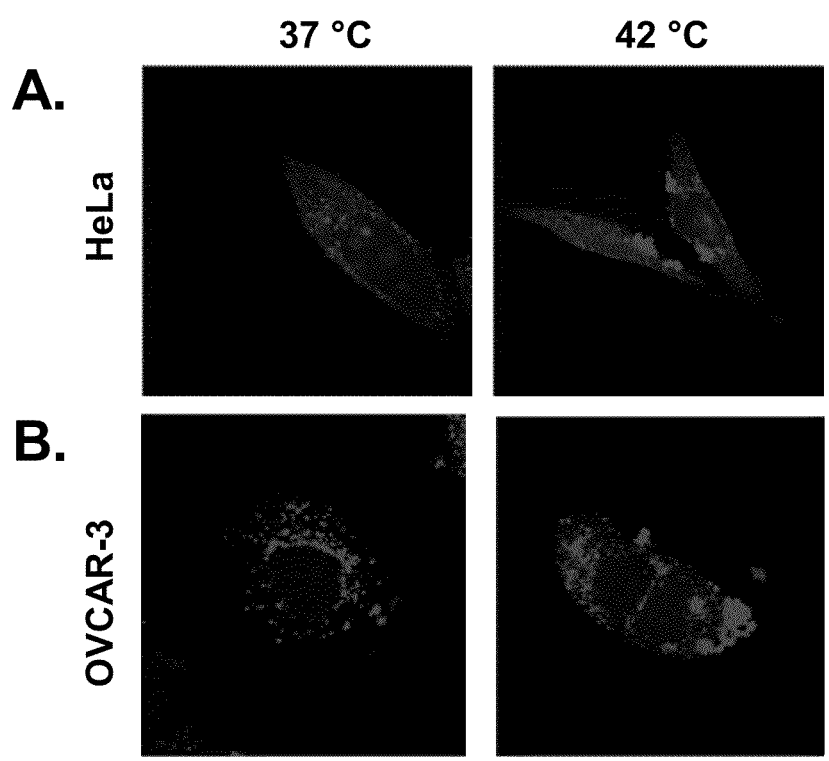
FIG. 7 shows localization of Pen-ELP-H1 in HeLa and OVCAR-3 Cells. HeLa (A.) and OVCAR-3 (B.) cells were treated for 1 h at 37° C. or 42° C. with rhodamine-labeled Pen-ELP1-H1 and imaged after 24 h with a laser scanning confocal microscope.

In order to confirm that the internalization and localization observed with Pen-ELP-H1 was not unique to MCF-7 cells, internalization and cytoplasmic localization was confirmed in HeLa and OVCAR-3 cells. The cells were treated for 1 h at 37 or 42° C. with rhodamine labeled Pen-ELP1-H1 and imaged 24 h later. Punctate cytoplasmic staining was observed for Pen-ELP1-H1 24 h after 37° C. treatment in both cell lines (FIG. 7, left panel). Large aggregates of Pen-ELP1-H1 were observed in the cytoplasm of both cell lines 24 h after hyperthermia treatment (FIG. 7, right panel). Membrane staining was observed 1 h after treatment similar to that seen in MCF-7 cells, and no aggregates were seen in cells treated with Pen-ELP2-H1 (data not shown).

Effect of c-Myc Inhibitory Polypeptides on Cell Proliferation.

Figure 8:
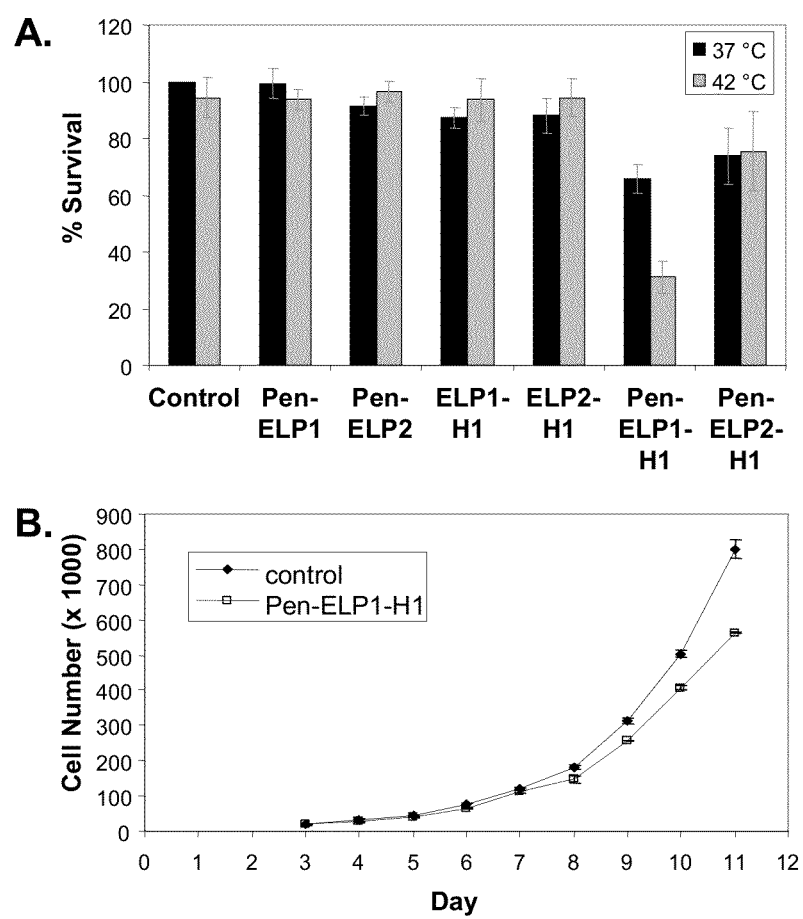
FIG. 8 is a graph that shows an antiproliferative Effect of Pen-ELP-H1 Polypeptides. A. 11 day proliferation of MCF-7 cells after a 1 h, 18 μM polypeptide exposure at 37° C. or 42° C. B. Growth curve of MCF-7 cells after a single 1 h exposure to Pen-ELP1-H1 (18 μM). Cells were counted using the trypan blue dye exclusion assay or a Coulter counter (growth curve). Results represent the mean±SEM of 3-5 experiments performed in duplicate.

In order to examine the antiproliferative effects of these polypeptides, MCF-7 cells were exposed to polypeptides for 1 hour at 37° C. or 42° C. The polypeptides were washed away, and the cells were allowed to grow until day 11, when they were counted using the trypan blue dye exclusion assay. FIG. 8A shows no inhibition of cell growth by polypeptides lacking either the penetratin or the H1 sequences. The thermally sensitive polypeptide Pen-ELP1-H1 inhibited cell proliferation by 35% when cells were treated at 37° C. However, when cells were treated at 42° C., cell growth was inhibited 70%. The antiproliferative effect of the non-thermally responsive polypeptide Pen-ELP2-H1 was temperature independent, and it inhibited cell growth about 25%. These results suggest that the polypeptides exhibit an antiproliferative effect in MCF-7 cells that can be further enhanced by hyperthermia.

FIG. 8B shows growth curves of the MCF-7 cells following a 1 h, 37° C., exposure to Pen-ELP1-H1 or PBS control. Control cells made approximately 6 doublings at day 11. After the same amount of time, Pen-ELP1-H1 treated cells had only doubled approximately 5 times.

Figure 9:
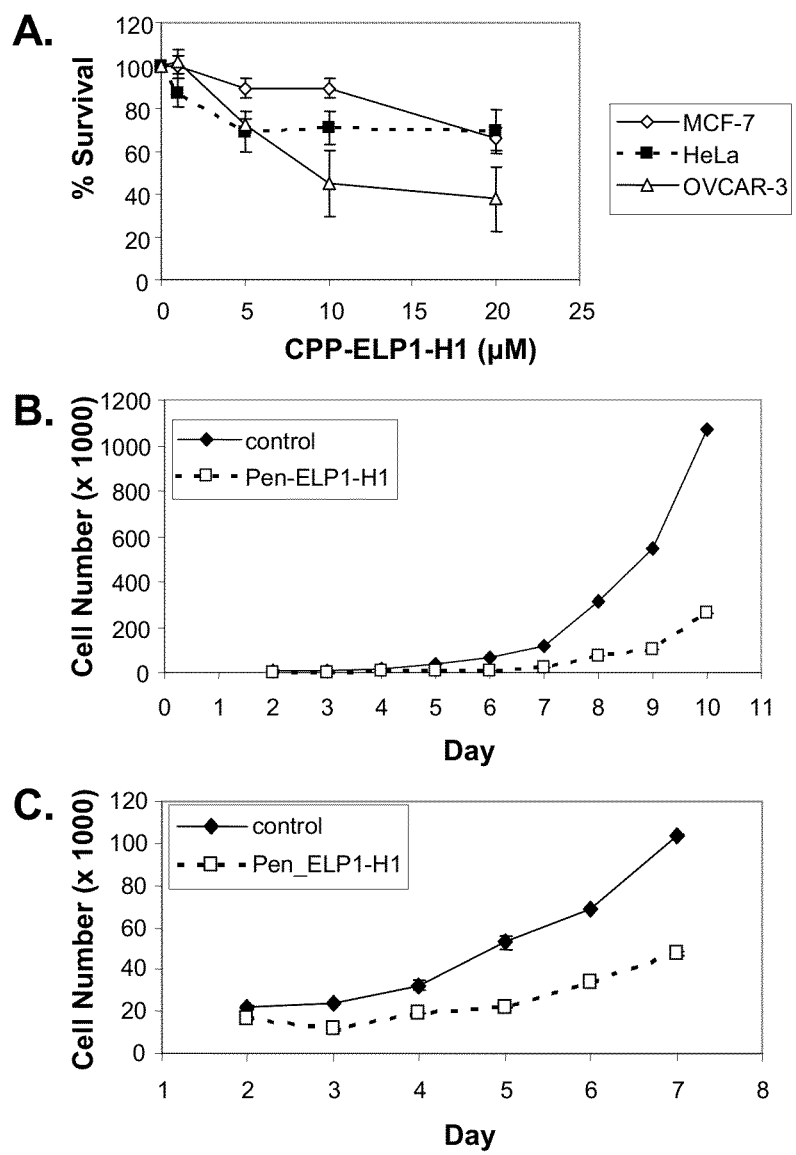
FIG. 9 is a graph that shows an antiproliferative Effect of Polypeptides in HeLa and OVCAR-3 Cells. A. 11 day proliferation of MCF-7, HeLa, and OVCAR-3 cells after a 1 h exposure to Pen-ELP-H1 at 37° C. B. and C. Growth curve of HeLa and OVCAR-3 cells, respectively, after a single 1 h exposure to Pen-ELP-H1 (18 μM). Cells were counted using a Coulter counter. Results represent the mean±SE of 3-5 experiments performed in duplicate.

The effect of Pen-ELP-H1 on cell proliferation was also assessed in HeLa and OVCAR-3 cells. Cells were exposed to Pen-ELP1-H1 for 1 h at 37° C., and the cell number was determined after 11 days. Pen-ELP1-H1 caused a dose-dependent inhibition of proliferation in all three cell lines (FIG. 9A). The magnitude of inhibition was similar in all cell lines, with OVCAR-3 cells being slightly more sensitive to Pen-ELP-H1 than MCF-7 and HeLa cells. Growth curves were also acquired for HeLa (FIG. 9B) and OVCAR-3 (FIG. 9C) cells after a 1 h exposure to Pen-EL1-H1 at 37° C. Pen-ELP-H1 inhibited the growth rate of both cell lines. Furthermore, no apoptosis was observed following exposure to Pen-ELP-H1 (data not shown), indicating that the mechanism by which Pen-ELP-H1 inhibits cell proliferation is likely by slowing doubling time of the cells.

Effect of Pen-ELP-H1 on c-Myc Localization.

Figure 10:
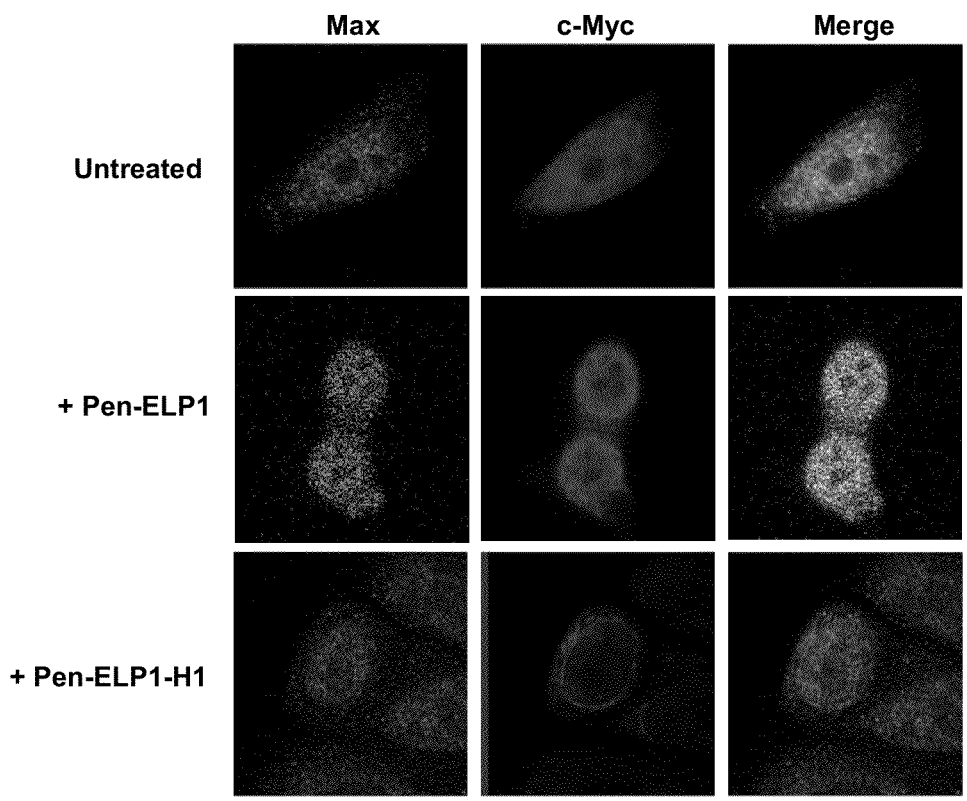
FIG. 10 shows an effect of Pen-ELP1-H1 on c-Myc Localization. The subcellular localization of c-Myc and Max was determined by confocal immunofluorescence microscopy in untreated MCF-7 cells (top row) and in cells treated with 18 μM Pen-ELP1 (middle row) or 18 μM Pen-ELP1-H1 (bottom row) for 1 h. Images were taken 24 h after polypeptide treatment with a 100× oil immersion objective.
Figure 11:
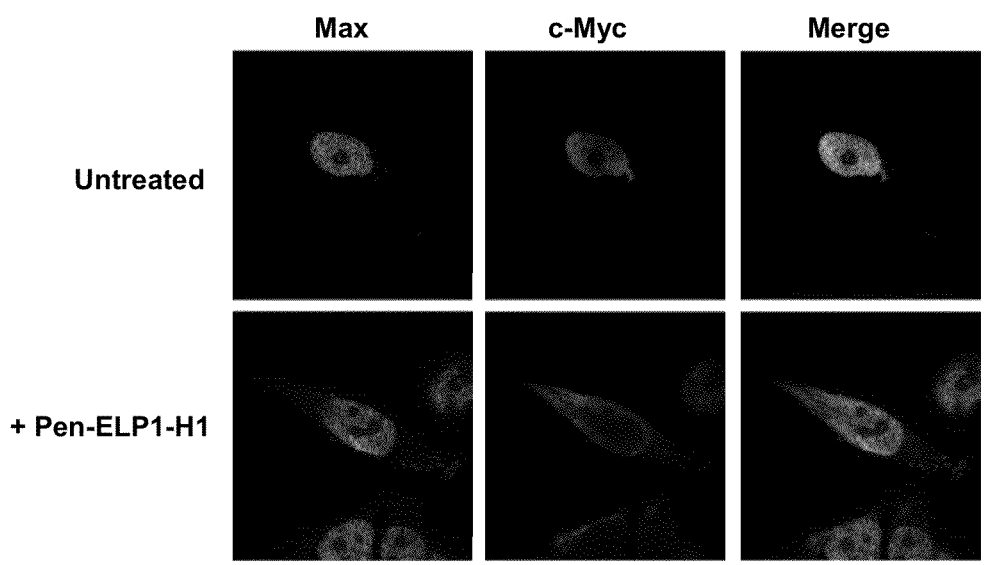
FIG. 11 shows an effect of Pen-ELP1-H1 on c-Myc Localization in HeLa Cells. The subcellular localization of c-Myc and Max was determined by confocal immunofluorescence microscopy in untreated HeLa cells (top row) and in cells treated with 18 μM Pen-ELP1-H1 (bottom row) for 1 h. Images were taken 24 h after polypeptide treatment with a 100× oil immersion objective.

To investigate the mechanism of inhibition of cell proliferation by Pen-ELP1-H1, the cellular localization of c-Myc and its dimerization partner Max was examined by confocal immunofluorescence microscopy in Pen-ELP1-H1 treated and untreated cells. FIG. 10 (upper panel) shows that, in untreated cells, Max displays primarily a nuclear distribution exclusive of nucleoli (FITC channel). A similar distribution is also observed for c-Myc (Cy5 channel), which is consistent with previous studies (138, 139). The overlay of images of Max and c-Myc (upper panel, third figure) shows nuclear colocalization of these two proteins. The localization of c-Myc and Max is unchanged when cells are treated with Pen-ELP1 (middle panel). Treatment of cells with Pen-ELP1-H1 did not change the intracellular distribution of Max (lower panel, first figure). However, Pen-ELP1-H1 treatment caused redistribution of c-Myc from predominantly nuclear to cytoplasmic localization, thus preventing colocalization of Max and c-Myc (lower panel, second and third figures). This effect on c-Myc localization was confirmed in HeLa cells (FIG. 11). c-Myc and Max were colocalized in the nucleus in untreated cells (top panel). However, in cells treated with Pen-ELP-H1, c-Myc was sequestered to the cytoplasm and its interaction with Max was prevented (bottom panel).

Effect of Pen-ELP-H1 on Transcription Activation by c-Myc.

Figure 12:
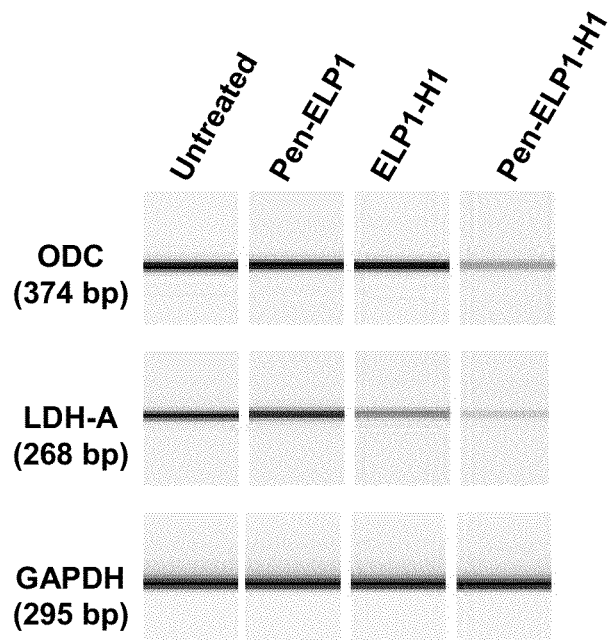
FIG. 12 shows the effect of Pen-ELP1-H1 on c-Myc Transcriptional Activity. The mRNA levels for the c-Myc responsive genes ODC (top panel) and LDH-A (middle panel) and a control gene GAPDH (bottom panel) were assayed by RT-PCR. MCF-7 cells were untreated (lane 1) or treated with 18 µM Pen-ELP1 (lane 2), ELP1-H1 (lane 3), or Pen-ELP1-H1 (lane 4) for 1 h. RNA was purified 48 h after treatment. PCR products were analyzed by capillary electrophoresis using a Bioanalyzer Labchip with fluorescence detection. The fluorescence data was converted to a simulated gel using Agilent software. The experiment was repeated 3 times.

Since c-Myc-Max heterodimerization is required for c-Myc transcriptional activity, blocking the c-Myc-Max interaction may be an effective mode of inhibiting transcription of c-Myc responsive genes. The ability of Pen-ELP1-H1 to inhibit transcription activation by c-Myc was evaluated by assaying the mRNA expression of genes known to be direct targets of c-Myc. c-Myc responsive genes displaying c-Myc-Max binding sites in their promoters include ornithine decarboxylase (ODC) (140) and lactate dehydrogenase-A (LDH-A) (141). Expression levels of ODC and LDH-A mRNA from treated and untreated cells were analyzed by RT-PCR and compared with the expression of glyceraldehyde phosphate dehydrogenase (GAPDH), a gene not regulated by c-Myc. The control polypeptide Pen-ELP1 did not show any inhibition of c-Myc transcriptional activity (FIG. 12, lane 2). The control polypeptide ELP1-H1 also showed no significant effect (lane 3). In contrast, Pen-ELP1-H1 led to a strong decrease in mRNA expression of ODC and LDH-A (lane 4). GAPDH mRNA levels were unaffected by the polypeptide treatments.

Model for Inhibition of Proliferation by Pen-ELP-H1.

Figure 13:
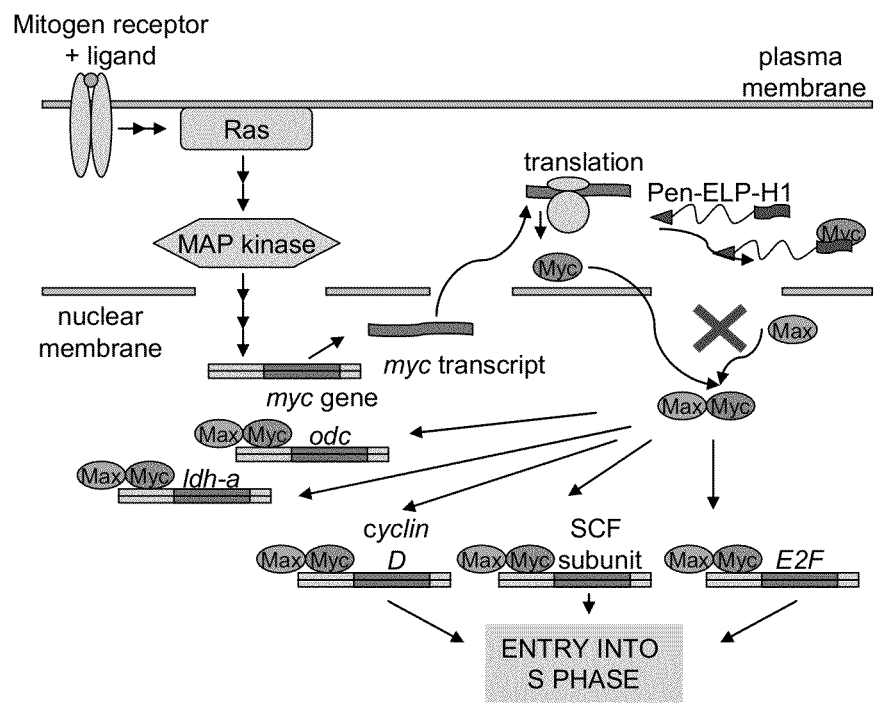
FIG. 13 shows a model for c-Myc Inhibition by Pen-ELP-H1. Mitogen stimulation induces transcription of mRNA from the c-Myc gene. After translation of the c-Myc protein in the cytoplasm, it is bound by the Pen-ELP-H1 polypeptide. Once bound, c-Myc can not be imported into the nucleus and interact with Max. This results in the down-regulation of c-Myc-Max responsive genes and leads to inhibition of cell proliferation.

The redistribution of c-Myc to the cytoplasm and the downregulation of c-Myc controlled genes led to the proposed the model illustrated in FIG. 13. Mitogen-induced cell proliferation stimulates production of c-Myc mRNA. c-Myc protein is translated in the cytoplasm, but before it is imported into the nucleus, it is sequestered by the cytoplasmically localized Pen-ELP-H1. The nascent c-Myc can not enter the nucleus, therefore leaving Max without a binding partner. The result is the down-regulation of c-Myc-Max controlled genes.

The c-Myc protein has a high turnover rate (142), which explains why c-Myc staining is exclusively in the cytoplasm only 24 h after treatment. Without a functional c-Myc-Max heterodimer, the processes of cell growth and cell proliferation are inhibited.

Uptake of the ELP-H1 Polypeptide Fused to Different Cell Penetrating Peptides.

Figure 14:
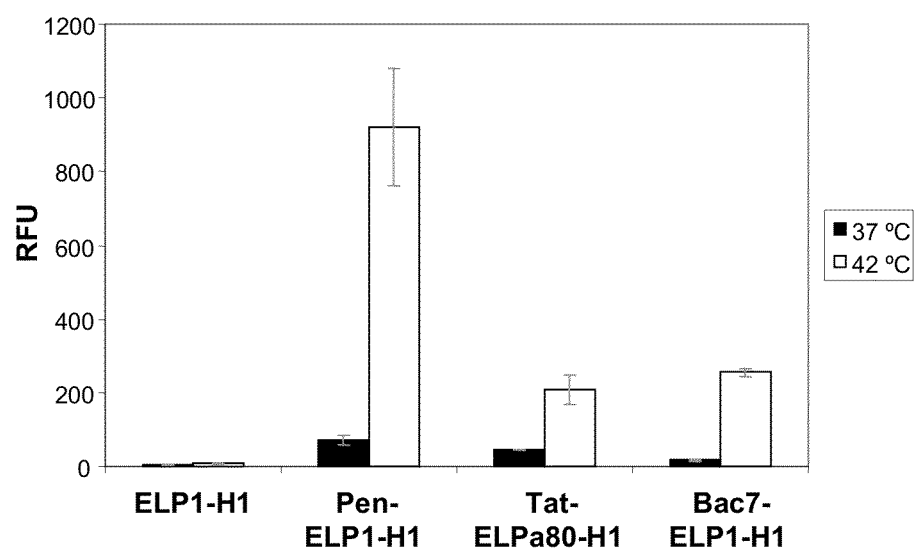
FIG. 14 is a chart that shows cellular uptake of ELP-H1 Fused to Various CPPs. MCF-7 cells were treated for 1 h at 37 or 42° C. with fluorescein labeled polypeptides. Levels of each polypeptide were assessed using flow cytometry (n=5, 000 cells). Data represent the average of 3 experiments; error bars, SEM.

In order to optimize the ELP-based c-Myc inhibitor, different cell penetrating peptides were screened for their ability to enhance the uptake and/or potency of the H1 peptide. The peptides screened included the 7 amino acid Tat peptide derived from the HIV-1 Tat protein (67) and the 24 amino acid Bac7 peptide from the bactenecin antimicrobial peptide (83). The flow cytometry assay described above was used to assess cellular uptake by each polypeptide. When treated at 37° C., Pen was the most efficient peptide for enhancement of uptake, with Tat and Bac7 only slightly less efficient (FIG. 14). When aggregation was induced with hyperthermia treatment, the uptake of Pen-ELP1-H1 was increased 13 fold, the uptake of Tat-ELPa80-H1 was increased 5 fold, and the Bac7-ELP1-H1 uptake was increased 16 fold. However, the total level of polypeptide taken up by the cells under hyperthermia treatment was greatest for Pen-ELP1-H1, with Bac7-ELP1-H1 accumulating 3.6 fold less and Tat-ELPa80-H1 accumulating 4.4 fold less. In summary, all cell penetrating peptides tested substantially increased uptake of the ELP-based polypeptides as compared to ELP-H1 lacking a CPP, and the penetratin peptide was the most efficient for the enhancement of uptake of ELP aggregates, followed by Bac7 then Tat.

Cell Proliferation of the ELP-H1 Polypeptide Fused to Different Cell Penetrating Peptides.

Figure 15:
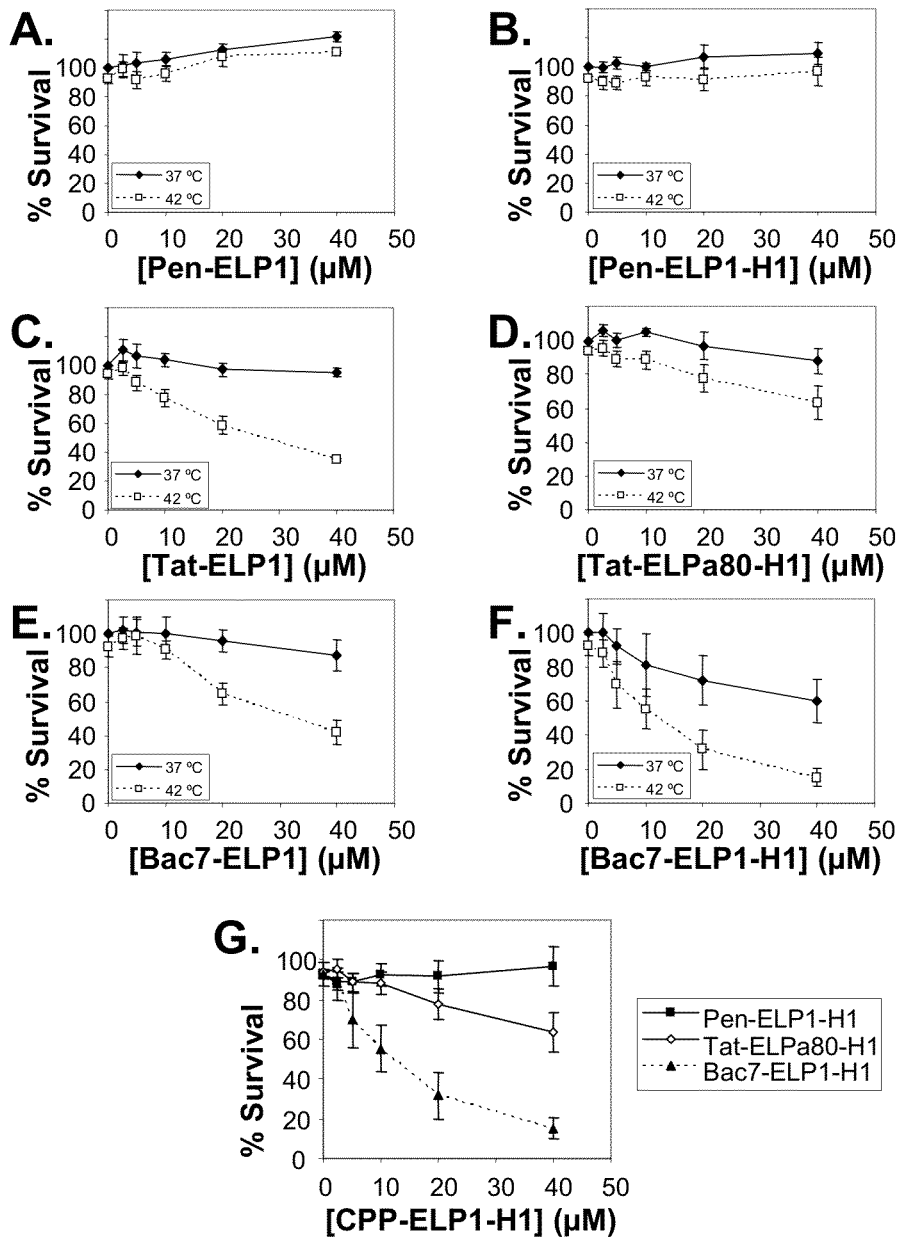
FIG. 15 is multiple charts showing MCF-7 Proliferation after CPP-ELP-H1 treatment. MCF-7 cells were treated for 1 h at 37 or 42° C. with various concentrations of Pen-ELP1-H1 (B.), Tat-ELPa80-H1 (D.), or Bac7-ELP1-H1 (F.), or the respective control polypeptides lacking the H1 sequence (A., C., and E.), and the cell viability was determined after 7 days using the MTS assay. G. Overlay of the 42° C. data for each CPP-ELP-H1.

All CPP-ELP-H1 constructs were tested for their ability to inhibit the proliferation of MCF-7 cells. Cells were treated for 1 h at 37 or 42° C. with various concentrations of Pen-ELP1-H1, Tat-ELPa80-H1 (ELPa80 was used because Tat-ELP1-H1 had a $T_t$ above the desired range), and Bac7-ELP1-H1, and the cell number was determined 7 days later using a the MTS assay. Also, each CPP-ELP1 control, lacking the H1 peptide, was tested in order to determine if any of the CPP-ELP1 constructs was toxic to MCF-7 cells. Pen-ELP1-H1 showed little effect on cell proliferation (FIGS. 15A and B). This is consistent with the results above that Pen-ELP-H1 acts by slowing the rate of proliferation of MCF-7 cells, and 11 days after treatment are needed to observe significant cell killing (93). Tat-ELPa80-H1 did inhibit the proliferation after 7 days, and its effect was enhanced when hyperthermia was applied during treatment (FIG. 15D). However, Tat-ELP, which lacks the H1 peptide, also showed significant toxicity, and all of the inhibition seen can be contributed to this toxicity (FIG. 15C). This has been observed previously (143), and is likely to be due to effects of Tat-ELP on the plasma membrane (data not shown). In vivo testing is necessary to determine if the toxicity seen in cell culture will be present in a whole animal setting. Bac7-ELP1-H1 was the most potent inhibitor of cell proliferation, and its effect was enhanced greatly by hyperthermia treatment (FIG. 15F). The Bac7-ELP1 control did have some toxicity, but not as much as the Bac7-ELP1-H1 construct (FIG. 15E). For comparison, the data from each CPP-ELP1-H1 after 42° C. treatment was overlaid (FIG. 15G). It is clear that Bac7-ELP1-H1 is by far the most potent of the constructs tested. It is interesting that Bac7-ELP1-H1 is much more potent than Pen-ELP1-H1 to spite its lower cellular uptake. This result may be explained by the subcellular localization of the two polypeptides.

Intracellular Localization of the ELP-H1 Polypeptide Fused to Different Cell Penetrating Peptides.

In order to determine the reason for the enhanced antiproliferative effect of Bac7-ELP-H1, the subcellular localization of the polypeptides was assessed. MCF-7 cells were treated with rhodamine labeled polypeptides for 1 h at 37 or 42° C., and the subcellular distribution was determined after 24 h by confocal fluorescence microscopy. As described above Pen-ELP1-H1 displayed a punctate cytoplasmic distribution at 37° C., and large aggregates of Pen-ELP1-H1 could be seen in the cytoplasm following 42° C. treatment (FIG. 16A, top panel). The distribution of Tat-ELPa80-H1 was similar to Pen-ELP1-H1, with cytoplasmic staining and aggregates present after hyperthermia treatment (FIG. 16A, middle panel). Bac7-ELP1-H1, in contrast, showed intense plasma membrane staining at 37° C., with a small amount of polypeptide present in the cytoplasm (FIG. 16A, lower left). After hyperthermia treatment, Bac7-ELP1-H1 displayed a more diffuse distribution with some polypeptide and polypeptide aggregates in the cytoplasm and a lesser amount of polypeptide in the nucleus. Also, in a subset of cells, Bac7-ELP1-H1 showed very bright nuclear staining exclusive of nucleoli (FIG. 16A, lower right, arrow). Cytoplasmic delivery of ELP by Tat and nuclear delivery by Bac7 was further confirmed in SKOV-3 cells (FIG. 16B). Since the c-Myc/Max dimerization occurs in the nucleus, it is feasible that the ability of Bac7 to delivery the c-Myc inhibitory polypeptide into the nucleus lead to its increased antiproliferative effect.

Growth of MCF-7 Xenografts in Nude Mice.

Figure 17:
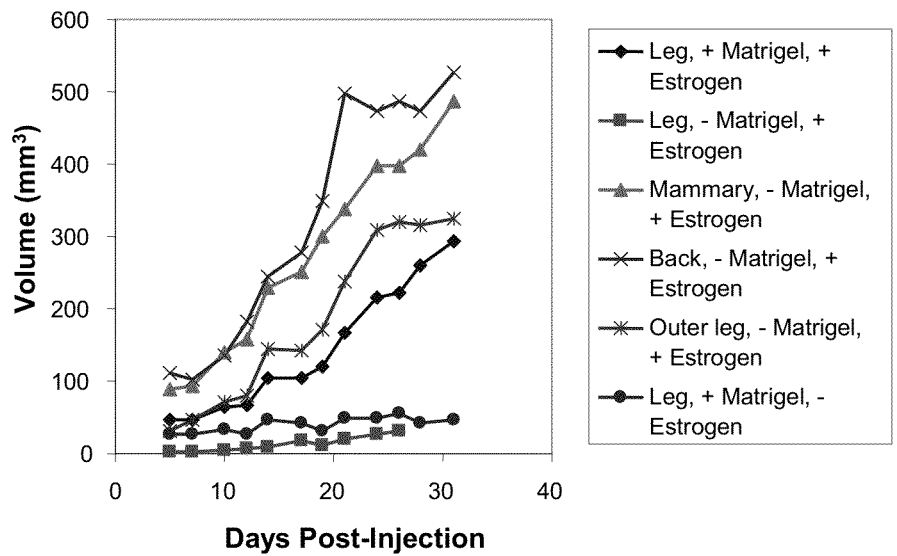
FIG. 17 shows MCF-7 Tumor Growth in Athymic nu–/nu– Mice. 12×106 MCF-7 cells were injected subcutaneously into mice bearing extended release estradiol pellets at various sites, with or without mixture with 0.2 cc of Matrigel. Tumor growth was monitored 3 times per week by caliper measurement. Leg, +Matrigel, +Estrogen, n=28 tumors; Leg, –Matrigel, +Estrogen, n=4 tumors; Mammary, –Matrigel, +Estrogen, n=4 tumors; Back, –Matrigel, +Estrogen, n=2 tumors; Outer leg, –Matrigel, +Estrogen, n=2 tumors; Leg, +Matrigel, –Estrogen, n=4 tumors. Error bars were omitted for clarity.

In order to determine the optimal placement for tumor growth and learn the growth rate of the MCF-7 tumors, nude mice were implanted with MCF-7 cells at various sites under various injection conditions. FIG. 17 shows the growth rate of MCF-7 tumors, and the tumors placed in the back and in the mammary fat pads showed the most aggressive growth. Also, Matrigel was not required for efficient tumor growth at these sites. MCF-7 tumors grown on the inner and outer mouse flanks also proliferated aggressively. However, when grown on the inner thigh, Matrigel was required to achieve good tumor growth. Also, in animals lacking 17-β-estradiol stimulation, the tumors did not grow well at all. It was determined that the MCF-7 tumors began the exponential growth phase approximately 10 days after injection, thus providing a timeline for future experiments to determine the effectiveness of treatment with the H1 polypeptide.

Heating the MCF-7 Tumors Using IR Light

Figure 18:
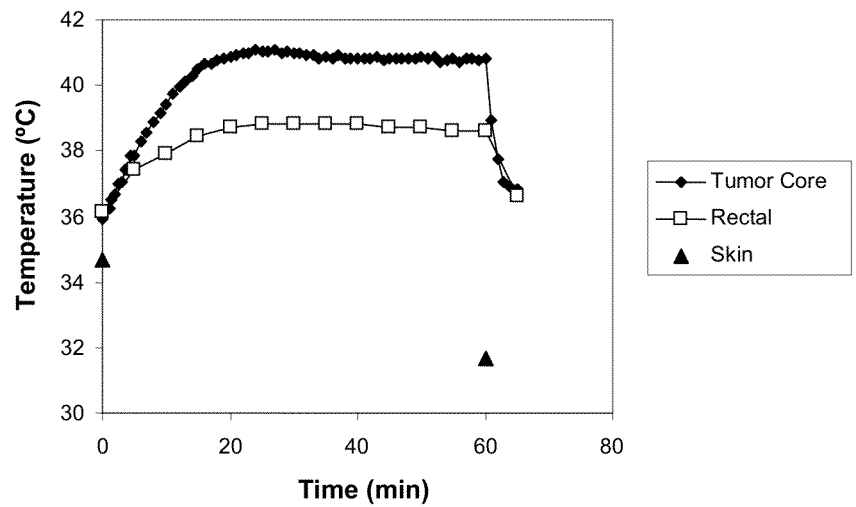
FIG. 18 is a graph that shows MCF-7 Tumor Heating by Infrared LED Light. MCF-7 tumors on the inner thigh of mice, an average of 8 mm×5 mm, were heated for 1 h using LED generated IR light at 805 nm and 10 kHz pulse frequency. Tumor temperature was measured using a needle thermocouple inserted into the tumor core. Body temperature was monitored with a rectal probe, and the slight elevation seen was due to the proximity of the LED to the rectal probe. Skin temperature at the heated site was monitored using an IR beam temperature probe before and after the heating period. Data represent an average of 3 tumors; error bars were omitted for clarity.

In order to test the effectiveness of using IR light generated by the Laser Systim 540 to heat the tumors, three representative tumors on the mouse inner thigh (approximately 8×5 mm) were used in a heating trial. A needle thermocouple was placed in the tumor core, and the LED probe was positioned approximately 1 mm from the skin over the tumor site. The area surrounding the tumor was shielded from illumination using a non-transparent paper covering. The LED unit was activated at full pulse frequency of 10 kHz, and the tumor core temperature was monitored every minute. The tumor core reached the desired hyperthermia temperature within 20 minutes of the start of illumination, and the temperature remained stable at an average of 41° C. for the remainder of an hour (FIG. 18). The mouse body temperature rose slightly during the heating period as determined by a rectal temperature probe. However, this rise is likely an artifact of the placement of the LED probe. When positioned to heat the tumor on the inner thigh, the LED probe is very close to the position of the rectal thermometer, likely leading to a falsely high temperature reading. Interestingly, the skin temperature at the illuminated site did not increase during the heating period. This likely reflects the fact that heating of the tissue results from absorbance of the IR light, so the heat generated by this device is centered deeper in the tissue with little temperature change at the skin surface. When the LED illumination was removed, the tumor tissue rapidly returned to baseline within 5 minutes.

Plasma Clearance of Bac7-ELP-H1

Figure 19:
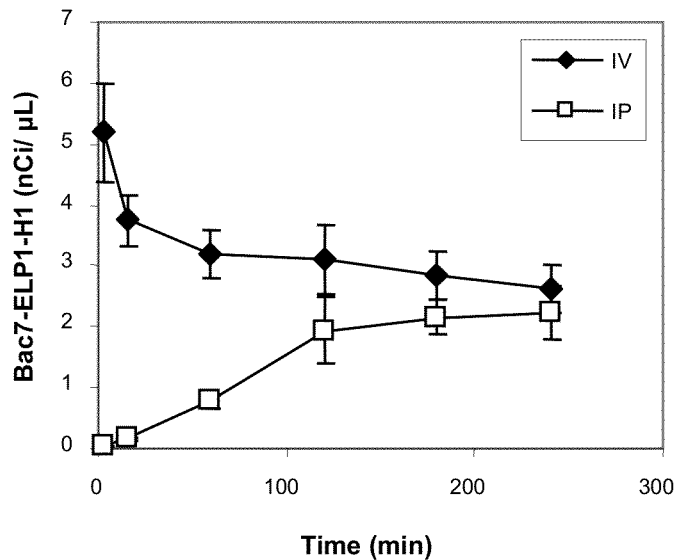
FIG. 19 is a graph that shows plasma Clearance of Bac7-ELP1-H1. 50 µCi of 125I-labeled protein was injected IV via the jugular vein or IP in MCF-7 bearing mice. Blood was collected at the indicated times, centrifuged, and a sample of the plasma was counted using a µ counter. Data represent the average of 3 animals per injection route; error bars, SD.

The clearance rate of Bac7-ELP-H1 was determined by injecting $^{125}$I labeled polypeptide into nude mice bearing MCF-7 tumors. Both the intravenous (i.v.) route and the intraperitoneal (i.p.) route were examined. When injected i.v., the plasma levels initially showed a rapid drop to about 50% of the initial level within 60 min of the injection. However, after the first hour, the plasma level was quite stable (FIG. 19). This long half life is typical of macromolecular carriers (144, 145), and may represent an advantage for delivery of therapeutic peptides, which are normally cleared or degraded quite quickly (146). When injected i.p., the plasma levels were initially very low. However, with time the polypeptide did move from the lymphatic system into the blood circulation, and beginning at 2 h after injection, the i.p. route produced nearly the same plasma level as did the i.v. injection.

Biodistribution of Bac7-ELP-H1 in Nude Mice

Figure 20:
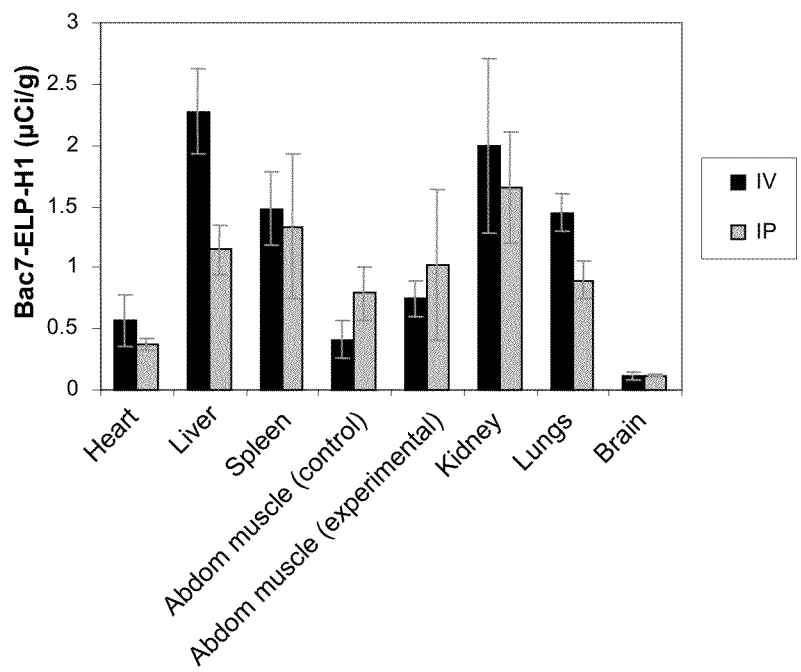
FIG. 20 is a graph that shows biodistribution of Bac7-ELP1-H1 in MCF-7 Tumor Bearing Mice. Mice were injected IV or IP with 50 µCi of 125I-labeled protein. For IV injections, tumors were heated for 60 min after injection using an IR LED. For IP injections, tumors were heated from 60 min to 120 min after injection. 240 min after injection, the mice were sacrificed and samples of the major organs were weighed and counted using a µ counter. Data represent the average of 3 animals for each injection route; error bars, SD.

The biodistribution of $^{125}$I-Bac7-ELP1-H1 was determined in the major organs of MCF-7 bearing mice 4 h after injection by γ counting (FIG. 20). The polypeptide accumulated most highly in the liver. This is commonly seen with large molecular weight molecules (22), and is likely due to the high permeability of capillary beds in the liver to large molecular weight molecules (147). High levels of Bac7-ELP-H1 were also present in the spleen, kidneys, and lungs. A low level of Bac7-ELP-H1 was found in the muscle beneath the tumor site, with a slight increase on the heated side. The polypeptide was found at low levels in the heart, and very little was found in the brain. The polypeptide distribution following the i.p. and i.v. injection routes did not differ widely. The only significant differences were a lower accumulation in the liver and lungs following the i.p. injection. This data suggests that the i.p. route may be a feasible mechanism for delivery of Bac7-ELP-H1, but more data is needed to determine the stability of the polypeptide after each injection protocol.

Example 2

Test Regarding Present Invention and C6 Cell Proliferation

Figure 21:
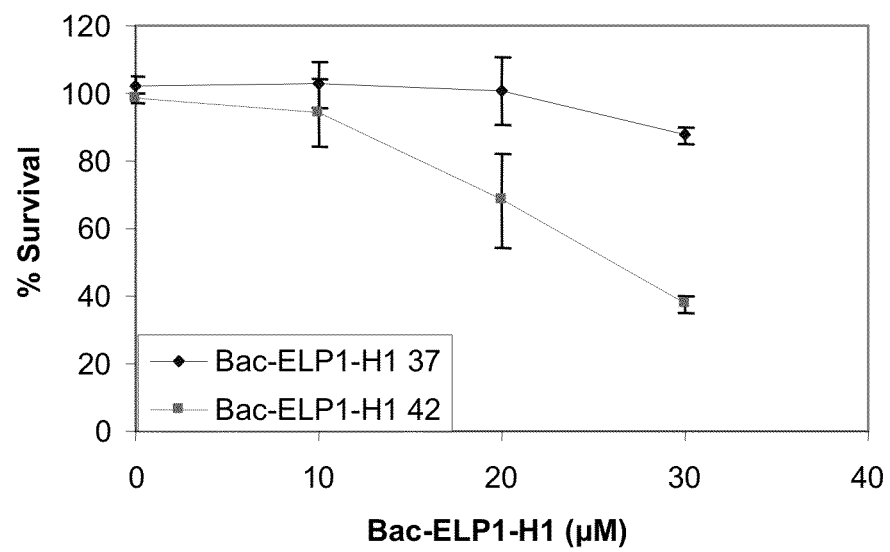
FIG. 21 is a chart showing antiproliferative effect of Bac-ELP1-H1. Proliferation of C-6 cells was determined 3 days after a 1 h polypeptide exposure at 37° C. or 42° C. Cells number was determined using the MTS assay. Results represent the mean±SEM of 3-5 experiments performed in duplicate.

CPP-ELP-H1 is an effective inhibitor of breast cancer cell proliferation in vitro (see above), and its efficacy for breast cancer therapy in vivo is currently being established. However, malignant glioma is a cancer that is much more difficult to treat and with a much lower cure rate than breast cancer. Therefore, developmental therapeutics for malignant glioma is a field that could greatly benefit from the targeted approach applied with ELP technology. In order to examine the antiproliferative effects of the CPP-ELP-H1 polypeptides in glioma cells, C6 cells were exposed for 1 hour to 20 μM Bac-ELP1-H1 or Bac-ELP2-H1 at 37° C. or 42° C. one day after cell seeding. The polypeptides were washed away, and the cells were allowed to grow until day 3. Cell number was determined using the MTS assay. FIG. 21 shows that the thermally sensitive peptide Bac-ELP1-H1 did not inhibit cell proliferation when cells were treated at 37° C. However, when cells were treated at 42° C., cell proliferation was inhibited by up to 60%.

The nonthermally responsive control, Bac-ELP2-H1, had no effect on C6 proliferation, and control polypeptides lacking the c-Myc inhibitory sequence (Bac-ELP1 or Bac-ELP2) did not have any effect on cell proliferation (data not shown). These results suggest that the polypeptides exhibit an antiproliferative effect in C-6 cells, which can be further enhanced by hyperthermia.

Figure 22:
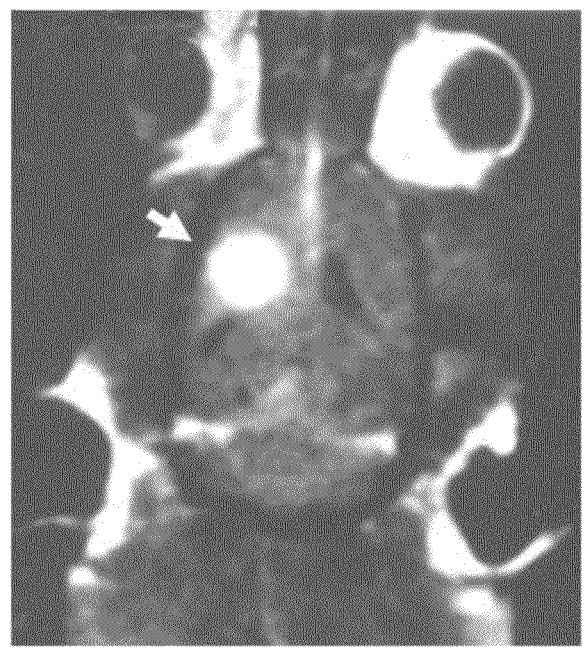
FIG. 22 is a photograph showing a weighted axial MRI image with contrast of a rat brain. The white sphere (arrow) is a C6 tumor mass.

Development of the C6 Glioblastoma Model: This study will utilize an intracerebral tumor-bearing rat model of glioma (C6). The rat glioma model is similar to human malignant glioma (glioblastoma multiforme) both histologically and in rapid proliferation. In a previous study, C6 gliomas were induced by intracranial injection of a suspension of C6 cells. The tumors were imaged sequentially with 3-D volume measurements generated by means of a clinical magnetic resonance imaging system (CMRI) and commercially available wrist coil (FIG. 22). This study demonstrated that gliomas can be reliably grown in rats using the C6 cell line, and MRI imaging is an effective means of monitoring tumor progression.

Figure 23:
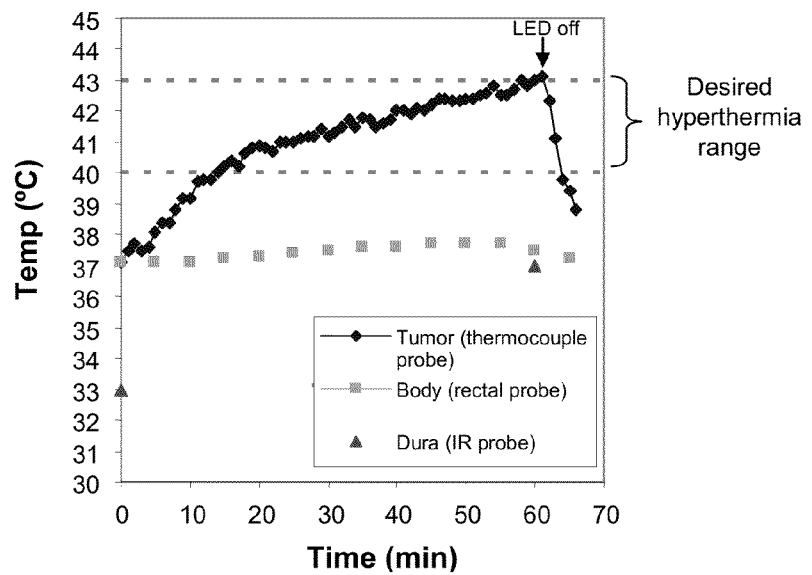
FIG. 23 is a chart showing heating intracranial C6 tumors with infrared light. A craniotomy was performed over the tumor site, and the IR light source was placed 1-2 mm from the dura. Illumination was performed at 10 kHz frequency for 60 min, and the temperature at the tumor core was monitored with a needle thermocouple. Data shown is a representative sample of three experimental animals.

Heating intracerebral C6 tumors using infrared light: Our previous studies in subcutaneous tumor models have used infrared (IR) light generated by the Laser Systim 540® (Mettler Electronics) to heat the tumors. This method is preferred over more primitive techniques such as water bath immersion because the heat can be applied to a more concentrated area and without physical contact with the animal. In order to test the effectiveness of this method in the glioma model, three representative C6 tumors grown in rat brains were used in a heating trial. The tumor core reached the desired hyperthermia temperature within 15 minutes of the start of illumination, and the temperature remained in the desired hyperthermia range for the remainder of an hour (FIG. 23). This experiment demonstrates that the use of IR light is a feasible and minimally invasive method of heating intracerebral C6 tumors.

Figure 24:
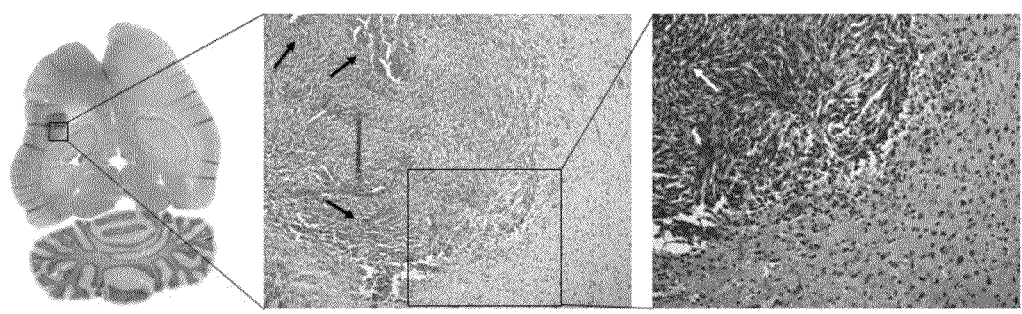
FIG. 24 are photographs showing intracerebral C6 tumors after heating. After 60 min of tumor heating with IR light, A whole brain image was obtained by transillumination and digital photography. 10× and 20× magnified images were collected using a Nikon microscope equipped with a digital camera.

Following the heating period, the rats were exsanguinated and perfused with 4% paraformaldehyde, and the brains were removed, sectioned, and stained with hematoxylin and eosin (H&E). All three animals developed tumors, and the tumors were highly vascularized (FIG. 24, middle panel, black arrows). Additionally, the tumor tissue displayed rosettes that are characteristic of glioblastoma (right panel, white arrow). The area around the tumor appeared as normal neural tissue, and no acute damage from the hyperthermia treatment was apparent.

Figure 25:
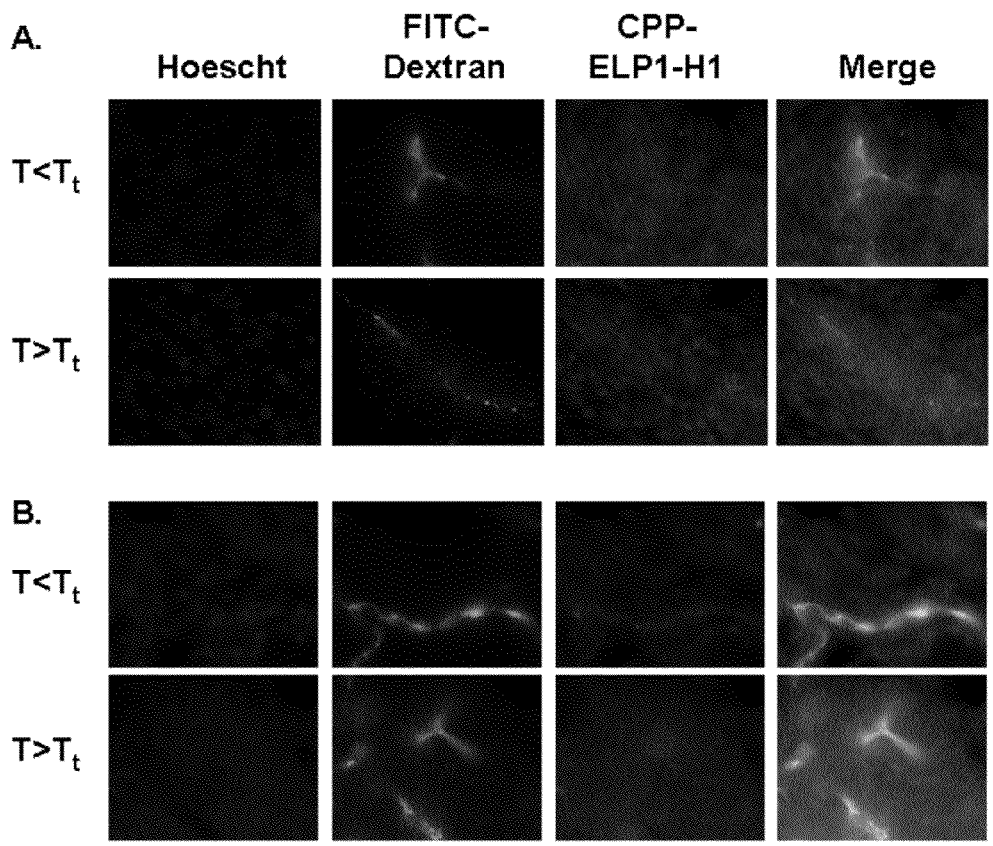
FIG. 25 are photographs showing intratumoral localization of the ELP drug carrier. Rhodamine-labeled Bac-ELP1-H1 (A.) or Tat-ELP1-H1 (B.) was injected IV, and one of two subcutaneous C6 tumors was heated with IR light for 60 min. 500 kDa FITC-dextran was injected 1 min prior to euthanasia in order to mark the perfused vessels, and tumors were frozen, sectioned, and stained with Hoescht 33342 to mark the cell nuclei. A representative section from multiple tumor sections from duplicate animals is shown.

Imaging Intratumor Distribution of the Therapeutic Peptide Carrier: Previous studies have shown that ELP accumulation in tumor vasculature or interstitium can be increased with focused hyperthermia. However, entry of the ELP carrier into the tumor cells, a property necessary for effective drug delivery, has never been demonstrated. The use of CPPs fused to the ELP carrier may enhance its uptake into the tumor cells. To test the ability of the Bac and Tat CPPs to enhance ELP uptake into tumor cells in vivo, rats bearing C6 tumors were intravenously injected with Rhodamine-labeled Bac-ELP1-H1 or Tat-ELP1-H1. One tumor was heated for 60 min. using IR illumination as described above. 1 min prior to euthanasia, high molecular weight (500 kDa) FITC-dextran was injected IV in order to mark the perfused vessels. The tumors were removed, rapidly frozen, and sectioned using a cryomicrotome. Tumor sections were fixed and stained with Hoescht 33342 and imaged using a Nikon fluorescence microscope with a CoolSnap CCD camera. As shown in FIG. 25A, Bac-ELP1-H1 is present not only in the tumor blood vessels, but it also escaped circulation and entered the tumor cells. Below the $T_t$ (top panel), Bac-ELP1-H1 is present in the cytoplasm of the tumor cells. Above the $T_t$, the polypeptide can also be detected in the tumor cell nuclei. This is consistent with the localization of the polypeptide in cultured cells (data not shown). Tat-ELP1-H1 is also able to escape the tumor vasculature and enter the tumor cells (FIG. 25B). Tat-ELP1-H1 was present in the cell cytoplasm at temperature above and below the $T_t$, again consistent with its subcellular localization in vitro. Thus, this Example indicates a direct observation that ELP aided by a CPP can escape the tumor vasculature and enter the tumor cells.

Figure 26:
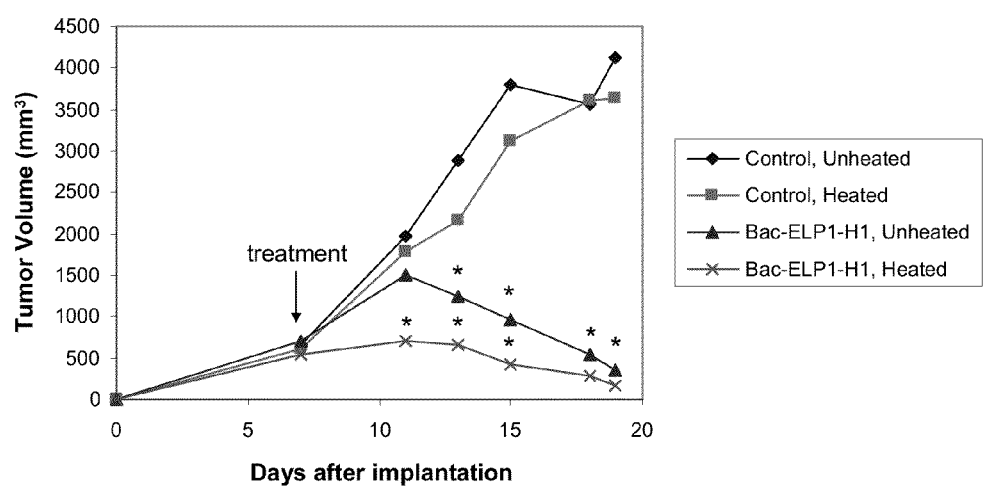
FIG. 26 is a chart showing C6 tumor reduction by Bac-ELP-H1. Rats bearing 2 subcutaneous C6 tumors were treated by IV injection of saline or Bac-ELP1-H1 (130 mg/kg), and one tumor was heated for 60 min by IR illumination. Tumor size was monitored until Day 19 by caliper measurement. The average tumor volume of 5 animals in each group is shown. Error bars were removed for clarity; *, statistically different from Control, Unheated as assessed by an ANOVA, p<0.05.

Tumor Size Reduction by the ELP-delivered c-Myc Inhibitory Peptide: In order to assess the ability of the ELP-delivered c-Myc inhibitory peptide to reduce tumor size, rats bearing 2 C6 tumors implanted subcutaneously in the rats' back were treated by IV injection of Bac-ELP1-H1 (130 mg/kg) or saline control, and one tumor was heated for 60 min using the IR heating method. Bac-ELP1-H1 was used in this study because it was found to be the most potent inhibitor of cell proliferation in vitro (unpublished data). Following treatment, the animals were returned to their cages, and tumor size and body weight was monitored for 19 days. In saline treated rats, the tumors proliferated rapidly up to a volume of 4000 mm$^3$, and hyperthermia alone had no effect on tumor size (FIG. 26). In contrast, the tumors in animals treated with Bac-ELP1-H1 began to shrink 4 days after treatment, and were nearly undetectable at day 19. Both the heated and unheated tumors in the treated animals were eventually cleared after treatment, but the heated tumor was reduced slightly faster. This indicates that at a dose of 130 mg/kg, Bac-ELP-H1 is potent enough to completely eliminate C6 tumor growth. Further studies are underway at lower doses in order to look for a more significant difference between the heated and unheated tumors. No body weight loss, injection site reactions, or gross signs of toxicity were observed.

Figure 27:
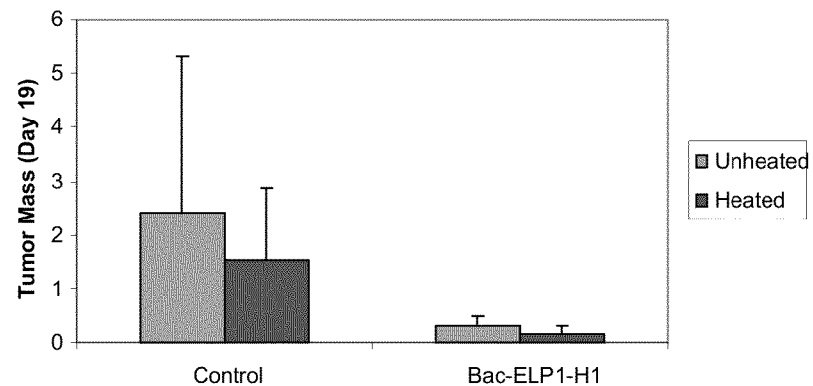
FIG. 27 is a chart showing tumor weights after treatment with 130 mg/kg Bac-ELP1-H1. A necropsy was performed on Day 19 after tumor implantation, and tumors were dissected and weighed.

Rats were sacrificed on Day 19 after implantation, and tumors were removed and weighed. As shown in FIG. 27, Untreated animals had tumors weighing approximately 2 g, and there was no significant difference between heated and unheated tumors. Animals treated with Bac-ELP1-H1, however, had significantly smaller tumors, with an average weight of less than 300 mg. No significant difference was seen between heated and unheated Bac-ELP1-H1 treated tumors, again supporting the evidence that 130 mg/kg is a sufficient dose to cause complete tumor regression even without hyperthermia.

Figure 28:
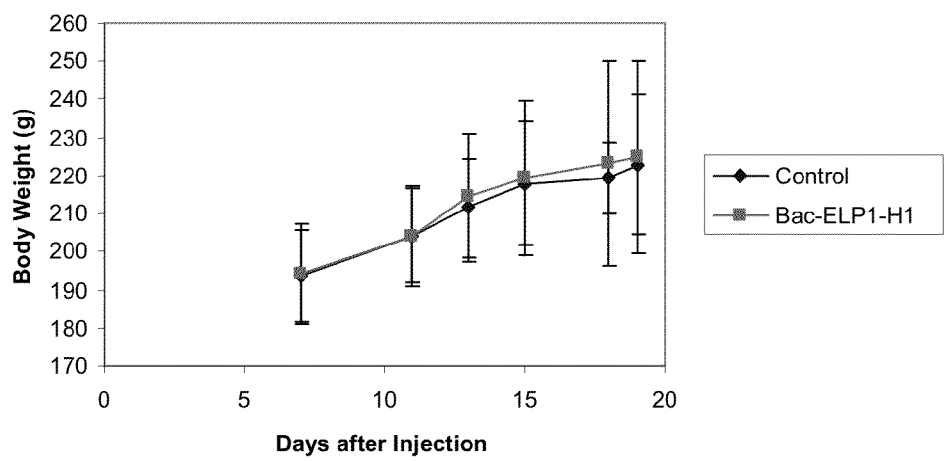
FIG. 28 is a chart showing body weight of rats after saline or Bac-ELP1-H1 treatment. Rats were treated with saline control or Bac-ELP1-H1 (130 mg/kg) by IV injection on Day 7 after tumor implantation, and body weights were recorded regularly throughout the experiment.
Figure 29:
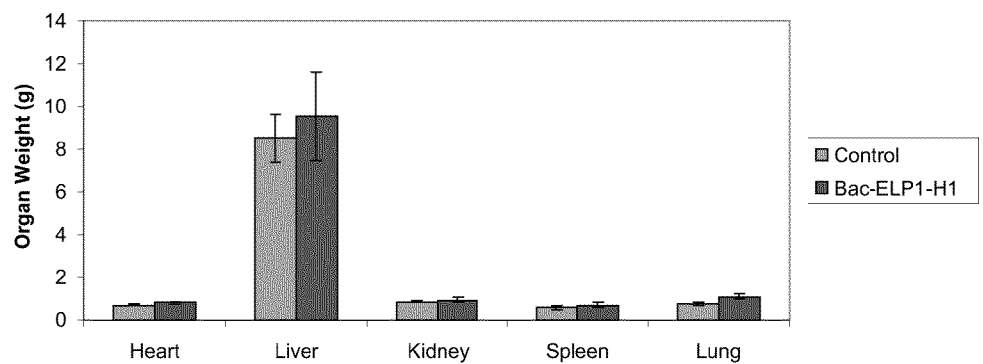
FIG. 29 is a chart showing organ weights of rats after saline or Bac-ELP1-H1 treatment. Rats were treated with saline control or Bac-ELP1-H1 (130 mg/kg) by IV injection on Day 7 after tumor implantation, and organ weights were recorded at necropsy on Day 19.

Evaluation of Toxicity of the Bac-ELP1-H1 Polypeptide: In addition to monitoring tumor size during the above experiment, rats were monitored for weight loss or other signs of acute toxicity due to the Bac-ELP1-H1 treatment. The average body weight of the animals did not differ between saline and Bac-ELP1-H1 treated groups, and no weight loss was observed following Bac-ELP1-H1 treatment (FIG. 28). In addition, all major organs were removed and weighed at necropsy on Day 19. No significant difference was seen in organ weights from animals treated with saline control and animals treated with Bac-ELP1-H1 (FIG. 29). Also, no hair loss or injection site reactions were observed (data not shown), and no other signs of toxicity were noticed.

Example 3

Combination Therapy of Pen-ELP-H1 with Topoisomerase II Inhibitors

Enhancement of the Toxicity of Topoisomerase II Inhibitors by Pretreatment with Pen-ELP-H1

Figure 30:
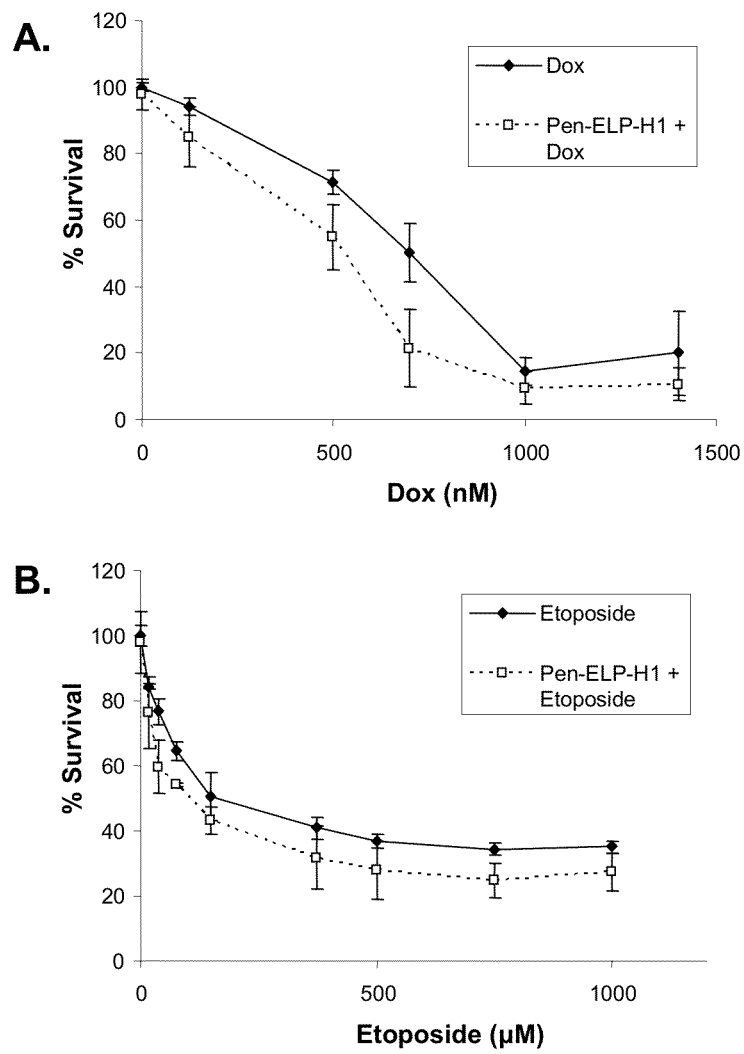
FIG. 30 is a set of graphs that show reduction in Drug $IC_{50}$ by Pen-ELP-H1 Pretreatment. The effect of drug concentration on cell viability for Dox (A) or etoposide (B) was determined with and without Pen-ELP-H1 pretreatment. Cells were pretreated on day 1 with 20 µM Pen-ELP-H1 and treated on day 4 with drug. Viability was determined on day 7 using the MTS cell viability assay. A single representative experiment is shown (error bars=SD).

The ability of Pen-ELP-H1 to enhance the effectiveness of chemotherapeutic agents was tested in MCF-7 breast cancer cells. Cells were treated on day 1 with 20 μM Pen-ELP-H1 or a control polypeptide which lacks the c-Myc inhibitory sequence (Pen-ELP) for 1 h, rinsed, and placed in fresh media for 3 days. On day 4, the cells were exposed to the drugs at various concentrations for 72 h, and viability was assessed using the MTS cell viability assay. As shown in FIG. 30A, the cytotoxicity of Dox, a topoisomerase II inhibitor, is enhanced after pretreatment of the cells with the c-Myc inhibitory polypeptide (P<0.01). Similar effects were seen with a different topoisomerase II inhibitor, etoposide (P<0.01) (FIG. 30B). Data from the MTS assay was averaged and fit using an exponential equation in order to calculate the $IC_{50}$ with and without pretreatment. Results of the $IC_{50}$ calculations are shown in Table 3. The reduction in $IC_{50}$ with Pen-ELP-H1 pretreatment is about 1.5 fold for both Dox and etoposide. The control polypeptide Pen-ELP had no significant effect on the Dox or etoposide $IC_{50}$. Also, no enhancement of the Dox and etoposide $IC_{50}$ was observed if the treatment schedule was reversed, treating with Dox or etoposide first for 72 h, then adding Pen-ELP-H1 (data not shown). In order to examine whether the effect of c-Myc inhibition was specific to topoisomerase II inhibitors, the effect was also tested with camptothecin, a drug that inhibits topoisomerase I. Pretreatment with Pen-ELP-H1 or Pen-ELP had no significant effect on cell killing by camptothecin. Similarly, no effect was seen on the cytotoxicity of an unrelated DNA alkylating agent, cisplatin (Table 3).

TABLE 3

Effects of Pen-ELP-H1 pretreatment on drug $IC_{50}$ values in MCF-7 cells

| Drug | $IC_{50}$ (mean ± SEM) | $IC_{50}$ after Pen-ELP pretreatment (mean ± SEM) | $IC_{50}$ after Pen-ELP-H1 pretreatment (mean ± SEM) |
|---|---|---|---|
| Doxorubicin ‡ | 751.7 ± 21.6 nM | 777 ± 75.1 nM | 504.2 ± 35.3 nM |
| Etoposide ‡ | 210.4 ± 12.4 μM | 186.8 ± 13.8 μM | 141.4 ± 3.5 μM |
| Camptothecin | 235.1 ± 9.8 nM | 229 ± 46.4 nM | 235.4 ± 5.8 nM |
| Cisplatin | 10.2 ± 0.511 μM | 11.6 ± 1.611 μM | 9.4 ± 1.4 μM |

‡ difference between control and Pen-ELP-H1 pretreated $IC_{50}$ is statistically significant as determined by an unpaired Student's t-test (P < 0.01)

Table 3. $IC_{50}$ values were calculated from the experiment shown in FIG. 19. Curves were fit using an exponential equation, and the $IC_{50}$ value shown represents the mean±SEM of at least 5 independent determinations, each performed with 4 replicates per drug concentration. Statistical significance was assessed using an unpaired Student's t-test.

Effects of Pen-ELP-H1 on Cell Cycle Distribution.

Figure 31:
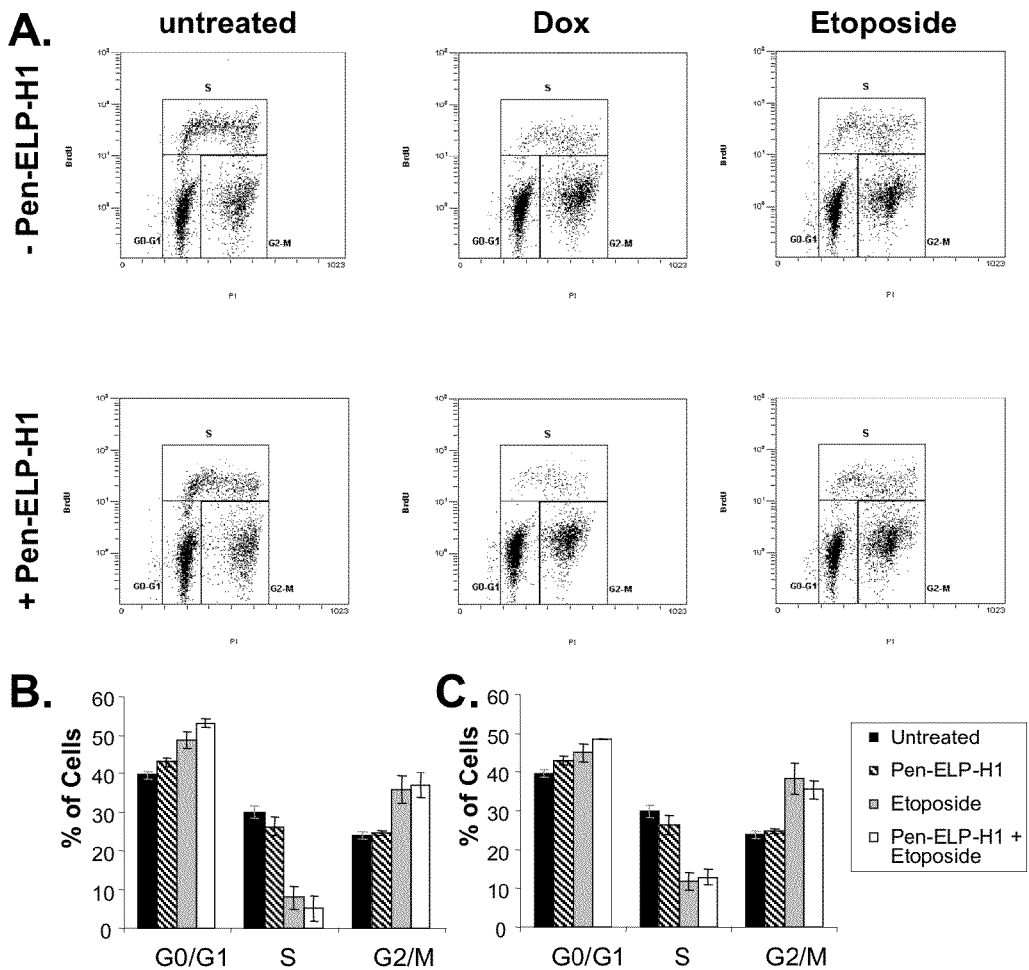
FIG. 31 is a set of graphs that show cell cycle analysis of MCF-7 Cells after Pen-ELP-H1 Pretreatment before Dox or Etoposide. A. Cells were pretreated with 20 µM Pen-ELP-H1 on day 1 and 100 nM Dox or 1 µM etoposide on day 4 and analyzed on day 5 by flow cytometry with BrdU and propidium iodide staining Raw data for a single representative experiment is shown. 4 independent experiments with Dox (B) and etoposide (C) were averaged. Percentages were determined by analysis of 5000 cells/sample, and results shown represent the mean±SEM.

To gain more insight into the effect of polypeptide and drug treatment, the cell cycle distribution of MCF-7 cells was examined. Cells were treated as above with 20 μM Pen-ELP-H1 on day 1 and Dox (100 nM) or etoposide (1 μM) on day 4. On day 5, the cells were pulsed with BrdU and stained with propidium iodide for flow cytometric analysis of the cell cycle distribution. BrdU was used to accurately estimate the fraction of cells in S-phase, and this was combined with propidium iodide staining to denote each phase of the cell cycle (FIG. 31A). Treatment with the c-Myc inhibitor alone lead to an accumulation of cells in $G_1$ and a reduction of cell number in S phase (FIG. 31B). Dox caused arrest in $G_1$ and $G_2$/M at the expense of S phase. The pattern observed with Dox was enhanced upon pretreatment with Pen-ELP-H1, where the $G_1$ fraction increased from about 48% to 53%, and the S phase fraction was reduced from 8% to 5% as compared to treatment with Dox alone (FIG. 31B). Treatment of MCF-7 cells with etoposide caused accumulation in both $G_1$ and $G_2$/M (FIG. 31C). Adding Pen-ELP-H1 before etoposide treatment slightly enhanced the etoposide-induced accumulation in $G_1$, but had no significant effect on the $G_2$/M accumulation (FIG. 31C).

Doxorubicin Uptake and Efflux.

Figure 32:
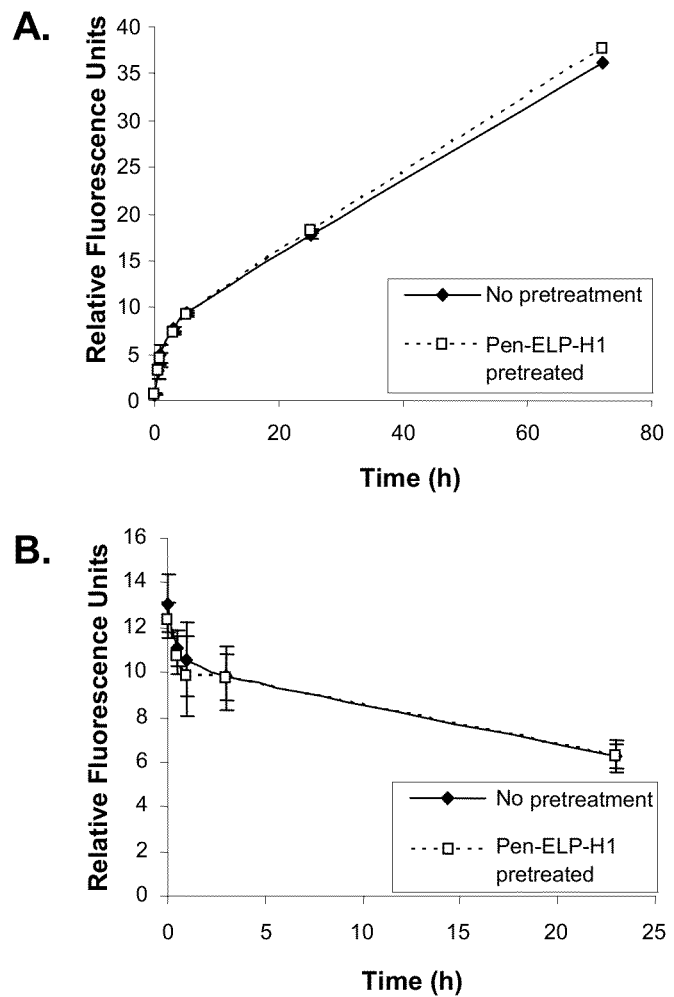
FIG. 32 is a set of graphs that show Dox accumulation and efflux. A. Dox accumulation. Cells were exposed to Dox (1 µM) for various lengths of time with or without Pen-ELP-H1 pretreatment. B. Dox efflux. Cells (Pen-ELP-H1 pretreated and control) were exposed to 1 µM Dox for 5 h, then rinsed and placed in fresh media and analyzed at the indicated time points. Dox levels were determined using the intrinsic Dox fluorescence measured by flow cytometry. Data represent the mean±SEM of 3 independent experiments (n=5000 cells).

In order to determine whether the enhanced toxicity of Dox was due to an increase in the cellular accumulation of drug after Pen-ELP-H1 treatment, intracellular Dox levels were assessed by flow cytometry using the intrinsic Dox fluorescence. Dox uptake by MCF-7 cells was measured by exposing cells to Dox (1 µM) for different lengths of time with or without pretreatment with Pen-ELP-H1. The amount of Dox in the cells increased with increasing exposure time, but pretreatment with Pen-ELP-H1 had no effect on the Dox levels (FIG. 32A).

Although Dox accumulation in cells was unaffected by polypeptide pretreatment, it is still possible that the enhanced cytotoxicity may be the result of Pen-ELP-H1 inhibition of Dox efflux from the cells. In order to test this, cells were loaded with Dox (1 µM) for 5 hours, the Dox containing media was replaced with fresh media, and cells were harvested at varying time points after Dox removal for flow cytometry analysis. FIG. 32B shows that some Dox did diffuse from MCF-7 cells after the drug was removed. However, pretreatment of cells with Pen-ELP-H1 had no effect on the rate at which the Dox efflux occurred. Since Pen-ELP-H1 did not modulate the Dox $IC_{50}$ by affecting the flux of drug into or out of the cells, the mechanism is likely due to the effect of the c-Myc inhibitory polypeptide on the steady state mRNA levels of c-Myc target genes.

Mechanism for Enhanced Drug Toxicity.

Figures 1, 33:
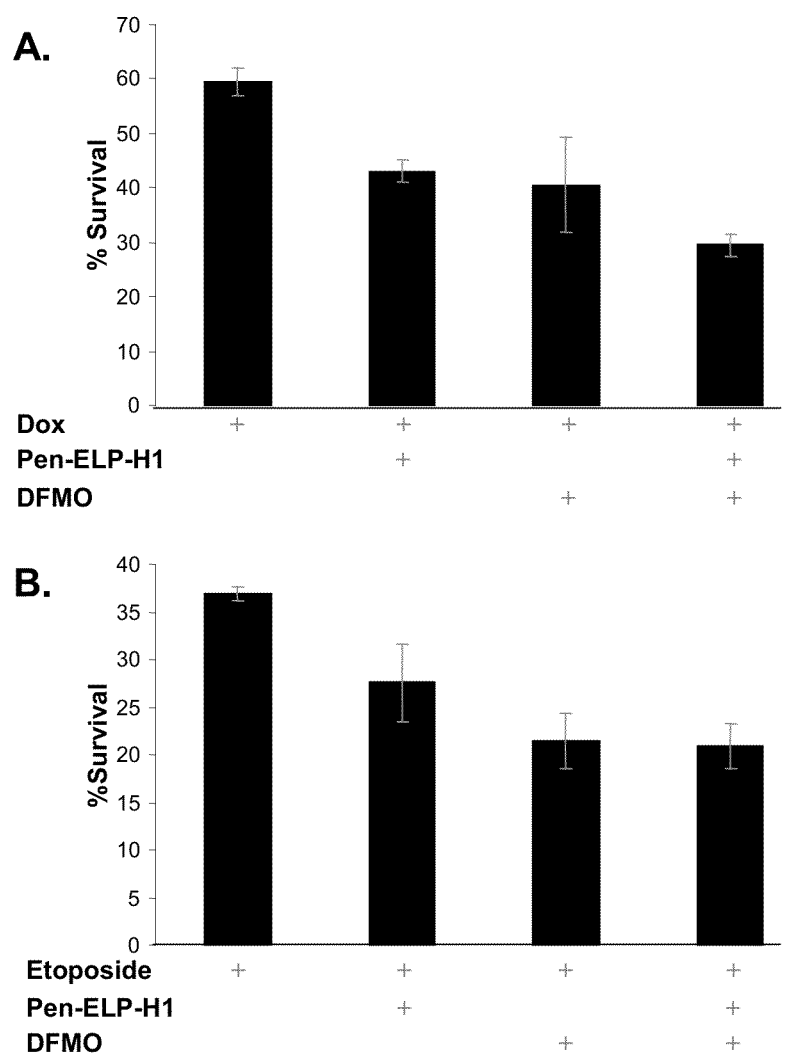
Figures 2, 33:
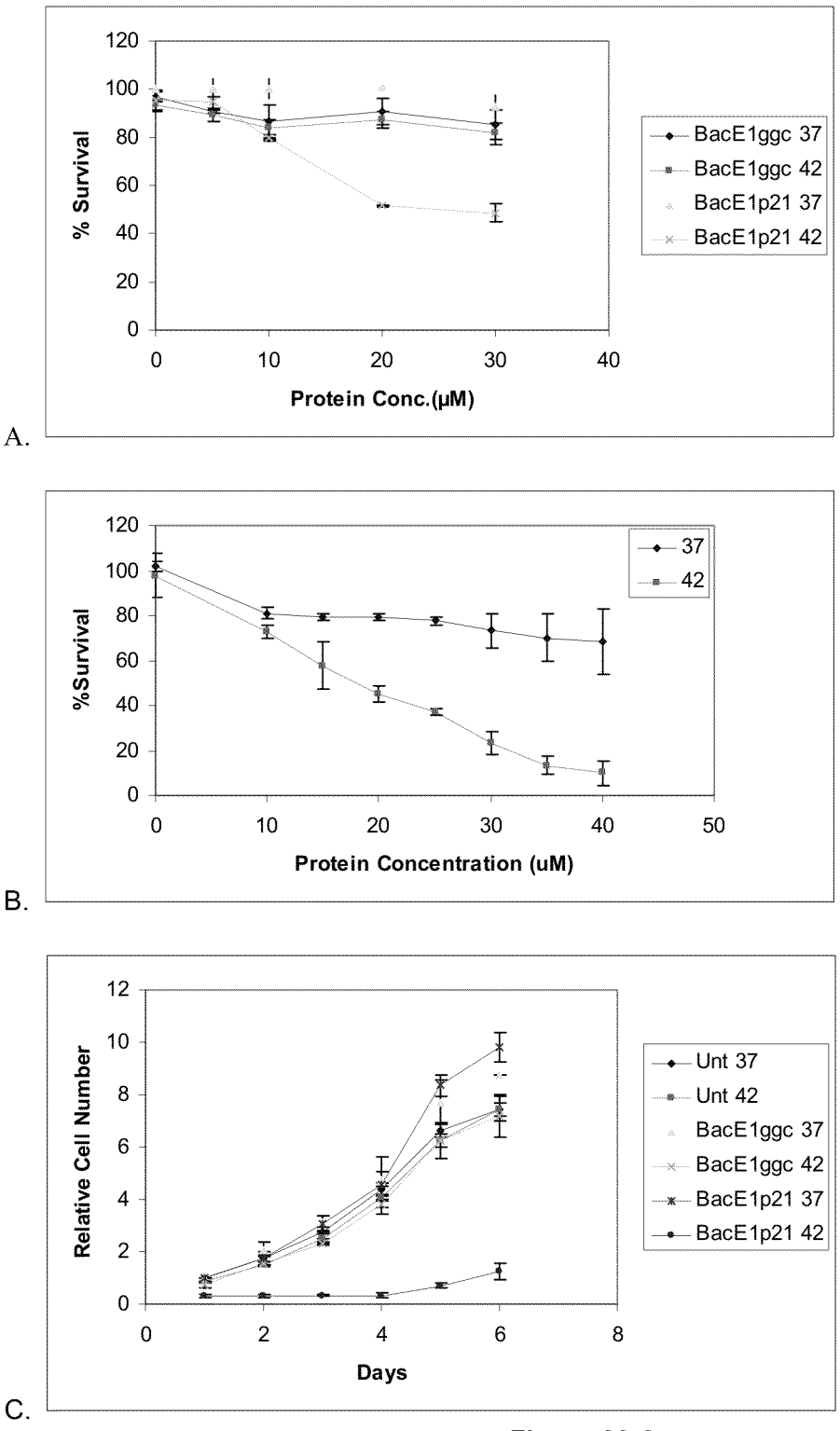

As a transcription factor, c-Myc influences the transcription levels of a large variety of genes. One of the genes under c-Myc control encodes the enzyme ODC (140). ODC catalyzes the first and rate-limiting step in the synthesis of cellular polyamines (148). Many previous studies have indicated that polyamine levels may influence cell proliferation, carcinogenesis, and apoptosis, (reviewed in (149)). In addition, a potent irreversible inhibitor of ODC, α-difluoromethylornithine (DFMO), has been shown to enhance the toxicity of many chemotherapeutic drugs, including Dox and cisplatin (150, 151). Above, it was shown that interruption of the c-Myc/Max heterodimer by the Pen-ELP-H1 polypeptide caused a reduction in the steady-state levels of ODC mRNA to less than 40% of control levels (93). This observation led to the hypothesis that modulation of Dox and etoposide toxicity may be due to a reduction in the amount of ODC in the cell. In order to test this hypothesis, a combination of pretreatment with the ODC inhibitor DFMO and/or Pen-ELP-H1 was used in the Dox and etoposide toxicity assay. MCF-7 cells were pretreated with Pen-ELP-H1 (20 µM), DFMO (50 µM), or both before a 72 h exposure to Dox (750 nM) or etoposide (200 µM). Both DFMO and Pen-ELP-H1 enhanced the Dox-induced cell killing by similar amounts (FIG. 31A). Pretreatment with the combination of Pen-ELP-H1 and DFMO showed no greater enhancement of Dox toxicity than either agent used alone (FIG. 33-1 A). Similar results were obtained with Pen-ELP-H1 and/or DFMO combined with etoposide (FIG. 33-1 B). The fact that Pen-ELP-H1 and DFMO do not act additively or synergistically implies that both agents are affecting the same pathway, and either agent alone is sufficient to completely inhibit this pathway.

Cell Line Dependence of Enhanced Toxicity.

In order to establish whether the effect of Pen-ELP-H1 pretreatment is specific to MCF-7 cells, the Dox and etoposide $IC_{50}$ assay was repeated on two other cell lines, HeLa cervical carcinoma cells and MES-SA uterine sarcoma cells. As shown in Table 4, Pen-ELP-H1 pretreatment reduced the Dox $IC_{50}$ by 1.5 fold in HeLa cells. Also, the etoposide $IC_{50}$ was reduced 1.4 fold. Similar results were seen in MES-SA cells, where the Dox $IC_{50}$ was reduced 2 fold, and the etoposide $IC_{50}$ was reduced 1.8 fold. This data demonstrates that the ability of Pen-ELP-H1 to modulate the toxicity of topoisomerase II inhibitors is not specific to MCF-7 cells, but seems to be a general property of inhibition of c-Myc transcriptional activation.

TABLE 4

Effects of Pen-ELP-H1 pretreatment on Drug $IC_{50}$ values in HeLa and MES-SA Cells

| Cell Line | Drug | $IC_{50}$ (mean ± SEM) | $IC_{50}$ after Pen-ELP-H1 pretreatment (mean ± SEM) |
|---|---|---|---|
| HeLa | Doxorubicin ‡ | 13.9 ± 1.3 nM | 9.4 ± 1.2 nM |
| | Etoposide ‡ | 630.5 ± 59.2 nM | 464.6 ± 45.4 nM |
| MES-SA | Doxorubicin ‡ | 33.7 ± 7.1 nM | 16.3 ± 1.6 nM |
| | Etoposide ‡ | 17.3 ± 3.1 uM | 9.8 ± 3.1 uM |

‡ difference between control and Pen-ELP-H1 pretreated $IC_{50}$ is statistically significant as determined by an unpaired Students t-test (P < 0.05)

Table 4. $IC_{50}$ values were collected for HeLa and MES-SA cells. The Dox and etoposide $IC_{50}$ was determined with and without Pen-ELP-H1 pretreatment. Curves were fit using an exponential equation, and the $IC_{50}$ value shown represents the mean±SEM of at least 5 independent determinations each performed with 4 replicates per drug concentration. Statistical significance was assessed using an unpaired Student's t-test.

The following Examples are related to the Cyclin Dependent Kinase Inhibitory Polypeptides Example 4

Ovarian Cancer

Ovarian cancer is the leading cause of fatality among gynecological malignancies. The standard first-line therapy for ovarian cancer includes tumor debulking followed by chemotherapy treatment with paclitaxel, platinum-based agents, or combinations of both (152). Unfortunately, even in patients in whom there is an initial positive clinical response, the development of recurrent drug-resistant ovarian cancer is a common outcome, leading to poor 5-year survival rates of below 30% (153). Therefore it is necessary to develop alternative approaches with therapeutics that have different targets and are not subject to development of drug resistance, such as macromolecular drug delivery carriers. We have tested designed cyclin dependent kinase inhibitory polypeptides in human ovarian carcinoma SKOV-3 cells. These polypeptides consist of: a cell penetrating peptide, ELP, and the p21(Waf1/Cip1) carboxyl-terminal peptide (p21), which exhibits cyclin-dependent kinase-inhibitory activity. The fusion polypeptide Bac7-ELP1-p21 was expressed in *E. coli*, and purified by thermal cycling. SKOV-3 cells were treated with the indicated polypeptides for fixed time periods at different temperatures.

Delivery of a p21 Mimetic Peptide by ELP.

Effect of polypeptides on cell proliferation: In order to determine whether the ELP-delivered p21 peptide could inhbitid cell proliferation, SKOV-3 cells were treated with the indicated polypeptides for 1 h at 37 or 42° C. Cell viability was determined by MTS assay 3 and 6 days later. As seen in FIG. 33-2A, Bac7-ELP1-p21 treatment at 42° C. caused nearly 50% inhibition 3 days after a single 1 h treatment at 20 and 30 µM polypeptide concentration. 6 days after treatment, the 30 µM dose inhibited cell proliferation by about 80% (FIG. 33-2B). No effect was observed at 37° C. Also, no effect was observed with the control Bac7-ELP1-ggc polypeptides at 37 or 42° C. These experiments show that the decrease in cell proliferation presented here is due to the inhibitory peptide p21. The difference in effect seen at 37 and 42° C. is due to the fact that more polypeptide is presented to the cell surface upon application of hyperthermia due to the aggregation of ELP1, which in turn leads to the entry of more polypeptide inside the cells. Finally, cell proliferation was monitored with time after a single 1 h exposure to Bac7-ELP1-p21 (FIG. 33-2C). Untreated cells and cells treated with the control polypeptide Bac7-ELP-ggc grew exponentially, doubling about 3.5 times in 6 days. When applied at 37° C., Bac7-ELP1-p21 had no effect on the proliferation rate. However, when treated at 42° C., Bac7-ELP1-p21 almost completely abolished SKOV-3 cell proliferation.

Figure 34:
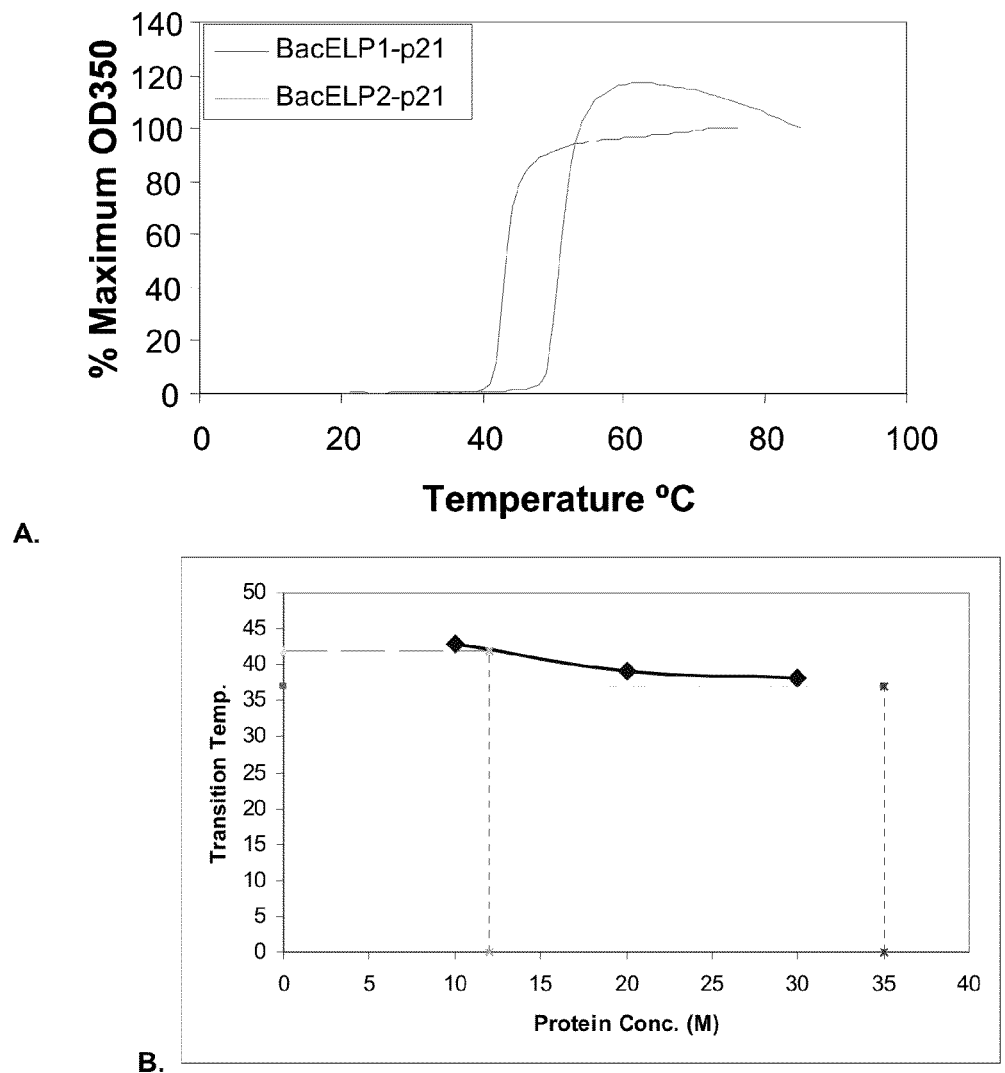
FIG. 34 is a set of graphs that show protein condition and growth curve. A. Phase transition curve of 30 µM Bac7-ELP1-p21 in 10% serum. B. Plot of Bac7-ELP1-p21 concentration with respect to $T_t$. Between the concentrations of 12 and 35 µM, Bac7-ELP1-p21 undergoes its phase transition in the desired temperature range of 37 to 42° C.

Thermal properties of Bac7-ELP1-p21: The turbidity profile of Bac7-ELP1-p21 was determined by heating the polypeptide at rate of 1° C./min and measuring the absorbance at 350 nm. The $T_t$ was defined as the point where 50% turbidity was observed. Bac7-ELP1-p21 demonstrated a $T_t$ of 42° C., ideal for thermal targeting (FIG. 34A). The control polypeptide Bac7-ELP2-p21 aggregated at a temperature higher than the hyperthermia temperature ($T_t$=56° C.), making it a useful control for parsing the effects of ELP aggregation from the effects of hyperthermia. The $T_t$ of Bac7-ELP 1-p21 was determined over a range of concentrations, and a concentration range in which Bac7-ELP1-p21 aggregated at temperatures between 37-42° C. was defined (FIG. 34B). From this analysis, it was determined that between the concentrations of 12 04 and 35 04 in cell culture media, Bac7-ELP1-p21 displayed a suitable $T_t$ for thermal targeting, making this the concentration window in which to perform all subsequent in vitro experiments.

Figure 35:
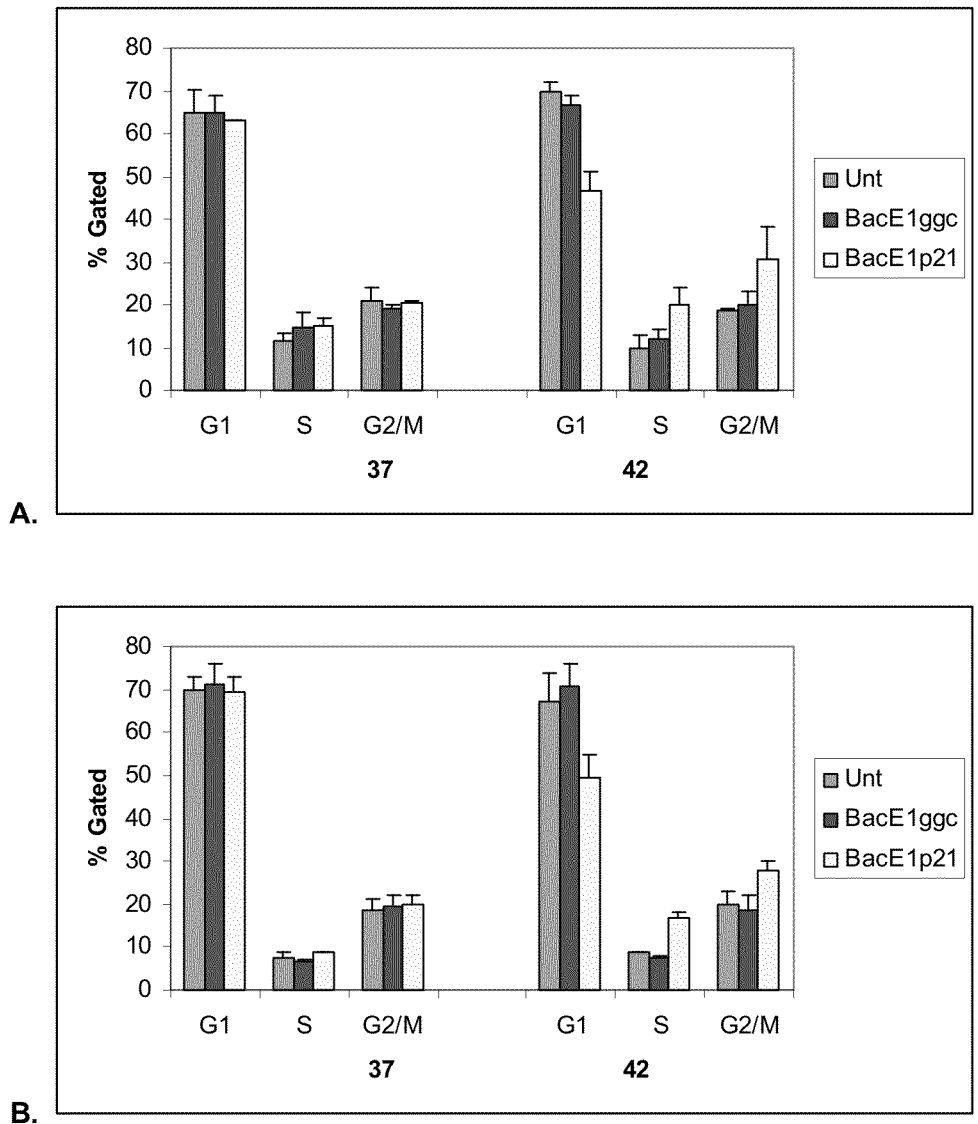
FIG. 35 shows cell cycle analysis in SKOV-3 cells after treatment with Bac7-ELP-p21 polypeptides for 1 h at 37 or 42° C. Cells were harvested 24 (A.) and 48 h (B.) after treatment and analyzed by flow cytometry.

Effect of polypeptide treatment on cell cycle: p21 is a known inhibitor of cyclin/CDK interaction, and active p21 can arrest cell proliferation. In order to determine if the p21 mimetic peptide delivered by ELP affects the cell cycle, SKOV-3 cells were treated with Bac7-ELP1-p21 for 1 h at 37 or 42° C., and the cell cycle distribution was determined 24 and 48 h after treatment by propidium iodide staining and flow cytometry (FIGS. 35 A and B). The control polypeptide Bac7-ELP1-ggc had no effect on cell cycle distribution. Similarly, Bac7-ELP1-p21 treatment at 37° C. did not cause any change in the cell cycle distribution as compared to untreated and Bac7-ELP1-ggc treated samples.

However, when Bac7-ELP1-p21 treatment was combined with hyperthermia, cells accumulated in G2/M and S phase at the expense of G1 phase. Cells analyzed 48 h after treatment were not significantly different from the cells analyzed at 24 h, indicating that the cell cycle effects induced by p21 peptide treatment occur quickly upon exposure to the polypeptide.

Figure 36:
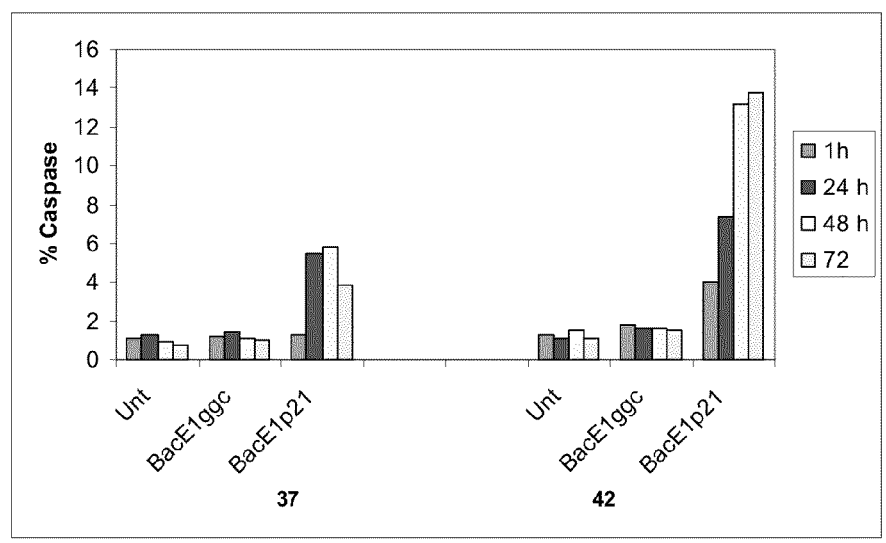
FIG. 36 is a graph that shows caspase activation. Cells were incubated with the indicated polypeptide at 37 or 42° C. for 1 h, harvested at the indicated time period, and analyzed for caspase activation by flow cytometry.

Caspase activation by Bac7-ELP-p21: In order to explore the role of apoptosis in Bac7-ELP1-p21 mediated cell death, we analyzed the activation of caspases at different time points after polypeptide treatment. SKOV-3 cells were treated for 1 h at 37 or 42° C. with various concentrations of Bac7-ELP2-p21 or the control construct lacking the p21 peptide, and active caspases were detected using a fluorescent caspase inhibitor and flow cytometry (FIG. 36). It was observed that Bac-ELP1-p21 treatment activated caspases to a level slightly above control cells at 37° C. The control polypeptide Bac7-ELP1-ggc caused no caspase activation at either treatment temperature. When Bac7-ELP1-p21 treatment was applied with hyperthermia, a high level of caspase activation was seen. The amount of caspase positive cells increased with time after treatment, reaching a maximum at 48 h after exposure to the polypeptide.

Figure 37:
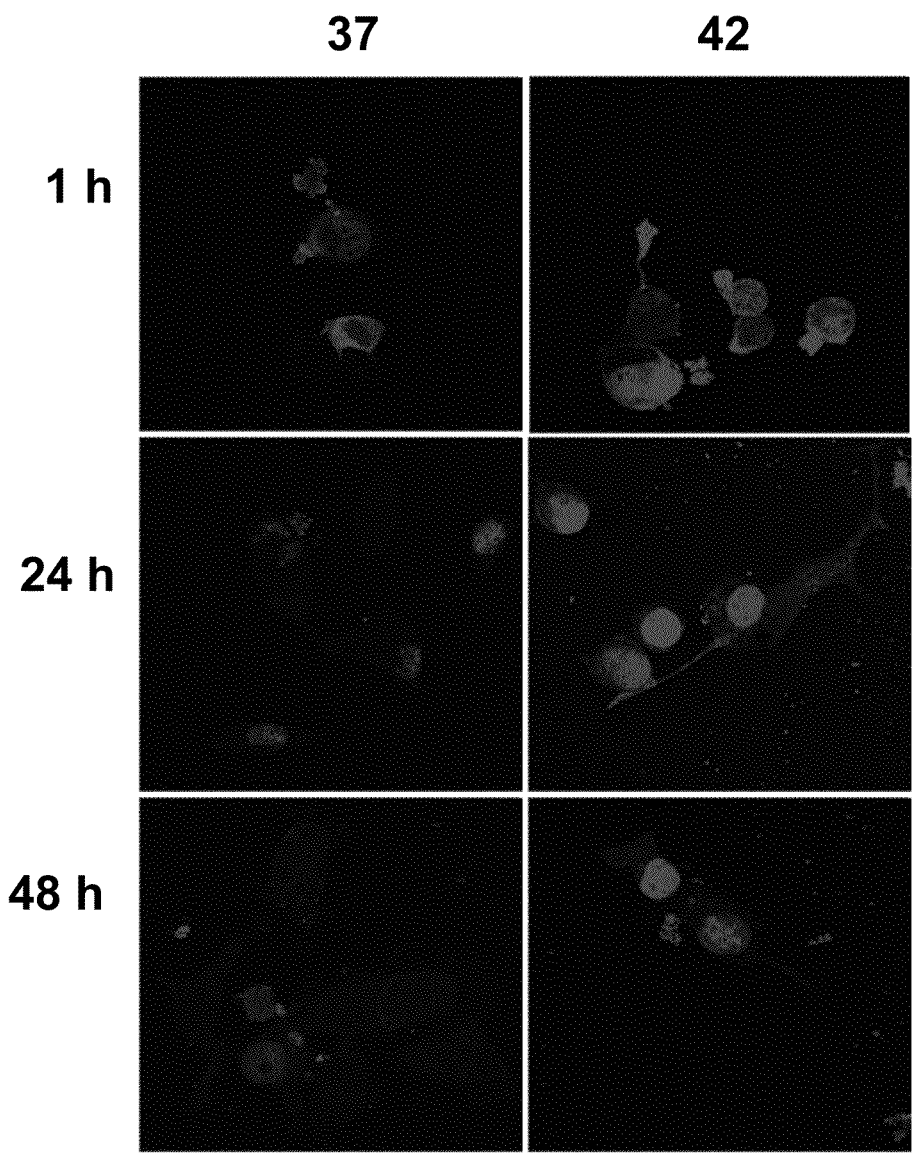
FIG. 37 shows internalization and subcellular localization of Bac7-ELP1-p21. SKOV-3 cells were treated with Bac7-ELP1-p21 for 1 h, and images were obtained at the indicated time points using a Leica laser scanning confocal microscope with a 100× oil immersion objective.

Internalization and Subcellular Localization of Bac7-ELP-p21: In order to confirm that the Bac7 peptide caused cellular internalization of Bac7-ELP1-p21, and to determine its subcellular localization, Bac7-ELP1-p21 was labeled with rhodhamine and incubated with the cells for 1 h at 37 or 42° C. The subcellular localization of the polypeptide was determined at various time points after treatment by laser scanning confocal microscopy. As shown in FIG. 37, immediately after 1 h, most of the polypeptide was seen attached to the cell membrane, with only a small amount of polypeptide localized inside the cells. When Bac7-ELP1-p21 treatment was combined with hyperthermia, large aggregates of the polypeptide could be seen attached to the cell surface (FIG. 37, top, right). 24 h after treatment at 37° C., the polypeptide was internalized by the cells, and the localization was a mixture of cytoplasmic and nuclear. 24 h after 42° C. treatment, Bac7-ELP1-p21 was almost exclusively localized in the nucleus (FIG. 37, middle panel). Polypeptide localization 48 h after treatment was similar to that observed at 24 h, with a mixture of cytoplasmic and nuclear localization at 37° C., and almost exclusively nuclear at 42° C. (FIG. 37, lower panel). These results confirm that the Bac7 peptide can deliver the large ELP-based polypeptide into the nucleus, and nuclear localization increases with time after treatment and with increasing intracellular polypeptide levels. These results, when taken with the results shown above for the c-Myc inhibitory polypeptide, are exciting because they demonstrate that delivery of the peptide inhibitor to a specific intracellular compartment is possible by changing the CPP used for delivery. Therefore, this system can be adapted for both cytoplasmic and nuclear drug targets.

Example 5

Pancreatic Cancer

Cancer of the pancreas is one of the deadliest cancer types, with nearly 28,000 people dying each year in the USA. The 5-Y survival rate for patients with pancreatic cancers is less than 5%. In addition to being one of the deadliest cancers, pancreatic cancer cells gain resistance to the chemotherapeutic agents used to treat them, making the treatment even more difficult. Improvement strategies for the treatment of pancreatic cancer should focus on specificity for the cancer cells and overcoming drug resistance. Our approach involves a thermally targeted drug delivery system which can be targeted to a specific body part with the help of hyperthermia, and can also overcome the drug resistance of the cells. The delivery system involves an inhibitory peptide derived from p21 attached to the thermally responsive delivery vehicle Bac7-ELP1. The fusion polypeptide Bac7-ELP-p21 was expressed and purified from $E. coli$. Panc-1 cells used as a model system to test the effectiveness of Bac7-ELP-p21 for inhibition of pancreatic cancer cell proliferation and for enhancing the toxicity of currently used drugs for the treatment of pancreatic cancer.

Figure 38:
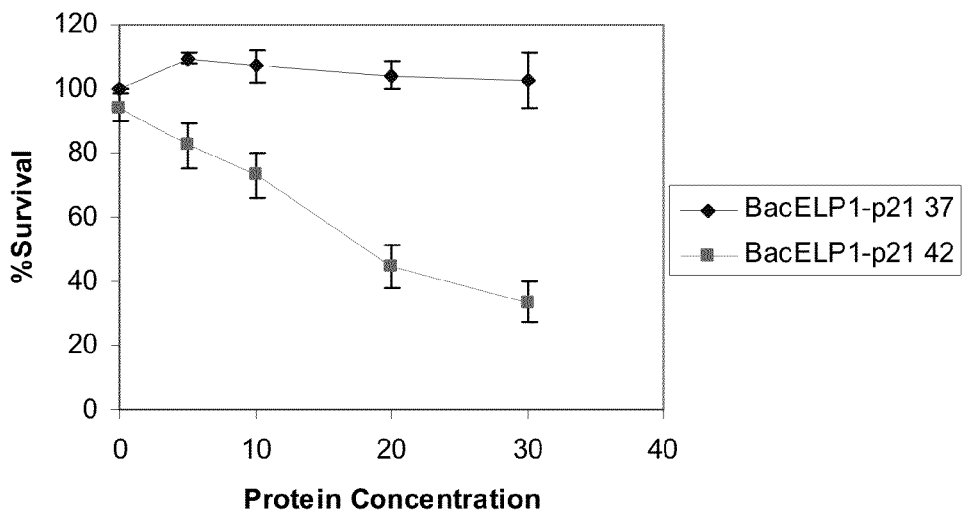
FIG. 38 is a set of graphs that show inhibition of Panc-1 Cell Proliferation by Bac7-ELP1-p21. A. Panc-1 cells were treated with the indicated polypeptide for 1 h at 37° C. or 42° C., then fresh media was replaced. Cell survival was measured after 72 h using the MTS assay. B. Panc-1 cells were treated with the indicated polypeptide (20 µM) for 1 h at 37 or 42° C. Cells were harvested daily and counted using a Coulter counter. Bars, SEM of three to five experiments.
Figure 38:
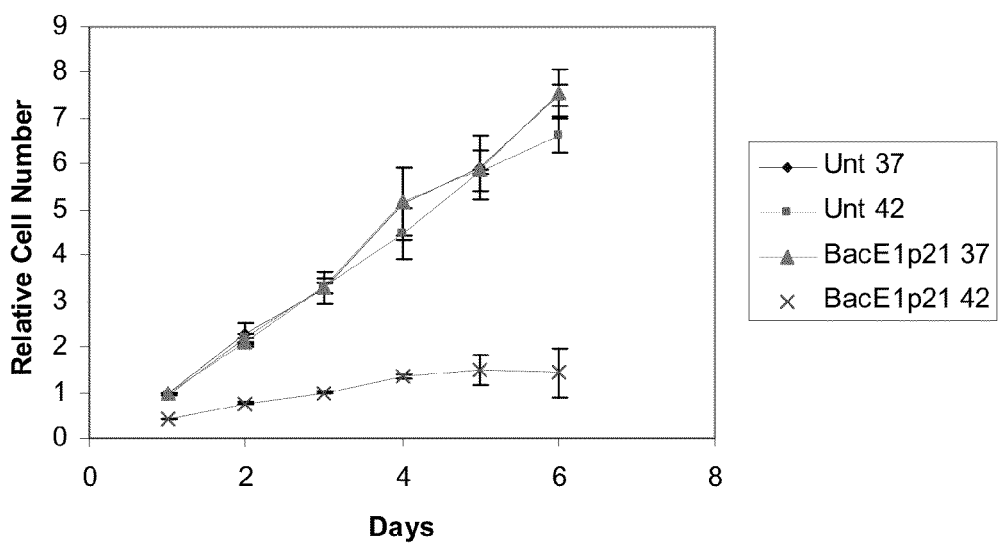

Effect of Bac7-ELP-p21 on pancreatic cancer cell proliferation: Panc-1 cells were treated with the indicated polypeptides for 1 h at 37 or 42° C. Cell viability was determined by MTS assay 3 days and 6 days after treatment. As seen in FIG. 38A, Bac7-ELP1-p21 treatment at 42° C. caused nearly 60-80% inhibition at 20 and 30 µM polypeptide concentration. No effect was observed at 37° C. Also, no effect was observed with the control polypeptide Bac7-ELP1-ggc at 37 or 42° C. (data not shown). These experiments demonstrate that the observed decrease in cell proliferation is due to the inhibitory peptide p21. The increase in inhibition seen at 42°

C. treatment compared to 37° C. treatment is due to the fact that more polypeptide is presented to the cell surface upon application of hyperthermia because of the aggregation of ELP1, which in turn leads to the entry of more polypeptide inside the cells. The effect of Bac7-ELP1-p21 on the proliferation of Panc-1 cells was also determined by daily cell counts following polypeptide treatment (FIG. 38B). At the dose tested (20 µM), Bac7-ELP1-p21 has no effect on Panc-1 cell proliferation after 37° C. treatment. However, following treatment with Bac7-ELP1-p21 at 42° C., Panc-1 cell proliferation is almost completely inhibited.

Figure 39:
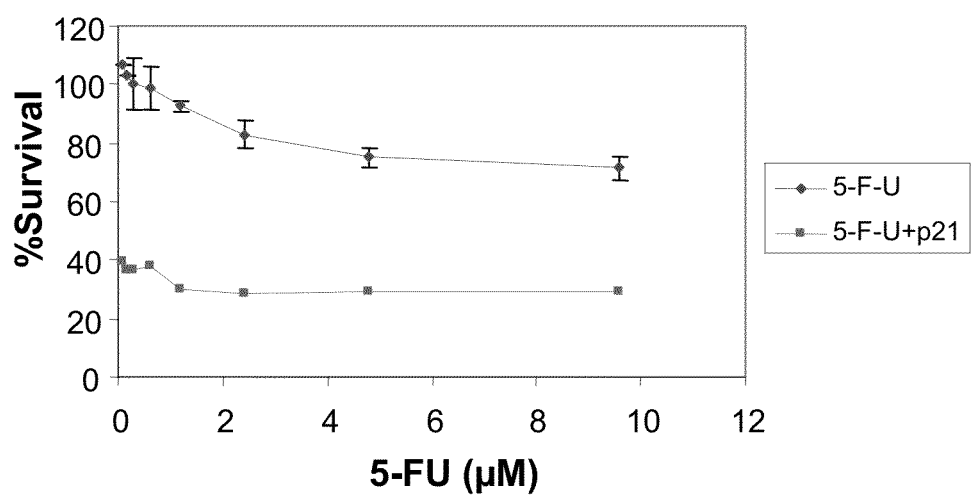
FIG. 39 shows inhibition of Panc-1 Cell Proliferation by 5-FU Alone or in Combination with Bac7-ELP-p21. Panc-1 cells were treated for 72 h with 5-F-U with or without pretreatment with Bac7-ELP1-p21 for 1 hr at 42° C. Cell proliferation was assessed by the MTS assay. Bars, SEM of 3 experiments.

Resistance to Current Chemotherapeutic Agents: One of the therapeutic agents currently used in the clinical setting for pancreatic cancer is 5-Fluorouracil (5-FU). 5-FU has shown effectiveness in pancreatic cancer treatment, but the development of drug resistance is a major limitation to 5-FU therapy. Panc-1 cells are highly resistant to 5-FU treatment. As shown in FIG. 39, upon increasing the concentration of 5-F-U beyond 10 µM, there is no increasing effect on cell proliferation. In contrast, Bac7-ELP1-p21 is quite effective for inhibition of Panc-1 proliferation (FIG. 38A and the 0 5-FU concentration in FIG. 39). If Panc-1 cells were pretreated for 1 h at 42° C. with Bac7-ELP1-p21, then treated with 5-FU, cell proliferation is dramatically reduced.

Throughout this application, and specifically, below, various references are mentioned. All references are incorporated herein by reference in their entirety and should be considered to be part of this application.

REFERENCES

1. Draeger, L. J. and Mullen, G. P. Interaction of the bHLH-zip domain of c-Myc with H1-type peptides. Characterization of helicity in the H1 peptides by NMR. J Biol Chem, 269: 1785-1793, 1994.
2. Schwartz, J. J. and Zhang, S. Peptide-mediated cellular delivery. Curr Opin Mol Ther, 2: 162-167., 2000.
3. Tomasinsig, L., Skerlavaj, B., Papo, N., Giabbai, B., Shai, Y., and Zanetti, M. Mechanistic and functional studies of the interaction of a proline-rich antimicrobial peptide with mammalian cells. J Biol Chem, 281: 383-391, 2006.
4. Ekholm, S. V. and Reed, S. I. Regulation of G(1) cyclin-dependent kinases in the mammalian cell cycle. Curr Opin Cell Biol, 12: 676-684, 2000.
5. Morgan, D. O. Principles of CDK regulation. Nature, 374: 131-134, 1995.
6. Brugarolas, J., Chandrasekaran, C., Gordon, J. I., Beach, D., Jacks, T., and Hannon, G. J. Radiation-induced cell cycle arrest compromised by p21 deficiency. Nature, 377: 552-557, 1995.
7. Deng, C., Zhang, P., Harper, J. W., Elledge, S. J., and Leder, P. Mice lacking p21CIP1/WAF1 undergo normal development, but are defective in G1 checkpoint control. Cell, 82: 675-684, 1995.
8. Niculescu, A. B., 3rd, Chen, X., Smeets, M., Hengst, L., Prives, C., and Reed, S. I. Effects of p21(Cip1/Waf1) at both the G1/S and the G2/M cell cycle transitions: pRb is a critical determinant in blocking DNA replication and in preventing endoreduplication. Mol Cell Biol, 18: 629-643, 1998.
9. Ogryzko, V. V., Wong, P., and Howard, B. H. WAF™ retards S-phase progression primarily by inhibition of cyclin-dependent kinases. Mol Cell Biol, 17: 4877-4882, 1997.
10. Mutoh, M., Lung, F. D., Long, Y. Q., Roller, P. P., Sikorski, R. S., and O'Connor, P. M. A p21(Waf1/Cip1)carboxyl-terminal peptide exhibited cyclin-dependent kinase-inhibitory activity and cytotoxicity when introduced into human cells. Cancer Res, 59: 3480-3488, 1999.
11. Wang, C., Zhang, J., Liu, A., Sun, B., and Zhao, Y. Surgical treatment of primary midbrain gliomas. Surgical Neurology, 53: 41-51, 2000.
12. Viar, V. Advances in surgical treatment of melanoma. Nursing Clinics of North America, 36: 507-515, 2001.
13. Chao, C. and Goldberg, M. Surgical treatment of metastatic pulmonary soft-tissue sarcoma. Oncology (Huntington), 14: 835-841; discussion 842-834, 2000.
14. Tobias, J. S. The role of radiotherapy in the management of cancer—an overview Annals of the Academy of Medicine, Singapore, 25: 371-379, 1996.
15. Allen, T. M. Liposomal drug formulation: rationale for development and what we can expect in the future. Drugs, 56: 747-756, 1998.
16. Langer, R. Drug delivery and targeting. Nature (Lond.), 392 (Suppl.): 5-10, 1998.
17. Torchilin, V. P. Polymer-coated long-circulating microparticulate pharmaceuticals. J. Microencapsul, 15: 1-19, 1998.
18. Jones, M. and J., L. Polymeric micelles: a new generation of colloidal drug carriers. Eur. J. Pharm. Biopharm., 48: 101-111, 1999.
19. Cassidy, J., Duncan, R., Morrison, G. J., Strohalm, J., Plocova, D., Kopecek, J., and Kaye, S. B. Activity of N-(2-hydroxypropyl)methacrylamide copolymers containing daunomycin against a rat tumour model. Biochem. Pharmacol., 38: 875-879, 1989.
20. Maeda, H., Seymour, L. W., and Miyamoto, Y. Conjugates of anticancer agents and polymers: advantages of macromolecular therapeutics in vivo. Bioconjug. Chem., 3: 351-362, 1992.
21. Takakura, Y., Fujita, T., Hashida, M., and Sezaki, H. Disposition characteristics of macromolecules in tumor-bearing mice. Pharm. Res, 7: 339-346, 1990.
22. Yamaoka, T., Tabata, Y., and Ikada, Y. Distribution and tissue uptake of poly(ethylene glycol) with different molecular weights after intravenous administration to mice. J. Pharm. Sci, 83: 601-606, 1994.
23. Duncan, R., Coatsworth, J. K., and Burtles, S. Preclinical toxicology of a novel polymeric antitumour agent: HPMA copolymer-doxorubicin (PK1). Hum. Exp. Toxicol, 17: 93-104, 1998.
24. Seymour, L. W., Duncan, R., Kopeckova, P., and Kopecek, J. Daunomycin- and adriamycin-N-(2-hydroxypropyl) methacrylamide copolymer conjugates; toxicity reduction by improved drug-delivery. Cancer. Treat. Rev., 14: 319-327, 1987.
25. Yeung, T. K., Hopewell, J. W., Simmonds, R. H., Seymour, L. W., Duncan, R., Bellini, O., Grandi, M., Spreafico, F., Strohalm, J., and Ulbrich, K. Reduced cardiotoxicity of doxorubicin given in the form of N-(2-hydroxypropyl)methacrylamide conjugates: and experimental study in the rat. Cancer Chemother. Pharmacol, 29: 105-111, 1991.
26. St'astny, M., Strohalm, J., Plocova, D., Ulbrich, K., and Rihova, B. A possibility to overcome P-glycoprotein (PGP)-mediated multidrug resistance by antibody-targeted drugs conjugated to N-(2-hydroxypropyl)methacrylamide (HPMA) copolymer carrier. Eur. J. Cancer, 35: 459-466, 1999.
27. Ryser, H. J. and Shen, W. C. Conjugation of methotrexate to poly(L-lysine) increases drug transport and overcomes drug resistance in cultured cells. Proc. Natl. Acad. Sci. USA, 75: 3867-3870, 1978.

28. Ohkawa, K., Hatano, T., Yamada, K., Joh, K., Takada, K., Tsukada, Y., and Matsuda, M. Bovine serum albumin-doxorubicin conjugate overcomes multidrug resistance in a rat hepatoma. Cancer Res, 53: 4238-4242, 1993.
29. Minko, T., Kopeckova, P., Pozharov, V., and Kopecek, J. HPMA copolymer bound adriamycin overcomes MDR1 gene encoded resistance in a human ovarian carcinoma cell line. J Control Release, 54: 223-233., 1998.
30. Kopecek, J., Kopeckova, P., Minko, T., and Lu, Z. HPMA copolymer-anticancer drug conjugates: design, activity, and mechanism of action. Eur J Pharm Biopharm, 50: 61-81, 2000.
31. Kopecek, J. Smart and genetically engineered biomaterials and drug delivery systems. Eur J Pharm Sci, 20:1-16, 2003.
32. Issels, R. D. Regional hyperthermia combined with systemic chemotherapy of locally advanced sarcomas: preclinical aspects and clinical results. Recent Results Cancer Res, 138: 81-90, 1995.
33. Feyerabend, T., Steeves, R., Wiedemann, G. J., Richter, E., and Robins, H. I. Rationale and clinical status of local hyperthermia, radiation, and chemotherapy in locally advanced malignancies. Anticancer Res, 17: 2895-2897, 1997.
34. van Vulpen, M., Raaymakers, B. W., de Leeuw, A. A., van de Kamer, J. B., van Moorselaar, R. J., Hobbelink, M. G., Battermann, J. J., and Lagendijk, J. J. Prostate perfusion in patients with locally advanced prostate carcinoma treated with different hyperthermia techniques. J Urol, 168: 1597-1602, 2002.
35. Falk, M. H. and Issels, R. D. Hyperthermia in oncology. Int J Hyperthermia, 17: 1-18., 2001.
36. Dewhirst, M. W., Prosnitz, L., Thrall, D., Prescott, D., Clegg, S., Charles, C., MacFall, J., Rosner, G., Samulski, T., Gillette, E., and LaRue, S. Hyperthermic treatment of malignant diseases: current status and a view toward the future. Semin. Oncol., 24: 616-625, 1997.
37. Takahashi, I., Emi, Y., Hasuda, S., Kakeji, Y., Maehara, Y., and Sugimachi, K. Clinical application of hyperthermia combined with anticancer drugs for the treatment of solid tumors. Surgery, 131: S78-84, 2002.
38. Jung, T., Kamm, W., Breitenbach, A., Kaiserling, E., Xiao, J. X., and Kissel, T. Biodegradable nanoparticles for oral delivery of peptides: is there a role for polymers to affect mucosal uptake? Eur J Pharm Biopharm, 50: 147-160, 2000.
39. Banerjee, R. Liposomes: applications in medicine. J Biomater Appl, 16: 3-21, 2001.
40. Torchilin, V. P. and Levchenko, T. S. TAT-liposomes: a novel intracellular drug carrier. Curr Protein Pept Sci, 4: 133-140, 2003.
41. Kong, G. and Dewhirst, M. W. Hyperthermia and liposomes. Int J Hyperthermia, 15: 345-370, 1999.
42. Yuk, S. H. and Bae, Y. H. Phase-transition polymers for drug delivery. Crit. Rev Ther Drug Carrier Syst, 16: 385-423, 1999.
43. Kikuchi, A. and Okano, T. Pulsatile drug release control using hydrogels. Adv Drug Deliv Rev, 54: 53-77, 2002.
44. Weng, H., Zhou, J., Tang, L., and Hu, Z. Tissue responses to thermally-responsive hydrogel nanoparticles. J Biomater Sci Polym Ed, 15: 1167-1180, 2004.
45. Chaw, C. S., Chooi, K. W., Liu, X. M., Tan, C. W., Wang, L., and Yang, Y. Y. Thermally responsive core-shell nanoparticles self-assembled from cholesteryl end-capped and grafted polyacrylamides:; drug incorporation and in vitro release. Biomaterials, 25: 4297-4308, 2004.
46. Kong, G., Anyarambhatla, G., Petros, W. P., Braun, R. D., Colvin, O. M., Needham, D., and Dewhirst, M. W. Efficacy of liposomes and hyperthermia in a human tumor xenograft model: importance of triggered drug release. Cancer Res, 60: 6950-6957, 2000.
47. Derossi, D., Calvet, S., Trembleau, A., Brunissen, A., Chassaing, G., and Prochiantz, A. Cell internalization of the third helix of the Antennapedia homeodomain is receptor-independent. Journal of Biological Chemistry, 271: 18188-18193, 1996.
48. Giorello, L., Clerico, L., Pescarolo, M. P., Vikhanskaya, F., Salmona, M., Colella, G., Bruno, S., Mancuso, T., Bagnasco, L., Russo, P., and Parodi, S Inhibition of cancer cell growth and c-Myc transcriptional activity by a c-Myc helix 1-type peptide fused to an internalization sequence. Cancer Research, 58: 3654-3659, 1998.
49. Raucher, D. and Chilkoti, A. Enhanced uptake of a thermally responsive polypeptide by tumor cells in response to its hyperthermia-mediated phase transition. Cancer Res, 61: 7163-7170, 2001.
50. Meyer, D. E., Kong, G. A., Dewhirst, M. W., Zalutsky, M. R., and Chilkoti, A. Targeting a Genetically Engineered Elastin-like Polypeptide to Solid Tumors by Local Hyperthermia. Cancer Res, 61: 1548-1554, 2001.
51. Liu, W., Dreher, M. R., Chow, D. C., Zalutsky, M. R., and Chilkoti, A. Tracking the in vivo fate of recombinant polypeptides by isotopic labeling. J Control Release, 114: 184-192, 2006.
52. Liu, W., Dreher, M. R., Furgeson, D. Y., Peixoto, K. V., Yuan, H., Zalutsky, M. R., and Chilkoti, A. Tumor accumulation, degradation and pharmacokinetics of elastin-like polypeptides in nude mice. J Control Release, 2006.
53. Fujiwara, K. and Watanabe, T. Effects of hyperthermia, radiotherapy and thermoradiotherapy on tumor microvascular permeability. Acta Pathol Jpn, 40: 79-84, 1990.
54. Gerlowski, L. E. and Jain, R. K. Effect of hyperthermia on microvascular permeability to macromolecules in normal and tumor tissues. Int J Microcirc Clin Exp, 4: 363-372, 1985.
55. Jain, R. K. Transport of molecules across tumor vasculature. Cancer Metastasis Rev, 6: 559-593, 1987.
56. Dreher, M. R., Raucher, D., Balu, N., Michael Colvin, O., Ludeman, S. M., and Chilkoti, A. Evaluation of an elastin-like polypeptide-doxorubicin conjugate for cancer therapy. J Control Release, 91: 31-43, 2003.
57. Derossi, D., Joliot, A. H., Chassaing, G., and Prochiantz, A. The third helix of the Antennapedia homeodomain translocates through biological membranes. Journal of Biological Chemistry, 269: 10444-10450, 1994.
58. Weeks, B. S., Desai, K., Loewenstein, P. M., Klotman, M. E., Klotman, P. E., Green, M., and Kleinman, H. K. Identification of a novel cell attachment domain in the HIV-1 Tat protein and its 90-kDa cell surface binding protein. J Biol Chem, 268: 5279-5284, 1993.
59. Gennaro, R., Skerlavaj, B., and Romeo, D. Purification, composition, and activity of two bactenecins, antibacterial peptides of bovine neutrophils. Infect Immun, 57: 3142-3146, 1989.
60. Joliot, A., Pernelle, C., Deagostini-Bazin, H., and Prochiantz, A. Antennapedia homeobox peptide regulates neural morphogenesis. Proc Natl Acad Sci USA, 88: 1864-1868., 1991.
61. Perez, F., Joliot, A., Bloch-Gallego, E., Zahraoui, A., Triller, A., and Prochiantz, A. Antennapedia homeobox as a signal for the cellular internalization and nuclear addressing of a small exogenous peptide. J Cell Sci, 102 (Pt 4): 717-722, 1992.

62. Thoren, P. E., Persson, D., Karlsson, M., and Norden, B. The antennapedia peptide penetratin translocates across lipid bilayers—the first direct observation. FEBS Lett, 482: 265-268, 2000.
63. Astriab-Fisher, A., Sergueev, D., Fisher, M., Shaw, B. R., and Juliano, R. L. Conjugates of antisense oligonucleotides with the Tat and antennapedia cell-penetrating peptides: effects on cellular uptake, binding to target sequences, and biologic actions. Pharm Res, 19: 744-754, 2002.
64. Marty, C., Meylan, C., Schott, H., Ballmer-Hofer, K., and Schwendener, R. A. Enhanced heparan sulfate proteoglycan-mediated uptake of cell-penetrating peptide-modified liposomes. Cell Mol Life Sci, 61: 1785-1794, 2004.
65. Gratton, J. P., Yu, J., Griffith, J. W., Babbitt, R. W., Scotland, R. S., Hickey, R., Giordano, F. J., and Sessa, W. C. Cell-permeable peptides improve cellular uptake and therapeutic gene delivery of replication-deficient viruses in cells and in vivo. Nat Med, 9: 357-362, 2003.
66. Frankel, A. D. and Pabo, C. O. Cellular uptake of the tat protein from human immunodeficiency virus. Cell, 55: 1189-1193, 1988.
67. Vives, E., Brodin, P., and Lebleu, B. A truncated HIV-1 Tat protein basic domain rapidly translocates through the plasma membrane and accumulates in the cell nucleus. J Biol Chem, 272: 16010-16017, 1997.
68. Vives, E. Cellular uptake [correction of utake] of the Tat peptide: an endocytosis mechanism following ionic interactions. J Mol Recognit, 16: 265-271, 2003.
69. Vives, E., Richard, J. P., Rispal, C., and Lebleu, B. TAT peptide internalization: seeking the mechanism of entry. Curr Protein Pept Sci, 4: 125-132, 2003.
70. Fawell, S., Seery, J., Daikh, Y., Moore, C., Chen, L. L., Pepinsky, B., and Barsoum, J. Tat-mediated delivery of heterologous proteins into cells. Proc Natl Acad Sci USA, 91: 664-668, 1994.
71. Peitz, M., Pfannkuche, K., Rajewsky, K., and Edenhofer, F. Ability of the hydrophobic FGF and basic TAT peptides to promote cellular uptake of recombinant Cre recombinase: a tool for efficient genetic engineering of mammalian genomes. Proc Natl Acad Sci USA, 99: 4489-4494, 2002.
72. Koppelhus, U., Awasthi, S. K., Zachar, V., Holst, H. U., Ebbesen, P., and Nielsen, P. E. Cell-dependent differential cellular uptake of PNA, peptides, and PNA-peptide conjugates. Antisense Nucleic Acid Drug Dev, 12: 51-63, 2002.
73. Zhao, M., Kircher, M. F., Josephson, L., and Weissleder, R. Differential conjugation of tat peptide to superparamagnetic nanoparticles and its effect on cellular uptake. Bioconjug Chem, 13: 840-844, 2002.
74. Tseng, Y. L., Liu, J. J., and Hong, R. L. Translocation of liposomes into cancer cells by cell-penetrating peptides penetratin and tat: a kinetic and efficacy study. Mol Pharmacol, 62: 864-872, 2002.
75. Nori, A., Jensen, K. D., Tijerina, M., Kopeckova, P., and Kopecek, J. Tat-conjugated synthetic macromolecules facilitate cytoplasmic drug delivery to human ovarian carcinoma cells. Bioconjug Chem, 14: 44-50, 2003.
76. Nori, A., Jensen, K. D., Tijerina, M., Kopeckova, P., and Kopecek, J. Subcellular trafficking of HPMA copolymer-Tat conjugates in human ovarian carcinoma cells. J Control Release, 91: 53-59, 2003.
77. Nori, A. and Kopecek, J. Intracellular targeting of polymer-bound drugs for cancer chemotherapy. Adv Drug Deliv Rev, 57: 609-636, 2005.
78. Jensen, K. D., Nori, A., Tijerina, M., Kopeckova, P., and Kopecek, J. Cytoplasmic delivery and nuclear targeting of synthetic macromolecules. J Control Release, 87: 89-105, 2003.
79. Schwarze, S. R., Ho, A., Vocero-Akbani, A., and Dowdy, S. F. In vivo protein transduction: delivery of a biologically active protein into the mouse. Science, 285: 1569-1572, 1999.
80. Toro, A. and Grunebaum, E. TAT-mediated intracellular delivery of purine nucleoside phosphorylase corrects its deficiency in mice. J Clin Invest, 116: 2717-2726, 2006.
81. Blackwell, N. M., Sembi, P., Newson, J. S., Lawrence, T., Gilroy, D. W., and Kabouridis, P. S. Reduced infiltration and increased apoptosis of leukocytes at sites of inflammation by systemic administration of a membrane-permeable IkappaBalpha repressor. Arthritis Rheum, 50: 2675-2684, 2004.
82. Tani, A., Lee, S., Oishi, O., Aoyagi, H., and Ohno, M. Interaction of the fragments characteristic of bactenecin 7 with phospholipid bilayers and their antimicrobial activity. J Biochem (Tokyo), 117: 560-565, 1995.
83. Sadler, K., Eom, K. D., Yang, J. L., Dimitrova, Y., and Tam, J. P. Translocating proline-rich peptides from the antimicrobial peptide bactenecin 7. Biochemistry, 41: 14150-14157, 2002.
84. Hawiger, J. Noninvasive intracellular delivery of functional peptides and proteins. Curr Opin Chem Biol, 3: 89-94, 1999.
85. Massodi, I., Bidwell, G. L., 3rd, and Raucher, D. Evaluation of cell penetrating peptides fused to elastin-like polypeptide for drug delivery. J Control Release, 108: 396-408, 2005.
86. Gonos, E. S, and Spandidos, D. A. Oncogenes in cellular immortalisation and differentiation (review). Anticancer Research, 13: 1117-1122, 1993.
87. Ball, K. L., Lain, S., Fahraeus, R., Smythe, C., and Lane, D. P. Cell-cycle arrest and inhibition of Cdk4 activity by small peptides based on the carboxy-terminal domain of p21WAF1. Curr Biol, 7: 71-80, 1997.
88. Bonfanti, M., Taverna, S., Salmona, M., D'Incalci, M., and Broggini, M. p21WAF1-derived peptides linked to an internalization peptide inhibit human cancer cell growth. Cancer Res, 57: 1442-1446, 1997.
89. Mattock, H., Lane, D. P., and Warbrick, E Inhibition of cell proliferation by the PCNA-binding region of p21 expressed as a GFP miniprotein. Exp Cell Res, 265: 234-241, 2001.
90. Khanna, A. K., Plummer, M., Nilakantan, V., and Pieper, G. M. Recombinant p21 protein inhibits lymphocyte proliferation and transcription factors. J Immunol, 174: 7610-7617, 2005.
91. Tunnemann, G., Martin, R. M., Haupt, S., Patsch, C., Edenhofer, F., and Cardoso, M. C. Cargo-dependent mode of uptake and bioavailability of TAT-containing proteins and peptides in living cells. Faseb J, 20: 1775-1784, 2006.
92. Baker, R. D., Howl, J., and Nicholl, I. D. A sychnological cell penetrating peptide mimic of p21(WAF1/CIP1) is pro-apoptogenic. Peptides, 28: 731-740, 2007.
93. Bidwell, G. L., 3rd and Raucher, D. Application of thermally responsive polypeptides directed against c-Myc transcriptional function for cancer therapy. Mol Cancer Ther, 4: 1076-1085, 2005.
94. Giorello, L., Clerico, L., Pescarolo, M. P., Vikhanskaya, F., Salmona, M., Colella, G., Bruno, S., Mancuso, T., Bagnasco, L., Russo, P., and Parodi, S Inhibition of cancer cell 94. growth and c-Myc transcriptional activity by a c-Myc helix 1-type peptide fused to an internalization sequence. Cancer Res, 58: 3654-3659, 1998.
95. Pescarolo, M. P., Bagnasco, L., Malacarne, D., Melchiori, A., Valente, P., Millo, E., Bruno, S., Basso, S., and Parodi, S. A retro-inverso peptide homologous to helix 1 of c-Myc is a potent and specific inhibitor of proliferation in different cellular systems. Faseb J, 15: 31-33, 2001.
96. Racanicchi, S., Maccherani, C., Liberatore, C., Billi, M., Gelmetti, V., Panigada, M., Rizzo, G., Nervi, C., and Grignani, F. Targeting fusion protein/corepressor contact restores differentiation response in leukemia cells. Embo J, 24: 1232-1242, 2005.
97. Polo, J. M., Dell'Oso, T., Ranuncolo, S. M., Cerchietti, L., Beck, D., Da Silva, G. F., Prive, G. G., Licht, J. D., and Melnick, A. Specific peptide interference reveals BCL6 transcriptional and oncogenic mechanisms in B-cell lymphoma cells. Nat Med, 10: 1329-1335, 2004.
98. Snyder, E. L., Meade, B. R., Saenz, C. C., and Dowdy, S. F. Treatment of terminal peritoneal carcinomatosis by a transducible p53-activating peptide. PLoS Biol, 2: E36, 2004.
99. Perea, S. E., Reyes, O., Puchades, Y., Mendoza, O., Vispo, N. S., Torrens, I., Santos, A., Silva, R., Acevedo, B., Lopez, E., Falcon, V., and Alonso, D. F. Antitumor effect of a novel proapoptotic peptide that impairs the phosphorylation by the protein kinase 2 (casein kinase 2). Cancer Res, 64: 7127-7129, 2004.
100. Katterle, Y., Brandt, B. H., Dowdy, S. F., Niggemann, B., Zanker, K. S., and Dittmar, T. Antitumour effects of PLC-gamma1-(SH2)-2-TAT fusion proteins on EGFR/c-erbB-2-positive breast cancer cells. Br J Cancer, 90: 230-235, 2004.
101. Datta, K., Sundberg, C., Karumanchi, S. A., and Mukhopadhyay, D. The 104-123 amino acid sequence of the beta-domain of von Hippel-Lindau gene product is sufficient to inhibit renal tumor growth and invasion. Cancer Res, 61: 1768-1775, 2001.
102. Michod, D., Yang, J. Y., Chen, J., Bonny, C., and Widmann, C. A RasGAP-derived cell permeable peptide potently enhances genotoxin-induced cytotoxicity in tumor cells. Oncogene, 23: 8971-8978, 2004.
103. Fulda, S., Wick, W., Weller, M., and Debatin, K. M. Smac agonists sensitize for Apo2L/TRAIL- or anticancer drug-induced apoptosis and induce regression of malignant glioma in vivo. Nat Med, 8: 808-815, 2002.
104. Yang, L., Mashima, T., Sato, S., Mochizuki, M., Sakamoto, H., Yamori, T., Oh-Hara, T., and Tsuruo, T. Predominant suppression of apoptosome by inhibitor of apoptosis protein in non-small cell lung cancer H460 cells: therapeutic effect of a novel polyarginine-conjugated Smac peptide. Cancer Res, 63: 831-837, 2003.
105. Nagel-Wolfrum, K., Buerger, C., Wittig, I., Butz, K., Hoppe-Seyler, F., and Groner, B. The interaction of specific peptide aptamers with the DNA binding domain and the dimerization domain of the transcription factor Stat3 inhibits transactivation and induces apoptosis in tumor cells. Mol Cancer Res, 2: 170-182, 2004.
106. Walensky, L. D., Kung, A. L., Escher, I., Malia, T. J., Barbuto, S., Wright, R. D., Wagner, G., Verdine, G. L., and Korsmeyer, S. J. Activation of apoptosis in vivo by a hydrocarbon-stapled BH3 helix. Science, 305: 1466-1470, 2004.
107. Agou, F., Courtois, G., Chiaravalli, J., Baleux, F., Coic, Y. M., Traincard, F., Israel, A., and Veron, M Inhibition of NF-kappa B activation by peptides targeting NF-kappa B essential modulator (nemo) oligomerization. J Biol Chem, 279: 54248-54257, 2004.
108. Plescia, J., Salz, W., Xia, F., Pennati, M., Zaffaroni, N., Daidone, M. G., Meli, M., Dohi, T., Fortugno, P., Nefedova, Y., Gabrilovich, D. I., Colombo, G., and Alfieri, D. C. Rational design of shepherdin, a novel anticancer agent. Cancer Cell, 7: 457-468, 2005.
109. Shin, I., Edl, J., Biswas, S., Lin, P. C., Mernaugh, R., and Arteaga, C. L. Proapoptotic activity of cell-permeable anti-Akt single-chain antibodies. Cancer Res, 65: 2815-2824, 2005.
110. Rozek, T., Wegener, K. L., Bowie, J. H., Olver, I. N., Carver, J. A., Wallace, J. C., and Tyler, M. J. The antibiotic and anticancer active aurein peptides from the Australian Bell Frogs Litoria aurea and Litoria raniformis the solution structure of aurein 1.2. Eur J Biochem, 267: 5330-5341, 2000.
111. Wang, J. L., Zhang, Z. J., Choksi, S., Shan, S., Lu, Z., Croce, C. M., Alnemri, E. S., Korngold, R., and Huang, Z. Cell permeable Bcl-2 binding peptides: a chemical approach to apoptosis induction in tumor cells. Cancer Res, 60: 1498-1502, 2000.
112. Alves, P. M., Faure, O., Graff-Dubois, S., Gross, D. A., Cornet, S., Chouaib, S., Miconnet, I., Lemonnier, F. A., and Kosmatopoulos, K. EphA2 as target of anticancer immunotherapy: identification of HLA-A*0201-restricted epitopes. Cancer Res, 63: 8476-8480, 2003.
113. Park, B. W., Zhang, H. T., Wu, C., Berezov, A., Zhang, X., Dua, R., Wang, Q., Kao, G., O'Rourke, D. M., Greene, M. I., and Murali, R. Rationally designed anti-HER2/neu peptide mimetic disables P185HER2/neu tyrosine kinases in vitro and in vivo. Nat Biotechnol, 18: 194-198, 2000.
114. May, M. J., D'Acquisto, F., Madge, L. A., Glockner, J., Pober, J. S., and Ghosh, S. Selective inhibition of NF-kappaB activation by a peptide that blocks the interaction of NEMO with the IkappaB kinase complex. Science, 289: 1550-1554, 2000.
115. Takada, Y., Singh, S., and Aggarwal, B. B. Identification of a p65 peptide that selectively inhibits NF-kappa B activation induced by various inflammatory stimuli and its role in down-regulation of NF-kappaB-mediated gene expression and up-regulation of apoptosis. J Biol Chem, 279: 15096-15104, 2004.
116. Lin, Y. Z., Yao, S. Y., Veach, R. A., Torgerson, T. R., and Hawiger, J Inhibition of nuclear translocation of transcription factor NF-kappa B by a synthetic peptide containing a cell membrane-permeable motif and nuclear localization sequence. J Biol Chem, 270: 14255-14258, 1995.
117. Loiarro, M., Sette, C., Gallo, G., Clacci, A., Fanto, N., Mastroianni, D., Carminati, P., and Ruggiero, V. Peptide-mediated interference of TIR domain dimerization in MyD88 inhibits interleukin-1-dependent activation of NF-{kappa} B. J Biol Chem, 280: 15809-15814, 2005.
118. Hiromura, M., Okada, F., Obata, T., Auguin, D., Shibata, T., Roumestand, C., and Noguchi, M Inhibition of Akt kinase activity by a peptide spanning the betaA strand of the proto-oncogene TCL1. J Biol Chem, 279: 53407-53418, 2004.
119. Kelemen, B. R., Hsiao, K., and Goueli, S. A. Selective in vivo inhibition of mitogen-activated protein kinase activation using cell-permeable peptides. J Biol Chem, 277: 8741-8748, 2002.
120. Lee, D. G., Hahm, K. S., Park, Y., Kim, H. Y., Lee, W., Lim, S. C., Seo, Y. K., and Choi, C. H. Functional and structural characteristics of anticancer peptide Pep27 analogues. Cancer Cell Int, 5: 21, 2005.

121. Chen, H. M., Wang, W., Smith, D., and Chan, S. C. Effects of the anti-bacterial peptide cecropin B and its analogs, cecropins B-1 and B-2, on liposomes, bacteria, and cancer cells. Biochim Biophys Acta, 1336: 171-179, 1997.

122. Baker, M. A., Maloy, W. L., Zasloff, M., and Jacob, L. S. Anticancer efficacy of Magainin2 and analogue peptides. Cancer Res, 53: 3052-3057, 1993.

123. Mai, J. C., Mi, Z., Kim, S. H., Ng, B., and Robbins, P. D. A proapoptotic peptide for the treatment of solid tumors. Cancer Res, 61: 7709-7712, 2001.

124. Lichtenstein, A., Ganz, T., Selsted, M. E., and Lehrer, R. I. In vitro tumor cell cytolysis mediated by peptide defensins of human and rabbit granulocytes. Blood, 68: 1407-1410, 1986.

125. Futaki, S., Suzuki, T., Ohashi, W., Yagami, T., Tanaka, S., Ueda, K., and Sugiura, Y. Arginine-rich peptides. An abundant source of membrane-permeable peptides having potential as carriers for intracellular protein delivery. J Biol Chem, 276: 5836-5840, 2001.

126. Elliott, G. and O'Hare, P. Intercellular trafficking and protein delivery by a herpesvirus structural protein. Cell, 88: 223-233, 1997.

127. Pooga, M., Hallbrink, M., Zorko, M., and Langel, U. Cell penetration by transportan. Faseb J, 12: 67-77, 1998.

128. Oehlke, J., Scheller, A., Wiesner, B., Krause, E., Beyermann, M., Klauschenz, E., Melzig, M., and Bienert, M. Cellular uptake of an alpha-helical amphipathic model peptide with the potential to deliver polar compounds into the cell interior non-endocytically. Biochim Biophys Acta, 1414: 127-139, 1998.

129. Morris, M. C., Depollier, J., Mery, J., Heitz, F., and Divita, G. A peptide carrier for the delivery of biologically active proteins into mammalian cells. Nat Biotechnol, 19: 1173-1176, 2001.

130. Elmquist, A., Lindgren, M., Bartfai, T., and Langel, U. VE-cadherin-derived cell-penetrating peptide, pVEC, with carrier functions. Exp Cell Res, 269: 237-244, 2001.

131. Derossi, D., Chassaing, G., and Prochiantz, A. Trojan peptides: the penetratin system for intracellular delivery. Trends Cell Biol, 8: 84-87, 1998.

132. Chilkoti, A., Dreher, M. R., Meyer, D. E., and Raucher, D. Targeted drug delivery by thermally responsive polymers. Adv Drug Deliv Rev, 54: 613-630, 2002.

133. Meyer, D. E. and Chilkoti, A. Purification of Recombinant Proteins by Fusion with Thermally Responsive Polypeptides. Nature Biotechnology, 17: 1112-1115, 1999.

134. Meyer, D. E., Shin, B. C., Kong, G. A., Dewhirst, M. W., and Chilkoti, A. Drug targeting using thermally responsive polymers and local hyperthermia. J Control Release, 74: 213-224, 2001.

135. Urry, D. W., Luan, C.-H., Parker, T. M., Gowda, D. C., Prasad, K. U., Reid, M. C., and Safavy, A. Temperature of Polypeptide Inverse Temperature Transition Depends on Mean Residue Hydrophobicity. J. Am. Chem. Soc., 113: 4346-4348, 1991.

136. Hallbrink, M., Floren, A., Elmquist, A., Pooga, M., Bartfai, T., and Langel, U. Cargo delivery kinetics of cell-penetrating peptides. Biochim Biophys Acta, 1515: 101-109, 2001.

137. Hildebrandt, B., Wust, P., Ahlers, O., Dieing, A., Sreenivasa, G., Kerner, T., Felix, R., and Riess, H. The cellular and molecular basis of hyperthermia. Crit. Rev Oncol Hematol, 43: 33-56, 2002.

138. Soldani, C., Bottone, M. G., Biggiogera, M., Alpini, C., Scovassi, A. I., Martin, T., and Pellicciari, C. Nuclear localization of phosphorylated c-Myc protein in human tumor cells. Eur J Histochem, 46: 377-380, 2002.

139. Abrams, H. D., Rohrschneider, L. R., and Eisenman, R. N. Nuclear location of the putative transforming protein of avian myelocytomatosis virus. Cell, 29: 427-439, 1982.

140. Walhout, A. J. M., Gubbels, J. M., Bernards, R., van der Vliet, P. C., and Timmers, H. T. M. c-Myc/Max heterodimers bind cooperatively to the E-box sequences located in the first intron of the rat ornithine decarboxylase (ODC) gene. Nucleic Acids Res, 25: 1516-1525, 1997.

141. Shim, H., Dolde, C., Lewis, B. C., Wu, C. S., Dang, G., Jungmann, R. A., Dalla-Favera, R., and Dang, C. V. c-Myc transactivation of LDH-A: implications for tumor metabolism and growth. Proc Natl Acad Sci USA, 94: 6658-6663, 1997.

142. Blackwood, E. M., Luscher, B., and Eisenman, R. N. Myc and Max associate in vivo. Genes Dev, 6: 71-80, 1992.

143. Bidwell, G. L., 3rd, Fokt, I., Priebe, W., and Raucher, D. Development of elastin-like polypeptide for thermally targeted delivery of doxorubicin. Biochem Pharmacol, 73: 620-631, 2007.

144. Shiah, J. G., Dvorak, M., Kopeckova, P., Sun, Y., Peterson, C. M., and Kopecek, J. Biodistribution and antitumour efficacy of long-circulating N-(2-hydroxypropyl)methacrylamide copolymer-doxorubicin conjugates in nude mice. Eur J Cancer, 37: 131-139, 2001.

145. Padilla De Jesus, O. L., Ihre, H. R., Gagne, L., Frechet, J. M., and Szoka, F. C., Jr. Polyester dendritic systems for drug delivery applications: in vitro and in vivo evaluation. Bioconjug Chem, 13: 453-461, 2002.

146. Gentilucci, L., Tolomelli, A., and Squassabia, F. Peptides and peptidomimetics in medicine, surgery and biotechnology. Curr Med Chem, 13: 2449-2466, 2006.

147. Goresky, C. A. Uptake in the liver: the nature of the process. Int Rev Physiol, 21: 65-101, 1980.

148. Pegg, A. E. Polyamine metabolism and its importance in neoplastic growth and a target for chemotherapy. Cancer Res, 48: 759-774, 1988.

149. Thomas, T. and Thomas, T. J. Polyamines in cell growth and cell death: molecular mechanisms and therapeutic applications. Cell Mol Life Sci, 58: 244-258, 2001.

150. Allen, E. D. and Natale, R. B. Effect of alpha-difluoromethylornithine alone and in combination with doxorubicin hydrochloride, cis-diamminedichloroplatinum (II), and vinblastine sulfate on the growth of P3J cells in vitro. Cancer Res, 46: 3550-3555, 1986.

151. Bakic, M., Chan, D., Freireich, E. J., Marton, L. J., and Zwelling, L. A. Effect of polyamine depletion by alpha-difluoromethylornithine or (2R,5R)-6-heptyne-2,5-diamine on drug-induced topoisomerase II-mediated DNA cleavage and cytotoxicity in human and murine leukemia cells. Cancer Res, 47: 6437-6443, 1987.

152. Cannistra, S. A., Bast, R. C., Jr., Berek, J. S., Bookman, M. A., Crum, C. P., DePriest, P. D., Garber, J. E., Koh, W. J., Markman, M., McGuire, W. P., 3rd, Rose, P. G., Rowinsky, E. K., Rustin, G. J., Skates, S. J., Vasey, P. A., and King, L. Progress in the management of gynecologic cancer: consensus summary statement. J Clin Oncol, 21: 129-132, 2003.

153. Vasey, P. A. Resistance to chemotherapy in advanced ovarian cancer: mechanisms and current strategies. Br J Cancer, 89 Suppl 3: S23-28, 2003.

Various changes in the details, steps and materials that have been described may be made by those skilled in the art within the principles and scope of the invention herein illustrated and defined in the appended claims. Therefore, while the present invention has been shown and described herein in what is believed to be the most practical and preferred embodiment, it is recognized that departures can be made therefrom within the scope of the invention, which is therefore not to be limited to the details disclosed herein but is to be accorded the full scope of the claims so as to embrace any and all equivalent apparatus and methods.

Unless otherwise indicated, all numbers expressing quantities, specifically amounts set forth when describing experimental testing, are to be understood as being modified in all instances by the term "about." Accordingly, unless indicated to the contrary, the numerical parameters set forth herein are approximations that may vary depending upon the desired properties sought to be determined by the present invention.

We claim:

1. A compound for delivery to a target site, comprising:
   (a) a cell penetrating peptide (CPP), wherein the CPP is selected from the group consisting of: SynB1, SynB1-NLS, poly-arginine, VP22, MAP, hCT-derived CPP, MPG, Buforin 2, PEP-1, and Magainin 2,
   (b) an elastin-like polypeptide (ELP), wherein the ELP comprises the sequence (VPGXG)$_n$ (SEQ ID NO: 44) or (VPGXG)$_n$WP (SEQ ID NO: 45), where n is an integer from about 30 to about 350 and each X is independently selected from valine (Val; V), glycine (Gly; G), and alanine (Ala; A) such that the selected Xs are Val:Gly:Ala in a 3:1:1 ratio or in a 1:7:8 ratio, and
   (c) a therapeutic peptide (TP).

2. The compound of claim 1, wherein the TP is selected from the group consisting of: Myc peptide, Retro-inverso Myc peptide, N-CoR fragments, BCL6-inhibitor peptide, P53C0 retro-inverso, Casein kinase II-blocking peptide, Phospholipase C g1, von Hippel-Landau, RasGAP cleavage Fragment, Smac5-DIABLO peptide, STAT3, BH3 domain helix, NEMO oligomerization-blocking peptide, Survivin Hsp90 binding domain, AKT single chain antibody, Aurein 1.2 and 3.1, Proapoptotic peptide from Bad, EphA2$_{58}$ and EphA2$_{550}$ for tumor immunotherapy, AHNP anti HER2/neu peptide mimic, IKKγ/NEMO Binding Domain (NBD) Inhibitory Peptide, p65 (Ser529/536) Inhibitory Peptide, p50 (NLS) Inhibitory Peptide, MyD88 Homodimerization Inhibitory Peptide, Akt (Isoforms 1,2,3) Inhibitory peptide, ERK Inhibitory Peptide, Pep27 analogues, insect cecropins (CB-1 and CB-2), magainins, Proapoptotic peptide, human neutrophil defensins and rabbit defensins.

3. The compound of claim 1, wherein the TP is selected from H1, p21, and p50.

4. The compound of claim 1, wherein the TP is H1.

5. The compound of claim 1, wherein the TP is p21.

6. A compound for delivery to a target site, comprising:
   (a) a cell penetrating peptide (CPP), wherein the CPP is Bac,
   (b) an elastin-like (ELP), wherein the ELP comprises the sequence (VPGXG)$_n$ (SEQ ID NO: 44), where n is 150 and each X is independently selected from valine (Val; V), glycine (Gly; G), and alanine (Ala; A) in a ratio of 5:3:2, and
   (c) a therapeutic peptide (TP), wherein the TP is p21.

7. A compound for delivery to a target site, comprising:
   (a) a cell penetrating peptide (CPP), wherein the CPP is Bac,
   (b) an elastin-like polypeptide (ELP), wherein the ELP comprises the sequence (VPGXG)$_n$ (SEQ ID NO: 44) or (VPGXG)$_n$WP (SEQ ID NO: 45), where n is an integer from about 30 to about 350 and each X is independently selected from valine (Val; V), glycine (Gly; G), and alanine (Ala; A) such that the selected Xs are Val:Gly:Ala in a 3:1:1 ratio or in a 1:7:8 ratio, and
   (c) a therapeutic peptide (TP), wherein the TP is p21.

8. A compound for delivery to a target site, comprising:
   (a) a cell penetrating peptide (CPP), wherein the CPP is selected from the group consisting of: Bac, SynB1, SynB1-NLS, poly-arginine, VP22, Transportan, MAP, pVEC, MTS, hCT-derived CPP, MPG, Buforin 2, PEP-1, and Magainin 2,
   (b) an elastin-like polypeptide (ELP), wherein the ELP comprises the sequence (VPGXG)$_n$ (SEQ ID NO:-44) or (VPGXG)$_n$WP (SEQ ID NO: 45), where n is an integer from about 30 to about 70 or about 200 to about 350, and where each X is independently selected from valine (Val; V), glycine (Gly; G), and alanine (Ala; A) such that the selected Xs are Val:Gly:Ala in a 3:1:1 ratio or in a 1:7:8 ratio, and
   (c) a therapeutic peptide (TP).

9. A compound for delivery to a target site, comprising:
   (a) a cell penetrating peptide (CPP), wherein the CPP includes SynB1,
   (b) an elastin-like polypeptide (ELP), wherein the ELP comprises the sequence (VPGXG)$_n$ (SEQ ID NO:-44) or (VPGXG)$_n$WP (SEQ ID NO: 45), where n is an integer from about 30 to about 350 and each X is independently selected from valine (Val; V), glycine (Gly; G), and alanine (Ala; A) such that the selected Xs are Val:Gly:Ala in a 3:1:1 ratio or in a 1:7:8 ratio, and
   (c) a therapeutic peptide (TP).

* * * * *